US006174706B1

(12) United States Patent
Vinci et al.

(10) Patent No.: US 6,174,706 B1
(45) Date of Patent: *Jan. 16, 2001

(54) DNA ENCODING TRIOL POLYKETIDE SYNTHASE

(75) Inventors: Victor A. Vinci, Indianapolis, IN (US); Michael J. Conder, Harrisonburg, VA (US); Phyllis C. McAda; Christopher D. Reeves, both of Woodenville, WA (US); John Rambosek, Seattle, WA (US); Charles Ray Davis, Lynnwood, WA (US); Lee E. Hendrickson, Carnation, WA (US)

(73) Assignee: Merck & Co., Inc., Rahway, NJ (US)

( * ) Notice: Under 35 U.S.C. 154(b), the term of this patent shall be extended for 0 days.

This patent is subject to a terminal disclaimer.

(21) Appl. No.: 09/004,406

(22) Filed: Jan. 8, 1998

Related U.S. Application Data

(62) Division of application No. 08/637,640, filed as application No. PCT/US95/12423 on Aug. 23, 1996, now Pat. No. 5,849,541, which is a continuation of application No. 08/148,132, filed on Nov. 2, 1993, now abandoned.

(51) Int. Cl.[7] .............................. C12F 17/06; C12F 19/34; C12N 9/00; C07H 21/04

(52) U.S. Cl. ...................... 435/69.2; 435/91.1; 435/125; 435/183; 435/254.11; 435/254.3; 435/254.5; 435/254.6; 435/320.1; 536/23.2; 536/24.3

(58) Field of Search .................. 435/6, 125, 148, 435/155, 252.3, 254.1, 254.11, 254.3, 254.5, 254.6, 320.1, 256.1, 69.2, 91.1, 183; 536/23.2, 24.3

(56) References Cited

U.S. PATENT DOCUMENTS

| 4,231,938 | 11/1980 | Monaghan et al. | 549/292 |
|---|---|---|---|
| 4,346,227 | 8/1982 | Terahara et al. | 560/119 |
| 5,151,365 | 9/1992 | Dombrowski et al. | 435/256.1 |
| 5,159,104 | 10/1992 | Dabora et al. | 560/119 |
| 5,182,298 | 1/1993 | Helms et al. | 514/455 |
| 5,252,474 | 10/1993 | Gewain et al. | 435/91.1 |
| 5,362,638 | 11/1994 | Dahiya | 435/125 |

FOREIGN PATENT DOCUMENTS 0 556 699 A1   8/1993   (EP) .

OTHER PUBLICATIONS

Buckland, et al., "Production of lovastatin, an inhibitor of cholesterol accumulation in humans", Novel Microbial Products for Medicine and Agriculture, Ch. 19, pp. 161–169, 1989.

Hopwood, et al., "Molecular Genetics of Polyketides and its Comparison to Fatty Acis Biosynthesis", Annu. Rev. Genet., 1990, 24, pp. 37–66.

Moore, et al., "Biosynthesis of the Hypocholesterolemic Agent Mevinolin . . . ", J. Am. Chem. Soc., 1985, 107, pp. 3694–3701.

Endo, et al., "Dihydromonacolin L and Monacolin X, New Metabolites . . . ", The Journal of Antibiotics, vol. XXXVIII, No. 3, pp. 321–327, 1985.

Endo, et al., "Monacolin M, New Inhibitor of Cholesterol Biosynthesis", The Journal of Antibiotics, Dec. 1986, vol. XXXIX, pp. 1670–1673.

Springer, et al., "Terretonin, a Toxic Compound from *Aspergillus terreus*", J. Org. Chem., vol. 44, No. 26, pp. 4852–4854 (1979).

Arai, et al., "Pravastatin Sodium (CS–514) A Novel Cholesterol Lowering Agent . . . ", Sankyo Kenlyusho Vempo, 40, 1–38 (1988).

Drugs of the Future, vol. 12, No. 5, 1987 "Eptastatin Sodium".

Mayorga, et al., "The Developmentally Regulated Aspergillus . . . ", Mol. Gen. Genet., 235(2–3); 205–212 (Nov. 1992).

Leadley, et al., "The Erythromycin–Producing Polyketide Synthase", Biochem. Soc. Trans. 21 (1): 218–222 (Feb. 1993).

Cortes, et al., "An Unusually Large Multifunctional Polypeptide . . . ", Nature, 348: 176–178 (Nov. 1990).

Bevitt, et al., "6–Deoxyerythromolide–B Synthase . . .", Eur. J. Biochem., 204: 39–49 (Feb. 1992).

Beck, et al., "The Multifunctional 6–Methysalicylic Acid Synthase Gene . . . ", Eur. J. Biochem., 192: 487–498 (Dept. 1990).

Hutchinson, et al., "The Genetic and Biochemical Basis of Polyketide Metabolism . . . ", Planta Med. 57(7) (Suppl. 1): 536–543 (Oct. 1991).

*Primary Examiner*—Elizabeth Slobodyansky
(74) *Attorney, Agent, or Firm*—Michael D. Yablonsky; Jack L. Tribble

(57) ABSTRACT

DNA encoding triol polyketide synthase (TPKS) has been isolated, purified and sequenced. Expression vectors comprising TPKS, cells transformed with the expression vectors, and processes employing the transformed cells are provided.

7 Claims, 30 Drawing Sheets

```
CTGCAGTCAA CGGATCACTT ACCATGCTG TCGCCAAAAA TATCCGTGAT AATCCCGCTG    60
GCTTCATTGG CAAGAGGCTT GACGTACTTG GGAGCTTGGG TCTGGAACTG GTTCATAACC  120
ACCTTGGTGA TGAGATGTGC ATCCCTCGTG ACTTCCTTGA ATCCATCGAA TCCGGGAAGA  180
TGAGAGTGAA AGTCCTGATG AGAGCACGAA GATCAGTAAG TCAGGTCCTC ACAGCGGAAG  240
CAGTTGCAAA GAACGGTGGA CTCCTTACCG TGCCCAAGAA CTTGTACATA CAGAGCTCTT  300
TCATCTTGCG AAACTCATCG GCCATAGAGG AGGGAAGAAT GGTGCAGTAC CCAGAGTCGA  360
CTATGAACCG AATGGGCTTA TCATTTGCCG AGAACCAGCT CTCAATCCAT GACGGTGCAT  420
TCGCATCAAA ATCCCGTTTG GCCCTCATGG TCGTCAGTTC CCACCATGTT TTCGGATTGA  480
ACACCGGCAG ATCAGATCTC CGGCCACTCG AGCACAGGTA AAGAAGAAGG CATAGTAGCC  540
CCGCACTGGT AGTGACCAAG GGGCAAACC ACGAGCCATG TTGCTGCGTG TCATTCCAAG   600
CCAGCGACAG AAGGTGGTGC GGCTGTGTGA GCGCGTCGAC AGTCATGGCT AGGAGACCAG  660
GTGTGGTTGA GGGATAAGAT ATCGAGAGTG ATGTGAGCAA AAGATCCGGG AAAGGTCGCG  720
```

| | | | | | |
|---|---|---|---|---|---|
| AAGGAAAGGG | CGTCTCTCTT | ACCAAGAAAG | TCTGTTCCCT | ATCATGCAAT | CACCGCTTGC | 780
| TGTACGGTGG | TGATGATGCT | GGGATGGTGG | TGGGTCCCCA | CCGAATAACG | CCGGACAGCT | 840
| GTTGAAGCCG | AATGACGCCG | GCAGGCCAAA | AGAACCCTAC | CTTCACTTAC | TCAATCGGCG | 900
| CTTCCCCTCC | TATCACCAAA | TCGGATGTAA | ATGGACGGGC | CTTAATAGCG | ACCGGCCGGG | 960
| CCGGGAATCC | CCAAACGTAG | ATAGATAGGC | ATAGACCCGA | AATCTTTGGC | CCGGCATACA | 1020
| TGAGCACAGG | AAGTTTCACG | CGACGGGCGCC | TTTCCTGCCT | CAGCTTCAAT | CCAAGCTCAC | 1080
| GAGTTCTGTC | GCCTCTATCA | GTCGTGCAAT | TGTCCTACTG | CAAACAGCAT | GGCTCAATCT | 1140
| ATGTATCCTA | ATGAGCCTAT | TGTCGTGGTC | GGCAGTGGTT | GTCGCTTCCC | TGGTGACGCC | 1200
| AACACACCCT | CCAAGCTCTG | GGAGCTACTC | CAGCATCCTC | GCGATGTGCA | GAGTCGAATC | 1260
| CCCAAAGAAC | GATTTGACGT | CGACACATTT | TATCACCCGG | ACGGGAAGCA | CCACGGGCGA | 1320
| ACAAATGCAC | CCTACGCCTA | TGTTCTCCAA | GACGATCTGG | GCGCCTTCGA | TGCGGCCTTC | 1380
| TTCAATATCC | AGGCTGGAGA | GGCCGAGAGT | ATGGACCCCC | ATGGACCCCC | GTTGCTGGAG | 1440

```
ACGGTGTACG AGGCCGTAAC GAATGCTGGA ATGCGTATCC AGGATCTGCA GGGAACTTCG    1500

ACTGCTGTTT ACGTCGGGGT GATGACGCAC GACTATGAGA CTGTCTCAAC CCGCGACCTG    1560

GAGAGCATCC CCACCTACTC GGCGACGGGT GTCGCGGTCA GTGTTGCGTC CAACCGCATC    1620

TCGTATTTTT TTGACTGGCA TGGACCAAGT GTAAGTCACC CAATATCGTG TAGCAGTCTA    1680

ATCATGCTCT AACGGACCCG GATGGTTGAA AGATGACGAT CGATACGGCA TGCAGCTCGT    1740

CGTTGGTTGC CGTTCATCTG GCGGGTGCAAC AGCTACGGAC GGGTCAAAGC TCCATGGCAA    1800

TTGCTGCGGG TGCGAATCTG ATTCTGGGGC CGTCCTTGAA AGCAAATTGA    1860

GCATGCTATC CCCCTCGGGT CGATCCCGCA TGTGGGACGC CGGAGCTGAC GGCTATGCCA    1920

GAGGCGTGAG TGTTTCTTGA GCTCGTAGAT GACAGTCCCC ATCGCTGACC GTGATCAGGA    1980

AGCTGTTTGC TCTGTAGTGT TGAAGACATT GAGTCAAGCC TTGCCGGATG GGGACACGAT    2040
```

FIG. 1C

```
TGAATGTGTC ATCCGAGAAA CTGGGGTGAA TCAAGATGGC CGAACGACCG GAATTACGAT    2100

GCCGAACCAT AGTGCTCAGG AGGCACTCAT CAAGGCTACC TACGCCCAGG CTGGCCTTGA    2160

CATCACCAAG GCCGAGGACA GGTGCCAATT CTTCGAGGCT CATGGTCAGC AAAGAGAACC    2220

TGTTCTGTTG GCGCCCTGCA GCTGACATTC GTATGATAGG GACTGGTACT CCGGCCCGGAG   2280

ATCCCCAGGA GGCGGAGGCC ATTGCAACAG CCTTCTTCGG CCACGAGCAG GTAGCACGCA    2340

GCGACGGAAA CGAGAGGGCC CCTCTGTTCG TGGGCAGTGC GAAAACTGTT GTCGGGCACA    2400

CCGAGGGCAC GGCCGGTCTG GCTGGTCTCA TGAAGGCGTC GTTCGCTGTC CGCCATGGGG    2460

TAATCCCCCC CAACCTGCTG TTCGACAAAA TCAGCCCCCG AGTCGCCCCA TTCTATAAAA    2520

ACCTGAGGAT TCCGACAGAA GCTACCCAAT GGCCAGCTCT CCCACCCGGA CAACCGCGCC    2580

GCGCCAGTGT CAACTCCTTT GGTAAGCGAG AGGAACCCTC ACAAGTACTC                2640
```

FIG. 1D

```
GAATTAAATGC TAACTGAACC GCGCCCGATGG ACAGGATTCG GCGGCACGAA TGCGCATGCC  2700
ATTATTGAGG AATACATGGA GCCAGAGCAA AACCAGCTGC GAGTCTCGAA TAATGAGAC    2760
TGCCCACCCA TGACCGGTGT CCTGAGTTTA CCCTTAGTCC TCTCGGCGAA GTCCCAGCGC   2820
TCCTTAAAGA TAATGATGGA GGAGATGCTG CAATTCCTTC AGTCTCACCC CGAGATACAC   2880
TTGCACGACC TCACCTGGTC CTTACTGCGC AAGCGGTCAG TTCTACCCTT CCGCCGGGCT   2940
ATTGTCGGCC ATAGTCATGA AACCATCCGC CGGGCTTTGG AGGATGCCAT CGAGGATGGT   3000
ATTGTGTCGA GCGACTTCAC TACGGAGGTC AGAGGCCAGC CATCGGTGTT GGAATCTTC    3060
ACCGGGCAGG GGGCGCAGTG GCCGGGGGATG TTAAAGAATC TGATAGAGGC ATCGCCATAT  3120
```

FIG.1E

| | | | | |
|---|---|---|---|---|
| GTGCGGAACA | TAGTGAGGGA | GCTGGACGAC | TCCCTGCAGA | GCTTGCCGGA | AAAATACCGG | 3180 |
| CCCTCGTGGA | CGCTACTGA | CCAGTTCATG | CTAGAAGGAG | AGGCCTCCAA | CGTCCAATAT | 3240 |
| GCTACTTTCT | CCCAGCCATT | ATGCTGCGCG | GTGCAAATTG | TCCTGGTCCG | TCTCCTTGAA | 3300 |
| GCCGCGAGAA | TACGATTCAC | GGCTGTGTT | GGACATAGCT | CCGGCGAAAT | TGCTTGCGCC | 3360 |
| TTTGCTGCCG | GGCTCATCAG | TGCCTCGTTG | GCGATTCGGA | TTGCTTACTT | ACGTGGAGTC | 3420 |
| GTCTCGGCAG | GGGGCGCCAG | AGGCACACCG | GGAGCCATGT | TGGCCGCCGG | GATGTCCTTT | 3480 |
| GAGGAAGCAC | AAGAGATCTG | CGAGTTGGAT | GCCTTTGAGG | GCCGCATCTG | CGTGGCTGCC | 3540 |
| AGCAATTCCC | CAGACAGTGT | AACTTTCTCT | GGCGACGCGA | ACGCAATTGA | TCACCTGAAG | 3600 |
| GGCATGTTGG | AGGATGAGTC | CACTTTTGCG | AGACTGCTCA | AGTCGATAC | AGCGTACCAC | 3660 |

FIG.1F

```
TCGCATCATA TGCTTCCATG TGCAGACCCA TATATGCAAG CCCTAGAAGA GTGTGGTTGT    3720
GCTGTTGCCG ATGCAGGTTC CCAGCCGGA AGTGTACCCT GGTATTCGTC CGTGGACGCC    3780
GAGAACAGGC AAATGGCAGC AAGAGACGTG ACCGCCAAGT ACTGGAAAGA TAACTTAGTA    3840
TCTCCGGTGC TATTCTCCCA CGCAGTGCAG CGGGCAGTCG TCACGCACAA GGGCTGAT    3900
ATCGGGATTG AAGTGGGCTG TCACCCAGCT CTCAAGAGCC CATGCGTCGC CACCATCAAG    3960
GATGTCCTAT CTGGGGTTGA CCTGGCGTAT ACAGGTTGCT TGGAGCGGAGG AAAGAATGAT    4020
CTCGATTCAT TCTCTCGAGC ACTGGCATAT CTCTGGGAAA GGTTTGGTGC CTCCAGTTTC    4080
GATGCGGACG AGTTCATGCG TGCAGTCGCG CCTGATCGGC CCTGTATGAG TGTGTCGAAG    4140
CTCCTACCGG CCTATCCATG GGACCGCTCT CGTCGCTACT GGGTGGAATC CCGAGCAACT    4200
```

FIG.1G

```
CGCCACCATC TTCGAGGGCC CAAGCCCCAT CTTCTATTAG GAAAGCTCTC CGAATACAGC  4260
ACTCCGCTAA GCTTCCAGTG GCTGAATTTT GTGCGCCCAC GAGACATTGA ATGGCTTGAT  4320
GGACATGCAT TGCAAGGCCA GACTGTCTTC CCTGCGGCCG GCTATATCGT CATGGCAATG  4380
GAAGCAGCCT TAATGATTGC TGGCACCCAC GCAAAGCAGG TCAAGTTACT GGAGATCTTG  4440
GATATGAGCA TTGACAAGGC GGTGATATTT GACGACGAAG ACAGCTTGGT TGAGCTCAAC  4500
CTGACAGCTG ACGTGTCTCG CAACGCCGGC GAAGCAGGTT CAATGACCAT AAGCTTCAAG  4560
ATCGATTCCT GTCTATCGAA GGAGGGTAAC CTATCCCTAT CAGCCAAGGG CCAACTGGCC  4620
CTAACGATAG AAGATGTCAA TCCCAGGACG ACTTCCGCTA GCGACCAGCA CCATCTTCCC  4680
CCGCCAGAAG AGGAACATCC TCATATGAAC CGTGTCAACA TCAATGCTTT CTACCACGAG  4740
CTGGGGTTGA TGGGTACAA CTACAGTAAG GACTTCCGGC GTCTCCATAA CATGCAACGA  4800
```

FIG.1H

```
GCAGATCTTC GAGCCAGCGG CACCTTAGAC TTCATTCCTC TGATGGACGA GGGTAATGGC   4860
TGTCCTCTCC TGCTGCATCC TGCATCATTG GACGTCGCCT TCCAGACTGT CATCGGCGCA   4920
TACTCCTCCC CAGGTGATCG GCGTCTACGC TGTCTGTATG TACCCACTCA CGTTGATCGC   4980
ATCACACTTG TCCATCCCT  TTGCCTGGCA ACGGCTGAGT CCGGATGCGA GAAGGTTGCC   5040
TTCAATACTA TCAATACGTA CGACAAGGGA GACTACTTGA GCGGTGACAT TGTGGTGTTT   5100
GACGCGGAGC AGACCACCCT GTTCCAGGTT GAAAATATTA CTTTTAAGCC CTTTTCACCC   5160
CCGGATGCTT CAACTGACCA TGCGATGTTT GCCCGATGGA GCTGGGGTCC GTTGACTCCG   5220
GACTCGCTGC TGGATAACCC GGAGTATTGG GCCACCCGCG AGGACAAGGA GGCGATTCCT   5280
```

FIG. 1I

| | | | |
|---|---|---|---|
| ATTATCGAAC | GCATCGTCTA | CTTCTATATC | CGATCGTTCC | TCAGTCAGCT | TACGCTGGAG | 5340 |
| GAGCGCCAGC | AGGCAGCCTT | CCATTGCAG | AAGCAGATCG | AGTGGCTCGA | ACAAGTCCTG | 5400 |
| GCCAGCGCCA | AGGAGGGTCG | TCACCTATGG | TACGACCCCG | GGTGGGAGAA | TGATACTGAG | 5460 |
| GCCCAGATTG | AGCACCTTTG | TACTGCTAAC | TCCTACCACC | CTCATGTTCG | CCTGGTTCAG | 5520 |
| CGAGTCGGCC | AACACCTGCT | CCCCACCGTA | CGATCGAACG | GCAACCCATT | CGACCTTCTG | 5580 |
| GACCACGATG | GGCTCCTGAC | GGAGTTCTAT | ACCAACACAC | TCAGCTTCGG | ACCCGCACTA | 5640 |
| CACTACGCCC | GGGAATTGGT | GGCGCAGATC | GCCCATCGCT | ATCAGTCAAT | GGATATTCTG | 5700 |
| GAGATTGGAG | CAGGGACCCG | CGGCGCTACC | AAGTACGTGT | TGGCCACGCC | CCAGCTGGGG | 5760 |
| TTCAACAGCT | ACACATACAC | CGATATCTCC | ACCGGATTCT | TCGAGCAAGC | GCGGGAGCAA | 5820 |
| TTTGCCCCCT | TCGAGGACCG | GATGGTGTTT | GAACCCCTCG | ATATCCGCCG | CAGTCCCGCC | 5880 |

FIG.1J

| | | | | |
|---|---|---|---|---|
| GAGCAGGGCT | TCGAGCCGCA | TGCCTATGAT | CTGATCATTG | CCTCCAATGT | GCTACATGCG | 5940 |
| ACACCCGACC | TAGAGAAAAC | CATGGCTCAC | GCCCGCTCTC | TGCTCAAGCC | TGGAGGCCAG | 6000 |
| ATGGTTATTC | TGGAGATTAC | CCACAAAGAA | CACACACGGC | TCGGGTTTAT | CTTTGGTCTG | 6060 |
| TTCGCCGACT | GGTGGGCTGG | GGTGGATGAT | GGTCGCTGCA | CTGAGCCGTT | TGTCTCGTTC | 6120 |
| GACCGCTGGG | ATGCGATCCT | AAAGCGTGTC | GGGTTTTCCG | GTGTGGACAG | TCGCACCACG | 6180 |
| GATCGGGACG | CAAATCTATT | CCCGACCTCT | GTGTTTAGTA | CCCATGCAAT | TGACGCCACC | 6240 |
| GTGGAGTACT | TAGACGCGCC | GCTTGCCAGC | AGCGGCACCG | TCAAGGACTC | TTACCCTCCC | 6300 |
| TTGGTGGTGG | TAGGAGGGCA | GACCCCCCAA | TCTCAGCGTC | TCCTGAACGA | TATAAAGCG | 6360 |
| ATCATGCCTC | CTCGTCCGCT | CCAGACATAC | AAGCGCCTCG | TGGATTTGCT | AGACGCGGAG | 6420 |
| GAGCTGCCGA | TGAAGTCCAC | GTTGTCATG | CTCACGGAGC | TGGACGAGGA | ATTATTCGCC | 6480 |

FIG. 1K

```
GGGCTCACTG AAGAGACCTT CGAGGCAACC AAGCTGCTGC TCACGTACGC CAGCAATACG   6540
GTCTGGCTGA CAGAAAATGC CTGGGTCCAA CATCCTCACC AGGCGAGCAC GATCGGCATG   6600
CTACGCTCCA TCCGCCGGGA GCATCCTGAC TTGGGAGTTC ATGTTCTGGA CGTCGACGCG   6660
GTTGAAACCT TCGATGCAAC CTTCCTGGTT GAACAGGTGC TTCGGCTTGA GGAGCATACG   6720
GATGAGCTGG CCAGTTCAAC TACATGGACT CAAGAACCCG AGGTCTCCTG GTGTAAAGGC   6780
CGCCCGTGGA TTCCTCGTCT GAAGGCGGAT CTGGCTCGCA GAACTCCTCG              6840
CGCCGTCCCA TATACGAGAT GATCGATTCG TCGCGGGCTC CCGTGGCATT ACAGACGGCT   6900
CGGGATTCAT CATCCTACTT CTTGGAGTCC GCTGAAACCT GGTTTGTGCC TGAGAGTGTT   6960
CAGCAGATGG AAACAAAGAC GATCTATGTC CACTTTAGCT GTCCCCATGC GCTTAGGGTC   7020
```

FIG. 1L

```
GGACAGCTCG GGTTTTCTA TCTTGTGCAG GGTCACGTCC AGGAGGGCAA TCGGAAGTG    7080
CCCGTCGTGG CCTTAGCAGA GCGTAACGCA TCCATTGTGC ACGTTCGTCC CGATTATATA  7140
TATACTGAGG CAGATAACAA TCTGTCTGAG GGTGGTGGCA GCCTTATGGT AACCGTCCTC  7200
GCCGCGGCGG TGTTGGCGGA GACGGTGATC AGTACCGCCA AGTGCCTGGG GGTAACTGAC  7260
TCAATCCTCG TTCTGAATCC CCCCAGCATA TGTGGGCAGA TGTTGCTCCA TGCTGGTGAA  7320
GAGATCGGTC TTCAAGTTCA TCTGGCCACC ACTTCTGGCA ACAGGAGTTC GGTTTCTGCT  7380
GGAGACGCCA AGTCCTGGCT AACATTGCAT GCTCGCGACA CGGACTGGCA CCTGCGACGG  7440
GTACTGCCCC GGGGTGTCCA GCTTTAGTC GACTTATCAG CCGACCAGAG CTGTGAAGGT   7500
TTGACTCAGA GGATGATGAA AGTTCTGATG CCTGGCTGTG CCCATTACCG TGCGGCAGAC   7560
```

FIG. 1M

| | | | | |
|---|---|---|---|---|
| CTGTTCACAG | ACACCGTTTC | CACTGAATTG | CATAGCGGAT | CGCGGCATCA | AGCTTCACTG | 7620 |
| CCCGCCGCAT | ATGGGAGCA | TGTGGTATCC | TTAGCCCGCC | AGGGACTTCC | TAGTGTCAGC | 7680 |
| GAGGGGTGGG | AGGTGATGCC | GTGCACTCAA | TTTGCAGCGC | ATGCCGACAA | GACGCGCCCG | 7740 |
| GATCTCTCGA | CAGTTATTTC | CTGGCCCCGG | GAGTCGGACG | AGGCTACGCT | TCCTACCAGG | 7800 |
| GTTCGCTCCA | TTGACGCTGA | GACCCTCTTT | GCGGCCCGACA | AAACATATCT | CCTGGTCGGA | 7860 |
| CTGACTGGAG | ATCTTGGACG | CGTTGGATGG | TCCAGCATGG | GCCTGCCAC | 7920 |
| ATTGTACTTA | CGAGCAGAAA | TCCGCAGGTG | AACCCCAAGT | GGCTGGCGCA | TGTTGAAGAA | 7980 |
| CTGGGTGGTC | GAGTCACTGT | TCTTTCCATG | TAAGAGGAGT | CCTTCCTTCT | GCAATTCCTC | 8040 |
| CTTATGATCC | CGACTAACGC | AGCTGGCTTC | AGGGACGTGA | CAAGCCAAAA | CTCAGTGGAA | 8100 |
| GCTGGCCTGG | CTAAACTCAA | GGATCTGCAT | CTGCCACCAG | TGGGGGGTAT | TGCCTTTGGC | 8160 |

FIG. 1N

| | | | | |
|---|---|---|---|---|
| CCTCTGGTTC | TGCAGGATGT | GATGCTAAAT | AATATGGAAC | TGCCAATGAT | GGAGATGGTG | 8220
| CTCAACCCCA | AGGTCGAAGG | CGTCCGCATC | CTGCACGAGA | AGTTCTCCGA | TCCGACCAGT | 8280
| AGCAACCCTC | TCGACTTCTT | CGTGATGTTC | TCCTCGATTG | TGGCCGTCAT | GGGCAACCCG | 8340
| GGTCAGGCTA | ACTACAGTGC | GGCTAACTGC | TACCTTCAAG | CGCTGGGCCA | GCAGCGAGTT | 8400
| GCATCCGGAT | TAGCAGTACG | TTTTCACTCC | ATCCTTTGCT | AAACACTCCT | ATGGGCCTTT | 8460
| ACTAAACCGG | GCAGGCGTCC | ACCATCGACA | TCGGTGCCGT | GTACGGCGTT | GGGTTCGTCA | 8520
| CTCGGGCGGA | GCTGGAGGAG | GACTTTAATG | CAATTCGGTT | CATGTTCGAT | TCGGTTGAGG | 8580
| AACATGAACT | GCATACACTG | TTTGCTGAGG | CAGTGGTGGC | CGGTCGACGA | GCCGTGCACC | 8640
| AGCAAGAGCA | GCAGCGGAAG | TTCGCCGACAG | TGCTCGACAT | GGCTGATCTG | GAACTGACAA | 8700

FIG. 10

| | | | | | 8760 |
|---|---|---|---|---|---|
| CCGGAATTCC | GCCCCTGGAT | CCAGCCCTCA | AAGATCGGAT | CACCTTCTTC | GACGACCCCC |
| GCATAGGCAA | CTTAAAAATT | CCGGAGTACC | GAGGGGCCAA | AGCAGGCGAA | GGGGCAGCCG 8820 |
| GCTCCAAGGG | CTCGGTCAAA | GAACAGCTCT | TGCAGGCGAC | GAACCTGGAC | CAGGTCCGTC 8880 |
| AGATCGTCAT | CGGTAAGTTG | GGGAATATTC | TCCCCTTCCT | CACTCAGCGG 8940 |
| ACTGGAGATT | AACCGCTTCT | TTTCCTTTGG | CAGATGGACT | CTCCGCGAAG | CTGCAGGTGA 9000 |
| CCCTGCAGAT | CCCCGATGGG | GAAAGCGTGC | ATCCCACCAT | CCACTAATC | GATCAGGGGG 9060 |
| TGGACTCTCT | GGGGCGGGTC | ACCGTGGGAA | CCTGGTTCTC | CAAGCAGCTG | TACCTTGATT 9120 |
| TGCCACTCCT | GAAAGTGCTT | GGGGTGCTT | CGATCACCGA | TCTCGCTAAT | GAGGCTGCTG 9180 |
| CGGGATTGCC | ACCTAGCTCC | ATTCCCCTCG | TCGCAGCCAC | CGACGGGGGT | GCAGAGAGCA 9240 |
| CTGACAATAC | TTCCGAGAAT | GAAGTTTCGG | GACGCGAGGA | TACTGACCTT | AGTGCCGCCG 9300 |

FIG. 1P

| | | | | |
|---|---|---|---|---|
| CCACCATCAC | TGAGCCCTCG | TCTGCCGACG | AAGACGATAC | GGAGCCGGGC | GACGAGGACG | 9360
| TCCCGCGGTC | CCACCATCCA | CTGTCTCTCG | GGCAAGAATA | CTCCTGGAGA | ATCCAGCAGG | 9420
| GAGCCGAAGA | CCCCACCGTC | TTTAACAACA | CCATTGGTAT | GTTCATGAAG | GGCTCTATTG | 9480
| ACCTTAAACG | GCTGTACAAG | GCGTTGAGAG | CGGTCTTGCG | CCGCCACGAG | ATCTTCCGCA | 9540
| CGGGGTTTGC | CAACGTGGAT | GAGAACGGGA | TGGCCCAGCT | GGTGTTTGGT | CAAACCAAAA | 9600
| ACAAAGTCCA | GACCATCCAA | CCTGCCGCAG | GAGCCGGGGC | CGAAGAGGGC | TACCGACAAC | 9660
| TGGTGCAGAC | ACGGTATAAC | GAGACACCTT | GCGGCTGGTG | GACTTCTTCT | 9720
| GGGGCCAGGA | CGACCATCTG | CTGGTTGTGG | CTTACCACCG | ACTCGTCGGG | GATGGATCTA | 9780
| CTACAGAGAA | CATCTTCGTC | GAAGCGGGCC | AGCTCTACGA | CGGCACGTCG | CTAAGTCCAC | 9840

FIG. 1Q

```
ATGTCCCTCA GTTGCGGAC  CTGGCGGCAC GGCAACGCGC AATGCTCGAG GATGGGAGAA    9900

TGGAGGAGGA TCTCGCGTAC TGGAAGAAAA TGCATTACCG ACCGTCCTCA ATTCCAGTGC    9960

TCCCACTGAT GCGGCCCCTG GTAGGTAACA GTAGCAGGTC CGATACTCCA AATTTCCAGC   10020

ACTGTGGACC CTGGCAGCAG CACGAAGCCG TGGCGCGACT TGATCCGATG GTGGCCTTCC   10080

GCATCAAGGA GCGCAGTCGC AAGCACAAGG CGACGCCGAT GCAGTTCTAT CTGGCGGCGT   10140

ATCAGGTGCT GTTGGCGGC  CTCACCGACA GCACCGATCT CACCGTGGGC CTCGCCGACA   10200

CCAACCGTGC GACTGTCGAC GAGATGGCGG CCATGGGGTT CTTCGCCAAC CTCCTTCCCC   10260

TGCGCTTCCG GGATTTCCGC CCCCATATAA CGTTTGGCGA GCACCTTATC GCCACCCGTG   10320

ACCTGGTGCG TGAGGCCTTG CAGCACGCCC GCCTGCCCTA CGGCGTCCTC CTCGATCAAC   10380
```

FIG. 1R

```
TGGGGCTGGA GGTCCCGGTC CCGACCAGCA ATCAACCTGC GCCTTTGTTC CAGGCCGTCT    10440
TCGATTACAA GCAGGGCCAG GCGGAAAGTG GAACGATTGG GGGTGCCAAG ATAACCGAGG    10500
TGATTGCCAC GCGCGAGCGC ACCCCTTACG ATGTCGTGCT GGAGATGTCG GATGATCCCA    10560
CCAAGGATCC GCTGCTCACG GCCAAGTTAC AGAGTTCCCG CTACCGAGCT CACCACCCTC    10620
AAGCCTTCTT GGAGAGCTAC ATGTCCCTTC TCTCTATGTT CTCGATGAAT CCCGCCCTGA    10680
AGCTGGCATG ATGGCGCAAA CATAGAACAT GATAGCGCAG CAGGGACGAT GTAGATAGAG    10740
CTTTGCTTCT GCGGGTGGAT CTATAATATA GTATATATAA ATATGGTGAG CCGAACGAAG    10800
AGGGGGAAT  GCCACAATTA TTTACTGTTT TGCGCCCGTAC ACGAGGAGAA GACGTCCAGA    10860
ACAACATAAA TATATCACTC TAGTGAGACA CCATATATTC GGAGAGACTA TAAAAATATA    10920
CATCTACTCC AATGTCTGGG CCGTCACACA CAGCTTACGA AAACGATTAA TGACCTCCAA    10980
```

FIG.1S

```
CACGTCGCGC GGTCGATTGG GAAACTGATG CTGCCCAGCA AACTCCAATA CCTGCGCCTC    11040
TCGGGGGAG  AAATGGCGCG CCACCAGCAT CTTCGATCCT GCGAGGCAA  AATCATGCG     11100
ACCCTGCAGA TGTAATGTCG GTATCCGAAT GACCAGTTCC TCCTGCCACT CGGTATCTTT    11160
GCTGTCGTTG TCGTCGTCAT GGTTCTTCAT CATTCGTTCC TCATATACTG GCTTGCCTCG    11220
TCTTGATACC AGGGACAGAT CAACAGCGCA ACACTCATCC GGGGCAACCA GGGCAGGTGA    11280
CCCATCTGCT GCTGCCAGAG GAGCAAGGTC GTCACCAGGG CACCTTCGGA GAAACCGATA    11340
GCACCCACGA TAGGGATGTG GGGGTGTTGA GTCTGCCAGT CGACAATGGT GCGGCGGATG    11400
GGGTCGTGGA CGGCGGCGAG GCGTTCGCTC ACGGAGGGTC CATTATGATT GTTGTCGCTG    11460
CTGCTTTCAA ACCAGGAGTA ATATGGCCCT AGTCGGGCGA AGACGGGGAG AATCCCAGGC    11520
CCTGCAGAGG AAGGGAACGG AGCTGTCACG TAGACCAATT C                        11561
```

| | | | | | |
|---|---|---|---|---|---|
| MAQSMYPNEP | IVVVGSGCRF | PGDANTPSKL | WELLQHPRDV | QSRIPKERFD | 50 |
| VDTFYHPDGK | HHGRTNAPYA | YVLQDDLGAF | DAAFFNIQAG | EAESMDPQHR | 100 |
| LLLETVYEAV | TNAGMRIQDL | QGTSTAVYVG | VMIHDYETVS | TRDLESIPTY | 150 |
| SATGVAVSVA | SNRISYFFDW | HGPSMTTDTA | CSSSLVAVHL | AVQQLRTGQS | 200 |
| SMAIAAGANL | ILGPMTFVLE | SKLSMLSPSG | RSRMWDAGAD | GYARGEAVCS | 250 |
| VVLKTLSQAL | RDGDTTECVI | RETGVNQDGR | T<u>TGTTMPKHS</u> | AQEALIKATY | 300 |
| AQAGLDITKA | EDRCQFFEAH | GTGTPAGDPQ | EAEAIATAFF | GHEQVAPGGG | 350 |
| NERAPLFVGS | AKTVVGHTEG | TAGLAGLMKA | SFAVRHGVIP | PNLLFIKISP | 400 |
| RVAPFYKNLR | IPTEATQWPA | LPPGQPRRAS | VNSFGFGGIN | AHAIIEEYME | 450 |
| PEQNQLRVSN | NEDCPPMTGV | LSLPLVLSAK | SQRSLKIMME | EMLQFLQSHP | 500 |
| EIHLHDETWS | LLRKRSVLPF | RRAIVGHSHE | TEAAALEDAI | EDGIVSSDIT | 550 |
| TEVRGQPSVL | GIFTGQGAQW | PGMLKNLIEA | SPVYRNIVRE | LDDSLQSLPE | 600 |
| KYRPSWTLLD | QFMLEGEASN | VQYATFSQPL | CCAVQIVLVR | LLEAARIRFT | 650 |
| AVVGHSSGEI | ACAFAAGLIS | ASLAIRIAYL | RGVVSAGGAR | GTPGAMLAAG | 700 |
| MSFEEAQEIC | ELDAFEGRIC | VAASNSPDSV | TFSGDANAID | HLKGMLEDES | 750 |
| TFARLLKVDT | AYHSHHMLPC | ADPYMQALEE | CGCAVADAGS | PAGSVPWYSS | 800 |
| VDAENRQMAA | RDVTAKYWKD | NLVSPVLFSH | AVQRAVVIHK | ALDIGIEVGC | 850 |
| HPALKSPCVA | TIKDVLSGVD | LAYTGCLERG | KNDLDSFSRA | LAYLWERFGA | 900 |
| SSFDADEFMR | AVAPDRPQMS | VSKLLPAYPW | DRSRRYWVES | RATRHHLPGP | 950 |

| | | | | | |
|---|---|---|---|---|---|
| KPHLLLGKLS | EYSTPLSFQW | LNFVRPRDIE | WLDGHALQGQ | TVFPAAGYTV | 1000 |
| MAMEAALMIA | GTHAKQVKLL | ETLDMSIDKA | VIFDDEDSLV | ELNLTADVSR | 1050 |
| NAGEAGSMTI | SFKIDSCLSK | EGNLSLSAKG | QLALTIEDVN | PRTTSASDQH | 1100 |
| HLPPPEEEHP | HMNRVNINAF | YHELGLMGYN | YSKDFRRLHN | MQRADLRASG | 1150 |
| TLDFIPLMDE | GNGCPLLLHP | ASLDVAFQTV | IGAYSSPGDR | RLRCLYVPTH | 1200 |
| VDRITLVPSL | CLATAESGCE | KVAFNTTNTY | DKGDYLSGDI | VVFDAEQTTL | 1250 |
| FQVENTTFKP | FSPPDASTDH | AMFARWSWGP | LTPDSLLDNP | EYWATAQDKE | 1300 |
| AIPIIERIVY | FYIRSFLSQL | TLEERQQAAF | HLQKQIEWLE | QVLASAKEGR | 1350 |
| HLWYDPGWEN | DTEAQIEHLC | TANSYHPHVR | LVQRVGQHLL | PTVRSNGNPF | 1400 |
| DLLDHDGLLT | EFYTNTLSFG | PALHYARELV | AQIAHRYQSM | DILEIGAGTG | 1450 |
| GATKYVLATP | QLGFNSYTYT | DISTGFFEQA | REQFAPFEDR | MVFEPLDIRR | 1500 |
| SPAEQGFEPH | AYDLIIASWV | LHATPDLEKT | MAHARSLLKP | GGQMVILETT | 1550 |
| HKEHTRLGFI | FGLFADWWAG | VDDGRCTEPF | VSFDRWDAIL | KRVGFSGVDS | 1600 |
| RTTDRDANLF | PTSVFSTHAI | DATVEYLDAP | LASSGTVKDS | YPPLVVVGGQ | 1650 |
| TPQSQRLLND | IKAIMPPRPL | QTYKRLVDLL | DAEELPMKST | FVMLTELDEE | 1700 |
| LFAGLTEETF | EATKLLLTYA | SNTVWLTENA | WVQHPHQAST | IGMLRSIRRE | 1750 |
| HPDLGVHVLD | VDAVETFDAT | FLVEQVLRLE | EHTDELASST | TWTQEPEVSW | 1800 |
| CKGRPWIPRL | MRDLARNNRM | NSSRRPIYEM | IDSSRAPVAL | QTARDSSSYF | 1850 |
| LESAETWFVP | ESVQQMETKT | IYVHFSCPHA | LRVGQLGFFY | LVQGHVQEGN | 1900 |
| REVPVVALAE | RNASIVHVRP | DYTYTEADNN | LSEGGGSLMV | TVLAAAVLAE | 1950 |

FIG.2B

```
              10         20         30         40         50
         1234567890 1234567890 1234567890 1234567890 1234567890
         TVISTAMCLG VIDSILVLNP PSICGQMLLH AGEEIGLQVH LATTSGNRSS  2000

VSAGDAKSAL TLHARDTDWH LRRVLPRGVQ ALVDLSADQS CEGLTQRMMK  2050

VIMPGCAHYR AADLFTDTVS TELHSGSRHQ ASLPAAYWEH VVSLARQGLP  2100

SVSEGWEVMP CTQFAAHADK TRPDLSTVIS WPRESDEATL PTRVRSIDAE  2150

TLFAADKTYL LVGLTGDLGR SLGRWWVQHG ACHIVLTSRN PQVNPKWLAH  2200

VEELGGRVTV LSMDVTSQNS VEAGLAKLKD LHLPPVGGIA FGPLVLQQVM  2250

LNNMELPMME MVLNPKVEGV RILHEKFSDP TSSNPLDFFV MFSSIVAVMG  2300

NPGQANYSAA NCYLQALAQQ RVASGLAAST IDIGAVYGVG FVTRAELEED  2350

FNAIRFMFDS VEEHELHTLF AEAVVAGRRA VHQQEQQRKF ATVLDMADLE  2400

LTTGIPPLDP ALKDRITFFD DPRIGNLKIP EYRGAKAGEG AAGSKGSVKE  2450

QLLQATNLDQ VRQIVIDGLS AKLQVTLQIP DGESVHPTIP LIDQGVDSLG  2500

AVTVGTWFSK QLYLDLPLLK VLGGASITDL ANEAAARLPP SSIPLVAATD  2550

GGAESTDNTS ENEVSGREDT DLSAAATTTE PSSADEDDTE PGDEDVPRSH  2600

HPLSLGQEYS WRIQQGAEDP TVFNNTIGMF MKGSIDLKRL YKALRAVLRR  2650

HEIFRTGFAN VDENGMAQLV FGQTKNKVQT IQVSDRAGAE EGYRQLVQTR  2700

YNPAAGDTLR LVDFFWGQDD HLLVVAYHRL VGDGSTTENI FVEAGQLYDG  2750

TSLSPHVPQF ADLAARQRAM LEDGRMEEDL AYWKKMHYRP SSIPVLPLMR  2800

PLVGNSSRSD TRNFQHCGPW QQHEAVARLD RMVAFRIKER SRKHKATPMQ  2850

FYLAAYQVLL ARLTDSTDLT VGLADINRAT VDEMAAMGFF ANLLPLRFRD  2900

FRPHITFGEH LIATRDLVRE ALQHARVPYG VLLDQLGLEV PVPTSNQPAP  2950

LFQAVFDYKQ GQAESGTIGG AKITEVIATR ERTPYDVVLE MSDDPTKDPL  3000

LTAKLQSSRY EAHHPQAFLE SYMSLLSMFS MNPALKLA               3038
```

FIG.2C

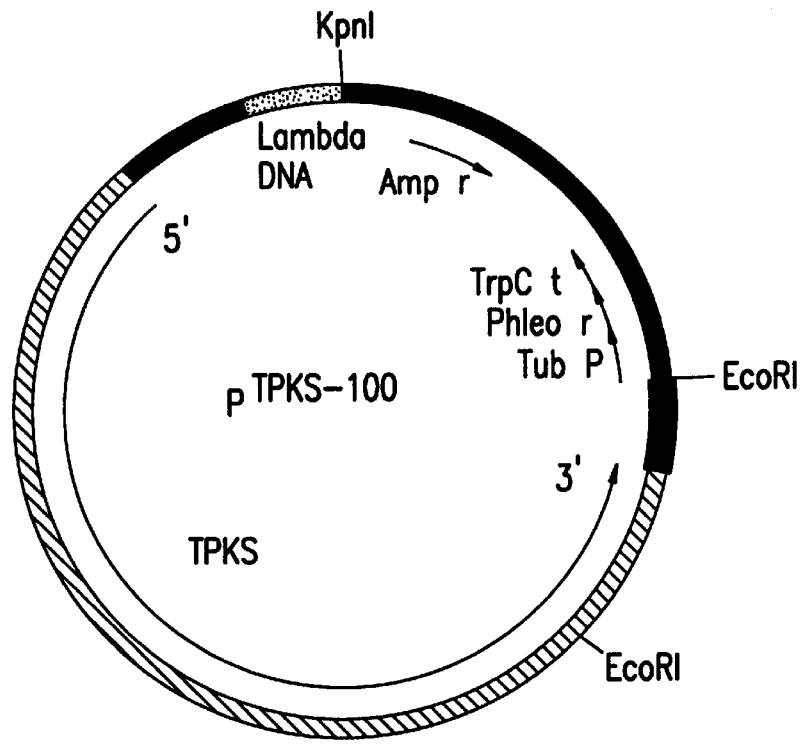
ASPERGILLUS TERREUS DNA:
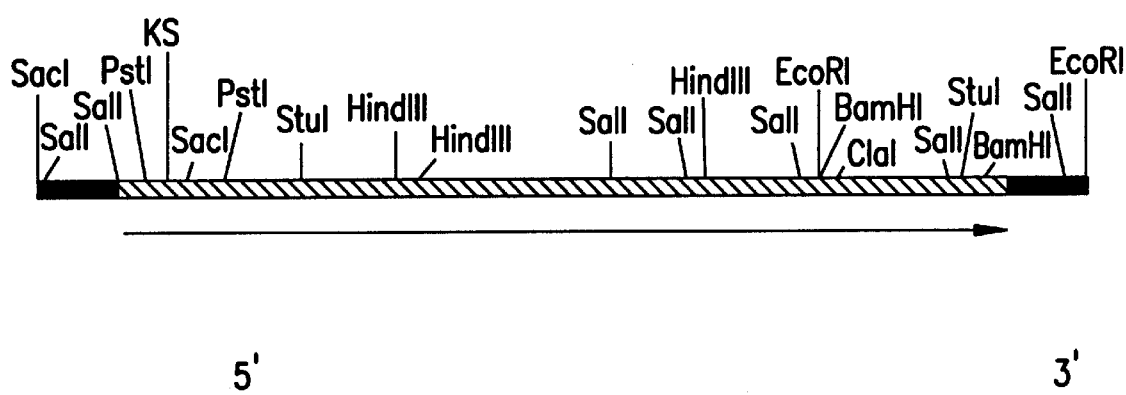
FIG.3

KETO ACYLSYNTHASE ALIGNMENT

```
FAS_RATF    (130-229)    YSMVGCQRAM MANRLSFFFD FKGPSIALDT ACSSSLLALQ NAYQAIRSGE
TRIOL PKS   (150-249)    YSATGVAVSV ASNRISYFFD WHGPSMTIDT ACSSSLVAVH LAVQQLRTGQ
MSAS_PENPA  (173-272)    WMGIGTAYCG VPNRISYHLN LMGPSTAVDA ACASSLVAIH HCVQAIRLGE

Consensus                .......G.. .......... ..NR.S.... .GPS...D.. AC.SSL.A..   ...Q..R.G.
```

ACETYL/MALONYL TRANSFERASE ALIGNMENT

```
MSAS_PENPA  (621-671)    SDRVQILTYV MQIGLSALLQ SNGITPQAVI GHSVGEIAAS VVAGALSPAE
FAS_RATF    (553-603)    F--V-SL-IA IQIALIDLLT SMGLKPDGII GHSLGEVACG YADGCLSQRE
TRIOL PKS   (626-676)    F--SQPLCCA VQIVLVRLLE AARIRFTAVV GHSSGEIACA FAAGLISASL

Consensus                .......... ......QI.L ..LL...... .......... GHS.GE.A..   ...G...S...
```

DEHYDRATASE ALIGNMENT

```
MSAS_PENPA  (943-982)    YTTRLDNDTK PFPGSHPLHG TEIVPAAGLI NTFLKGTGGQ
FAS_RATF    (863-902)    NIDASSESSD HYLVDHCIDG RVLFPGTGYL YLVWK-TLAR S
TRIOL PKS   (970-1010)   WLNFVRPRDI EWLDGHALQG QTVFPAAGYI VMAMEAALMI A

Consensus                .......... ......H..G ......P.G. ..........
```

FIG. 5

ENOYL REDUCTASE ALIGNMENT

```
TRIOL_PKS  (1903-1950)  VPVVALAERN ASIVHVRPDY IYTEADNNLS EGGGSLMVTV LAAAVLAE
FAS_RATF   (1642-1691)  VPVVYTAYY  SLVVRGRIQH GETVLIHSGS GGVGQAAISI ALSLGCRVFT
SU4 ER                  VPIAYTTAHY ALHDLAGLRA GQSVLIHAAA GGVGMAAVAL ARRAG-LAEV

Consensus               VP........ .......... .......... .G.G...... ........
```

KETO REDUCTASE ALIGNMENT

```
TRIOL_PKS   (2141-2196)  PTRVRSIDAE TLFAADKTYL LVGLTGDLGR SLGRWMVQHG ACHIVLTSRN
MSAS_PENPA  (1398-1451)  LP-ASEG-PR LLPRPEGTYL ITGGLGVLGL EVADFLVEKG ARRLLLISRR
FAS_RATF    (1864-1921)  PTLISAI-SK TFCPEHKSYI ITGGLGGFGL ELARWLVLRG AQRLVLTSRS

Consensus                .......... .......Y.. .G..G.G... .......... V..G.A....L.SR.
```

ACYL CARRIER PROTEIN ALIGNMENT

```
TRIOL_PKS   (2461-2548)  VRQIVIDGLS AKLQVTLQIP DGESVHPTIP LIDQGVDSLG AVTVGTWFSK
FAS_RATF    (2114-2201)  GDGEAQRDLV KAVAHILGIR DLAGINLDSS LADLGLDSLM GVEVRQILER
MSAS_PENPA  (1697-1758)  -KAYLDEKIR GCVAKVLQMT A-EDVDSKAA LADLGVDSVM TVTLRRQLQ-

Consensus                .......... .......L.. .......... L.D.G.DS.. V.........
```

ALCOHOL DEHYDROGENASE: STCAVFGLGGVGLSVIMGCKAA — β — TTTTT — α (14aa) — R — 22aa — K

RAT FAS-ER: TVLIHSGSGGVGQAAISIALSL — β — TTTTT — α (14aa) — R — 23aa — K

TPKS-ER: YIYTEADNNLSEGGGSLMVTVL — β — TTTTTTTT — 20aa — K

TPKS-KR: TYLLVGLTGDLGRSLGRWMVQH — β — TTTTTTTT — 20aa — K

MSAS-KR: TYLITGGLGVLGLEVADFLVEK — β — TTTT — α (14aa) — R — 20aa — R

RAT FAS KR: SYIITGGLGGFGLELARWLVLR — β — TTTTTT — α (14aa) — R — 20aa — R

| Potential SAM Binding Region in Methyl Transferase | |
|---|---|
| Consensus | △△D/E△GXGXGX△XXX△△⋎/P |
| TPKS (1444) | I L E I GAGTGG A TKY V L P |

△ = hydrophobic A.A.
X = any A.A.
⋎ = charged A.A.

FIG. 8

DNA ENCODING TRIOL POLYKETIDE SYNTHASE

CROSS-RELATED TO OTHER APPLICATIONS

This is a Divisional Application of U.S. application Ser. No. 08/637,640, filed Aug. 23, 1996, now U.S. Pat. No. 5,849,541, which is both a National Stage Application of PCT/US95/12423, filed Oct. 28, 1994 and a continuation of U.S. application Ser. No. 08/148,132, filed Nov. 2, 1993, now abandoned.

BACKGROUND OF THE INVENTION

Hyperchlosterolemia is known to be one of the prime risk factors for ischemic cardiovascular diseases such as arteriosclerosis. Cholesterol and other lipids are transported in body fluids by lipoproteins of varying density. The two lipoproteins carrying the majority of cholesterol in the blood are low-density lipoproteins (LDL) and high-density lipoproteins (HDL). The role of LDL is to transport cholesterol to peripheral cells outside the liver. LDL-receptors on a cell plasma membrane bind LDL and allow entry of cholesterol into the cell. HDL may scavenge cholesterol in the tissues for transport to the liver and eventual catabolism. LDL levels are positively correlated with the risk of coronary artery disease while HDL levels are negatively related, and the ratio of LDL-cholesterol to HDL-cholesterol has been reported to be the best predictor of coronary artery disease. Thus substances which effectuate mechanisms for lowering LDL-cholesterol may serve as effective antihypercholesterolemic agents.

Mevacor® (lovastatin; mevinolin) and ZOCOR® (simvastatin), now commercially available, are two of a group of very active antihypercholesterolemic agents that function by inhibiting the enzyme HMG-CoA reductase. Lovastatin and related compounds inhibit cholesterol synthesis by inhibiting the rate-limiting step in cellular cholesterol biosynthesis, namely the conversion of hydroxymethyl-glutarylcoenzyme A (HMG-CoA) into mevalonate by HMG-CoA reductase [3.7–9.12]. HMG-CoA reductase inhibitors act through cellular homeostatic mechanisms to increase LDL receptors with a consequent reduction in LDL-cholesterol and a resultant therapeutic antihypercholesterolemic effect. The HMG-CoA reductase inhibitors within this invention include, but are not limited to compactin (ML-236B), lovastatin, simvastatin, pravastatin, fluvastatin and mevastatin.

Many HMG-CoA reductase inhibitors are synthesized by microorganisms. The general biosynthetic pathway of the HMG-CoA reductase inhibitors of the present invention has been outlined by Moore et al., who showed that the biosynthesis of mevinolin (lovastatin) by *Aspergillus terreus* ATCC 20542 proceeds from acetate via a polyketide pathway (R. N. Moore et al., Biosynthesis of the hypocholesterolemic agent mevinolin by *Aspergillus terreus*. Determination of the origin of carbon, hydrogen, and oxygen atoms by $^{13}$C NMR and mass spectrometry. *J. Amer. Chem. Soc.*, 1985, 107: 3694–3701). Endo and his coworkers demonstrated that similar biosynthetic pathways existed in *Pencillium citrinum* NRRL 8082 and *Monascus ruber* M-4681 (A. Y. Endo et al., Biosynthesis of ML-236B (compactin) and monacolin K., 1985, *J. Antibiot.*, 38:444–448).

The recent commercial introduction of HMG-CoA reductase inhibitors has provided a need for high yielding processes for their production. Methods of improving process yield include, but are not limited to scaling up the process, improving the culture medium or, simplifying the isolation train. The present invention focuses on a method of increasing process yield wherein the increase in productivity is due to the use of a microorganism that produces increased levels of HMG-CoA reductase inhibitor.

It may be desirable to increase the biosynthesis of HMG-CoA reductase inhibitors at the level of gene expression. Such increases could be achieved by increasing the concentration in an HMG-CoA reductase inhibitor-producing microorganism of one or more of the enzymes or enzymatic activities in the biosynthetic pathway of the HMG-CoA reductase inhibitor. It may be particularly desirable to increase the concentration of a rate-limiting biosynthetic activity.

Triol polyketide synthase (TPKS) is a multifunctional protein with at least four activities as evidenced by the product of the enzymatic activity (Moore, supra). TPKS is believed to be the rate-limiting enzymatic activity(ies) in the biosynthesis of the HMG-CoA reductase inhibitor compounds.

The present invention identifies a DNA encoding triol polyketide synthase (TPKS) from *Aspergillus terreus*. The DNA encoding the TPKS of the present invention has been isolated, purified and sequenced. Complementary DNA (cDNA) and genomic DNA sequences corresponding to TPKS have been prepared. The TPKS cDNA of the present invention may be used to increase the production of HMG-CoA reductase inhibitors by HMG-CoA reductase inhibitor-producing microorganisms. The TPKS cDNA of the present invention may also be used to produce purified TPKS.

SUMMARY OF THE INVENTION

DNA encoding the full-length form of triol polyketide synthase (TPKS) is identified. The DNA is sequenced and cloned into expression vectors. Cells transformed with the expression vectors produce increased levels of TPKS and increased levels of HMG-CoA reductase inhibitors. The DNA is useful to produce recombinant full-length TPKS. The DNA may be used to isolate and identify homologues of TPKS present in organisms that are capable of producing polyketides, particularly microorganisms that are capable of producing HMG-CoA reductase inhibitors.

BRIEF DESCRIPTION OF THE DRAWINGS

FIGS. 1A–1T are the nucleotide sequence of triol polyketide synthase SEQ ID NO:1.

FIGS. 2A–2C are the predicted amino acid sequence of triol polyketide synthase SEQ ID NO:2.

FIG. 3 shows pTPKS100.

FIG. 5 shows the alignments of keto acyl synthase SEQ ID NOS:10, 11 & 12, acetyl/malonyl transferase SEQ ID NOS: 13, 14 & 15 and dehydratase SEQ ID NOS:16, 17 & 18, carried out on regions of TPKS, rat fatty acid synthase (FAS) and *P. patulum* 6MSAS. The consensus sequences for keto acyl synthase (SEQ ID NO:35), acetyl/malonyl transferase (SEQ ID NO:36), and dehydratase (SEQ ID NO:37) are shown.

FIG. 6 shows the alignments of enoyl SEQ ID NOS:19, 20 & 21, reductase, keto reductase SEQ ID NOS:22, 23 & 24, and acyl carrier protein SEQ ID NOS:25, 26 & 27, carried out on regions of TPKS. The consensus sequences for enoyl reductase (SEQ ID NO:38), keto reductase (SEQ ID NO:39), and acyl carrier protein (SEQ ID NO:40) are shown.

FIG. 7 is a Chou-Fasman secondary structure prediction of pyridine nucleotide binding regions of TPKS and related proteins. Alcohol Dehydrogenase, SEQ ID NO:28; Rat FAS-ER, SEQ ID NO:29; TPKS-ER, SEQ ID NO:30; TPKS-KR, SEQ ID NO:31; MSAS-KR, SEQ ID NO:32; Rat FAS KR, SEQ ID NO:33.

FIG. 8 shows the S-adenosylmethionine binding regions of a variety of prokaryotic and eukaryotic methyl transferases TPKS (1444), SEQ ID NO:34. The consensus sequence is SEQ ID NO:41.

DETAILED DESCRIPTION OF THE INVENTION

Figure 4:
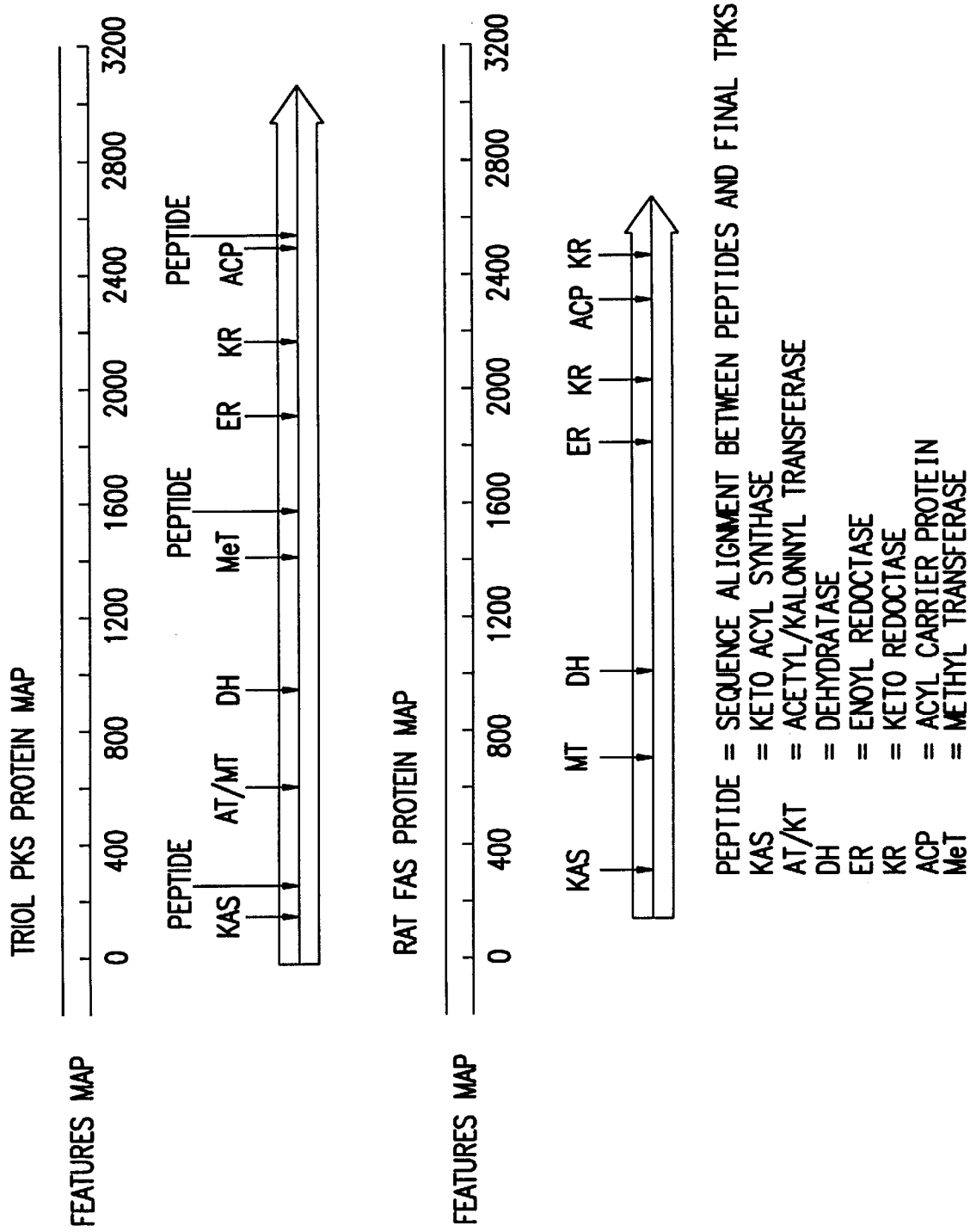
FIG. 4 is a graphic view of the open reading frame of the TPKS protein and the overall placement of the TPKS peptides and PKS activities established by alignments generated by the Intelligenetics GeneWorks program.
Figure 9:
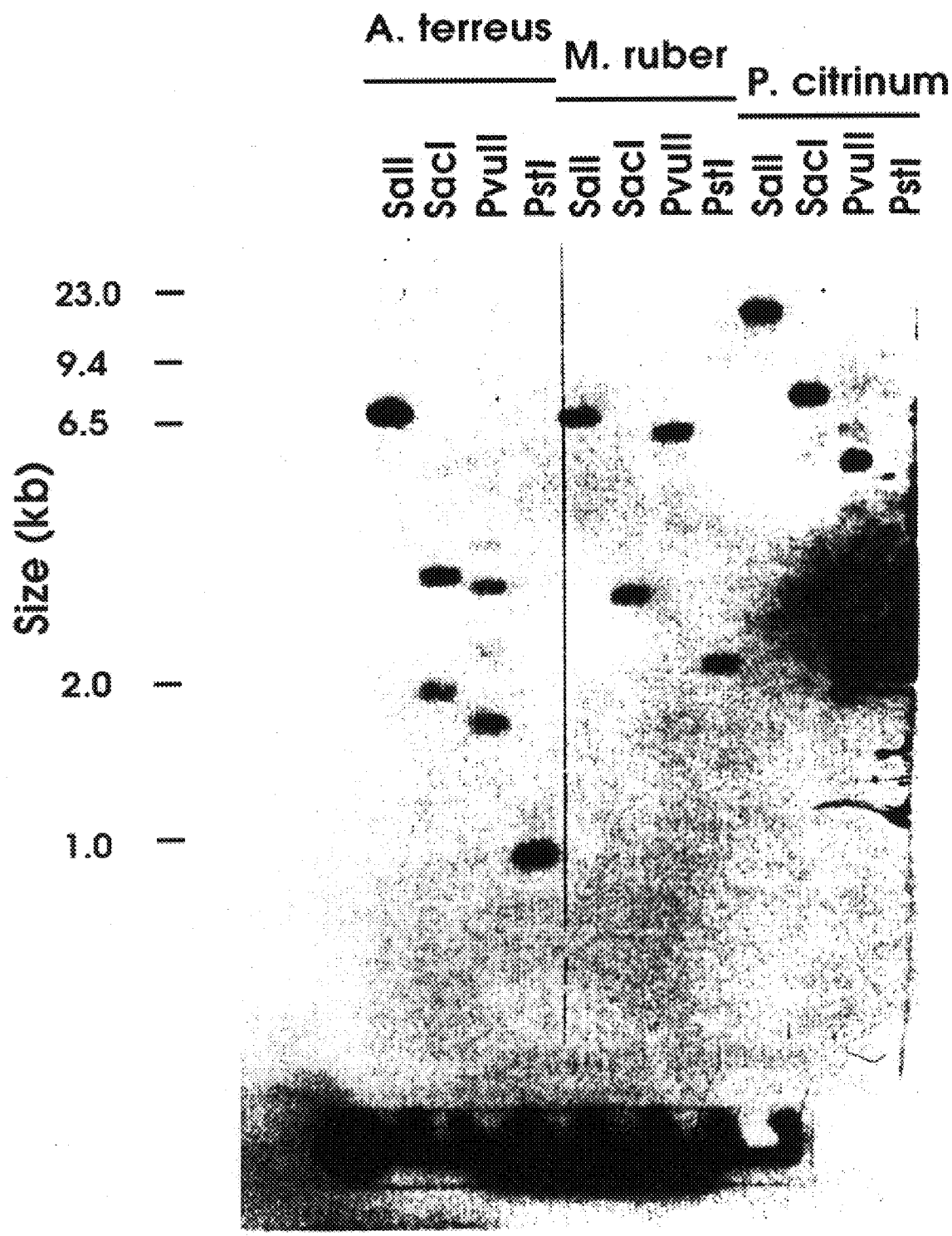
FIG. 9 is a Southern blot showing the homology of ketoacylsynthase of the TPKS of *A. terreus* to *M. ruber* and *P. citrinum*.

The present invention relates to a DNA molecule encoding triol polyketide synthase (TPKS) which is isolated from TPKS-producing cells. Cells capable of producing TPKS include, but are not limited to, strains of *Aspergillus terreus, Monascus ruber, Penicillum citrinum, Penicillum brevicompactum, Hypomyces chrysospermus, Paecilomyces sp* M2016, *Eupenicillium sp.* MM603, *Trichoderma longibrachiatum* M6735 and *Trichoderma pseudokoningii* M6828.

TPKS, as used herein, refers to enzymatic activities that convert acetate precursors and S-adenosyl methionine to an intermediate in the triol biosynthetic pathway. This intermediate is further modified to produce a triol nonaketide. Polyketide synthases from bacteria and fungi employ common enzymatic functions to synthesize polyketides from two carbon units (for a review, see D. A. Hopwood and D. H. Sherman, 1990, "Comparison to fatty acid biosynthesis", *Ann. Rev. Genet.* 24: 37–66).

Polyketides are an important class of natural products because of their structural diversity and because many have antibiotic or other pharmaceutical activities. Most of the economically important polyketides are produced by fungi or actinomycetes.

Polyketide biosynthesis is similar to that of fatty acid biosynthesis in that it involves the sequential condensation of carboxylate units. Unlike fatty acids, which are built from acetate units, polyketides may be built from acetate, propionate, or butyrate units. Additionally, some or all of the β-keto groups added at each cycle of condensation during polyketide biosynthesis are left unreduced, or are reduced only to hydroxyl or enoyl functionalities. This variation in building units and the variation in modification of the beta-keto groups results in a tremendous variety of products as well as difficulty in comparing biosynthetic genes from different pathways.

*Aspergillus terreus* is a filamentous soil fungus; different strains of *A. terreus* produce a variety of polyketides (Springer, J. et al., 1979, terretonin, a toxic compound from *Aspergillus terreus, J. Org. Chem.*, Vol. 44, No. 26, 4852–4854). Lovastatin is a polyketide produced by certain strains of *A. terreus* (Moore, supra). In addition to lovastatin and related metabolites such as triol or monacolin J, other polyketides found in *A. terreus* include sulochrin and related structures (Curtis, R. G. et al.,1964, "The biosynthesis of phenols", *J. Biochem.*, 90:43–51) derived from emodin (Fujii, I., et al., 1982, "Partial purification and some properties of emodin-o-methyltransferase from (+)-geodin producing strain of *Aspergillus terreus*". *Chem. Pharm. Bull.*, 30(6):2283–2286); terreic acid (Sheehan, J. C. et al., 1958, *J. Am. Chem. Soc.*, 80:5536); patulin (D. M. Wilson, 1976, "Adv. Chem. Ser. No. 149") and citrinin (Sankawa, U. et al., 1983, "Biosynthesis of citrinin in *Aspergillus terreus*", *Tetrahedron*, 39(21):3583–3591). Presumably each of these products is made by a specific PKS encoded by a specific and distinct PKS gene(s), thus increasing the difficulty in cloning the triol PKS.

The structure and activity of lovastatin was reported by A. Alberts et al., (*Proc. Natl. Acad. Sci. U.S.A.*, 1980, 77:3957–3961). Lovastatin is a reduced molecule consisting of a methylbutyryl group joined by an ester linkage to a nonaketide having a conjugated decene ring system.

Moore et al., (supra) described lovastatin biosynthesis. Proton and $^{13}$C NMR studies of in vivo labeled lovastatin showed that all the carbons are derived from acetate except in the methyl groups at positions 6 and 2', which were derived from methionine. The triol molecule is composed of nine acetate units. The side-chain is composed of two acetate units. Esterification of triol and the butyrate side chain occurs enzymatically (Kimura, supra). The methyl butyrate side chain is presumably synthesized by a separate PKS. Lovastatin is first synthesized as a highly reduced precursor longer than 9 acetate units which undergoes reoxidation, including oxidative cleavage of a carbon-carbon bond.

Limited information is available for compactin biosynthesis. The most likely pathway would be nearly identical to that of lovastatin biosynthesis in *M. ruber* and *A. terreus,* except that methylation does not occur at the 6 position on the diene ring system.

Polyketide synthases (PKS) and fatty acid synthases (FAS) are classified by functional types. Type II enzymes, typical of bacteria and plants, have a separate polypeptide for each enzymatic activity. Type I enzymes, found in animals, bacteria and fungi, consist of large polypeptides with multiple activities or functional domains. Regions of amino acid sequence similarity have been identified in these genes: domains for ketoacyl synthase, acetyl/malonyl transferase, β-keto reductase, enoyl reductase, dehydratase and acyl carrier protein. The identification of these domains is considered evidence of the resulting enzymatic activity in light of the difficulty in obtaining functional Type I PKS in vitro (Sherman, supra).

Any of a variety of procedures may be used to molecularly clone the TPKS genomic DNA or complementary DNA (cDNA). These methods include but are not limited to, direct functional expression of the TPKS gene in an appropriate host following the construction of a TPKS-containing genomic DNA or cDNA library in an appropriate expression vector system. The preferred method consists of screening a TPKS-containing cDNA expression library constructed in a bacteriophage or vector with an antibody directed against the purified TPKS protein. The antibody is obtained by standard methods (Deutscher, M. (ed), 1990, *Methods in Enzymology*, Vol. 182) by isolating purified TPKS protein from HMG-CoA reductase inhibitor-producing cells, inoculating an appropriate host, such as a rabbit, with the purified protein and, after several boosts, collecting immune sera. Antibody collected from the animal is used to screen the cDNA expression library and cDNA clones expressing TPKS epitopes recognized by the antisera are selected. The positive clones are further purified, labeled and used to probe TPKS-containing genomic or cDNA libraries to identify related TPKS containing DNA. Standard restriction analysis of the related clones can be used to create a restriction map of the region and sequence analysis of the genomic and cDNA clones can be used to define a structural map and the open reading frame of the gene, respectively.

Another method of cloning TPKS involves screening a TPKS-containing cDNA library constructed in a bacteriophage or plasmid shuttle vector with a labelled oligonucleotide probe designed from the amino acid sequence of TPKS. The method may consist of screening an TPKS-containing cDNA library constructed in a bacteriophage or plasmid shuttle vector with a partial cDNA encoding the TPKS subunits. This partial cDNA is obtained by the specific PCR amplification of TPKS DNA fragments through the design of degenerate oligonucleotide primers from the amino acid sequence of the purified TPKS subunits.

It is readily apparent to those skilled in the art that other types of libraries, as well as libraries constructed from other cells or cell types, may be useful for isolating TPKS-encoding DNA. Other types of libraries include, but are not limited to, cDNA libraries derived from other cells or cell lines and genomic DNA libraries.

It is readily apparent to those skilled in the art that suitable cDNA libraries may be prepared from cells or cell lines which have TPKS activity. The selection of cells or cell lines for use in preparing a cDNA library to isolate TPKS cDNA may be done by first measuring cell associated TPKS activity using incorporation of radiolabelled acetate and separation of products by high performance liquid chromatography (HPLC).

Preparation of cDNA libraries can be performed by standard techniques well known in the art. Well-known cDNA library construction techniques can be found for example, in Maniatis, T., Fritsch, E. F., Sambrook, J., *Molecular Cloning: A Laboratory Manual* (Cold Spring Harbor Laboratory, Cold Spring Harbor, N.Y., 1982).

It is also readily apparent to those skilled in the art that DNA encoding TPKS may also be isolated from a suitable genomic DNA library. Construction of genomic DNA libraries can be performed by standard techniques well-known in the art. Well-known genomic DNA library construction techniques can be found in Maniatis et al., (supra).

In order to clone the TPKS gene, knowledge of the amino acid sequence of TPKS may be necessary. To accomplish this, TPKS protein may be purified and partial amino acid sequence determined by conventional methods. Determination of the complete amino acid sequence is not necessary. Once suitable amino acid sequences have been identified, the DNA sequences capable of encoding them are synthesized.

Because the genetic code is degenerate, more than one codon may be used to encode a particular amino acid, and therefore, the amino acid sequence can be encoded by any of a set of similar DNA oligonucleotides. Only one member of the set will be identical to the TPKS sequence but will be capable of hybridizing to TPKS DNA even in the presence of DNA oligonucleotides with mismatches. The mismatched DNA oligonucleotides may still hybridize to the TPKS DNA to permit identification and isolation of TPKS encoding DNA.

It is readily apparent to those skilled in the art that DNA encoding TPKS from a particular organism may be used to isolate and purify homologues of TPKS from other organisms. To accomplish this, the first TPKS DNA may be mixed with a sample containing DNA encoding homologues of TPKS under appropriate hybridization conditions. The hybridized DNA complex may be isolated and the DNA encoding the homologous DNA may be purified therefrom.

cDNA clones encoding TPKS may be isolated in a two-stage approach employing polymerase chain reaction (PCR) based technology and cDNA library screening.

Amino acid sequence information may be obtained by automated amino acid sequencing using Edman chemistry of both the intact protein and the peptide fragments generated by specific proteolytic cleavage. Following incubation for the prescribed periods, digestion is terminated and resulting peptide fragments are fractionated and detected.

TPKS in substantially pure form derived from natural sources according to the purification processes described herein, is found to be encoded by a single mRNA.

The cloned TPKS cDNA obtained through the methods described above may be expressed by cloning it into an expression vector containing a suitable promoter and other appropriate transcription regulatory elements, and transferred into prokaryotic or eukaryotic host cells to produce recombinant TPKS. Techniques for such manipulations are well-known in the art.

In order to simplify the following Examples and the Detailed Description, certain terms will be defined.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells and animal cells. Expression vectors include, but are not limited to, cloning vectors, modified cloning vectors, specifically designed plasmids or viruses. Specifically designed vectors allow the shuttling of DNA between hosts, such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters.

An expression vector is a replicable DNA construct in which a DNA sequence encoding a TPKS is operably linked to suitable control sequences capable of effecting the expression TPKS in a suitable host. Control sequences include a transcriptional promoter, an optional operator sequence to control transcription and sequences which control the termination of transcription and translation.

Certain vectors, such as amplification vectors, do not need expression control domains but rather need the ability to replicate in a host, usually conferred by an origin of replication, and a selection gene to facilitate recognition of transformants.

A promoter is defined as a DNA sequence that directs RNA polymerase to bind to DNA and initiate RNA synthesis. A strong promoter is one which causes mRNAs to be initiated at high frequency.

DNA encoding TPKS may also be cloned into an expression vector for expression in a host cell. Host cells may be prokaryotic or eukaryotic, including but not limited to bacteria, yeast, mammalian and insect cells and cell lines.

The expression vector may be introduced into host cells via any one of a number of techniques including but not limited to transformation, transfection, protoplast fusion, and electroporation. The expression vector-containing cells are clonally propagated and individually analyzed to determine whether they contain the TPKS gene or produce TPKS protein. Identification of TPKS expressing host cell clones may be done by several means, including but not limited to immunological reactivity with anti-TPKS antibodies, and the presence of host cell-associated TPKS activity.

Expression of TPKS DNA may also be performed using in vitro produced synthetic MRNA. Synthetic MRNA can be efficiently translated in various cell-free systems, including but not limited to wheat germ extracts and reticulocyte extracts, as well as efficiently translated in cell based systems, including but not limited to microinjection into frog oocytes, with micro-injection into frog oocytes being preferred.

PCR is the polymerase chain reaction, which is a technique for copying the complementary strands of a target DNA molecule simultaneously for a series of cycles until the desired amount is obtained.

Plasmids are generally designated by a low case p preceded or followed by capital letters and/or numbers. The starting plasmids used in this invention are commercially available, are publicly available on an unrestricted basis, or can be constructed from such available plasmids by conventional procedures. In addition other equivalent plasmids or constructs will be readily apparent to one skilled in the art.

Transformed host cells are cells which have been transformed or transfected with TPKS vectors constructed using recombinant DNA techniques. Expressed TPKS may be deposited in the cell membrane of the host cell or may be intracellular or may be secreted.

It is also well known, that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is also well known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate. Alteration of the amino acid sequence may lead to altered properties that in turn result in the production of modified structures; for example, the elimination of one of the reductase activities may result in the biosynthesis of a less-reduced compound.

The full-length TPKS-encoding DNA in plasmid pLOA was designated pTPKS100. A sample of pTPKS-100 in *E. coli* strain JM109, was deposited under the terms of the Budapest Treaty, on Sep. 15, 1993 in the permanent culture collection of the American Type Culture Collection, at 10801 University Boulevard, Manassas, Va., 20110-2209, and has been assigned the Accession number ATCC 69416.

The following examples illustrate the present invention without, however, limiting the same thereto.

EXAMPLE 1
Culture Conditions

Three strains of *Aspergillus terreus* were used. The two lovastatin-producing strains included *A. terreus* ATCC 20542. A lovastatin nonproducing strain was also used. A lovastatin-nonproducing strain or a lovastatin-overproducing strain of *A. terreus* may be derived from lovastatin-producing strains of *A. terreus* that are publicly available; an example of a publicly-available strain is *A. terreus* MF-4833, which is deposited with the American Type Culture Collection under Accession No. 20542. One skilled in the art would appreciate that a variety of techniques such as mutagenesis techniques, including but not limited to ultraviolet irradiation, treatment with ethyl-methanesulfonate (EMS), exposure to nitrous acid, nitrosoguanidine and psoralen-crosslinking, could be used to generate a strain that does not produce or which overproduces lovastatin. The extent of the mutagenesis may be determined in a variety of ways including auxotrophy, i.e., the requirement of the mutated strain for a specific growth substance beyond the minimum required for normal metabolism and reproduction of the parent strain as well as measurement of production of lovastatin by individual cultures. An alternative monitoring system involves the use of an intercalating dye such as acriflavine, which prevents any growth of the parent (lovastatin-producing) strain when plated at 10,000 spores per plate but, following mutagenesis, allows growth of about 3–5 colonies per plate. Alternatively, the extent of mutagenesis may be monitored by visual observation of colonies having morphologies or colors that differ from the unmutagenized parent strain. Mutant strains are reisolated and pooled and subjected to further mutagenesis so that, by repetition of these procedures, mutated strains of *A. terreus* that do not produce or which overproduce lovastatin may be obtained.

*Monascus ruber* ATCC 20657 and *Penicillium citrinum* ATCC 20606 were used in hybridization studies.

The strains were maintained on YME+TE medium. The recipe for YME+TE medium is as follows:
- 0.4% Yeast Extract (w/v);
- 1.0% Malt Extract (w/v);
- 0.4% Glucose (w/v);
- 0.5% Trace Element (TE; v/v); and
- 2.0% agar (w/v) in 1 liter of water, pH 7.2.

The recipe for Trace Elements (TE) is as follows:
- 0.1% $FeSO_4$-$7H_2O$ (w/v);
- 0.1% $MnSO_4$-$H_2O$ (w/v);
- 0.0025% $CuCl_2$.$2H_2O$ (w/v);
- 0.0132% $CaCl_2$.$2H_2O$ (w/v);
- 0.0056% $H_3BO_3$ (w/v);
- 0.0019% $(NH_4)_6Mo_7O_{24}$.$4H_2O$ (w/v); and
- 0.02% $ZnSO_4$.$7H_2O$ (w/v) in 1 liter of water.

EXAMPLE 2
Fermentation Conditions

For the generation of spore stocks, single colonies were generated by growing on YME+TE plates for 8 days at 28° C. and 65% relative humidity. Single colonies were removed, and streaked on YME+TE slants. The slants were incubated for 8 days at 28° C. in 65% humidity. Spores were harvested by addition of 2 ml of Spore Suspension Solution (SSS). SSS contains 10% Glycerol (v/v) and 5% Lactose (w/v) in water. Spores were scraped into the SSS with a sterile inoculation loop and counted. The suspension was stored at −20° C.

A two-stage fermentation from spore suspensions was used for the production of lovastatin. A seed culture was started by inoculating $1 \times 10^8$ spores into 2 ml/15 ml culture tube of HLC medium.

The recipe for HLC medium is as follows:
- 1.5% $KH_2PO_4$ (w/v);
- 2.0% Cerelose (w/v);
- 0.1% Ardamine pH (Champlain Industries) (w/v);

1.5% Pharmamedia (Traders Protein) (w/v);
0.2% Lactic acid (v/v); and
0.4% ammonium citrate (w/v) in 1 liter of water.

The pH of HLC medium was adjusted to pH 7.2 before sterilization.

Cultures were shaken at a 30 degree angle at 28° C. for approximately 28 hours on a rotary shaker with a 70 mm diameter amplitude at 220 rpm. Two ml of seed culture was used to inoculate 25 ml of GP-9 medium in a 250 ml flask.

The recipe for GP-9 medium is as follows:

0.9% Ammonium Citrate (w/v);
0.12% Ardamine pH (w/v);
1.2% Cerelose (w/v);
4.0% Pharmamedia (w/v);
24.5% Lactose (w/v); and
0.2% P 2000 (v/v) in water at pH 7.2.

Incubation was continued as described for seed cultures without the 30 degree angle. Lovastatin production was monitored after 12 days of fermentation.

A one stage fermentation of *A. terreus* cultures in CM media was used to generate vegetative mycelia for transformations or DNA preparations. Fermentations were started by inoculating $1 \times 10^8$ conidiospores into 50 ml of CM medium in a 250 ml flask and incubated as described.

The recipe for Complete Medium (CM) is as follows:

50 ml of Clutterbuck's salts;
2.0 ml Vogel's Trace elements;
0.5% Tryptone (w/v);
0.5% Yeast extract (w/v); and
1.0% Glucose (w/v) in one liter of water.

The recipe for Clutterbuck's salts is as follows:

12.0% $Na_2NO_3$ (w/v);
1.02% KCl (w/v);
1.04% $MgSO_4.7H_2O$ (w/v); and
3.04% $KH_2PO_4$ (w/v).

The recipe for Vogel's trace elements is as follows:

0.004% $ZnCl_2$ (w/v);
0.02% $FeCl_3$ (w/v);
0.001% $CuCl_2$ (w/v);
0.001% $MnCl_2.4H_2O$;
0.001% $NaB_4O_7.10H_2O$ (w/v); and
0.001% $(NH_4)_6MO_7O_{24}.7H_2O$ (w/v).

EXAMPLE 3

Construction of Vector. pLO9 pLO9 is a 5.6 kb vector constructed with features useful for both cosmid library construction and fungal transformations. For dominant selection in *Aspergillus terreus*, pLO9 contains a *Streptoalloteichus hindustanus* phleomycin resistance gene driven by an *A. niger* β-tubulin promoter and terminated by a *Saccharomyces cerevisiae* terminator sequence. For selection in *Escherichia coli*, the vector contains the ampicillin resistance gene and for lambda packaging, the vector contains a lambda cos site. The construction of pLO9 is described below.

The phleomycin resistance marker originated from *S. hindustanus* and the termination sequence is from the CYC1 gene in *S. cerevisiae*. Both sequences were isolated on one DNA fragment from pUT713 (CAYLA, Toulouse Cedex, France) by digesting pUT713 with the restriction enzymes BamH1 and BglII. The isolated fragment was cloned into BamH1-digested pUC18 to produce vector pLO1. The genomic copy of the β-tubulin gene from *A. niger* ATCC 1015, was cloned as a 4.3 kb EcoR1 fragment in pUC8 to create p35-C-14. Several modifications were made to the genomic sequence. An EcoRI site was introduced at the initiator ATG by in vitro mutagenesis. The HindIII site in the promoter was removed by digestion with exonuclease, filling in with Klenow, and religation. Finally, an upstream EcoRI site was changed to a PstI site by digestion with EcoRI, filling in with Klenow and addition of a PstI linker by religation with ligase. The β-tubulin promoter was then subcloned as a PstI to EcoRI fragment in pUC8 to create pC15-1. An XbaI site was introduced at the initiator ATG by digestion with EcoRI, filling in with Klenow, addition of a XbaI linker and religation. The resulting vector was named pTL-113.

The β-tubulin promoter was cloned upstream of the phleomycin gene by cutting pTL113 with PstI and XbaI and cloning the isolated promoter fragment into the PstI and XbaI sites of pLO1 to produce pLO3. The BglII site was removed with a fill in reaction followed by blunt-end ligation to produce vector pCS12. The PstI to Hind III fragment containing the beta tubulin promoter, phleomycin resistance gene, and the terminator sequence were cloned into a pUC8 vector to generate pLO6. The XbaI site at the ATG was removed by a fill-in reaction and ligation to give pLO7. The PstI to HindIII was moved as a fragment into a pUC18 backbone in which the XmaI site had been filled and replaced with a BglII linker. The resulting vector was named pLO8. A PstI fragment containing the lambda cos site from pJL21 was inserted into the vector to generate pLO9.

EXAMPLE 4

Isolation of Genomic DNA

Vegetative mycelia were generated in CM media for 48 hr at 220 rpm at 28° C. Mycelia were collected by filtration through cheesecloth and frozen in liquid nitrogen for lyophilization overnight. Lyophilized mycelia were ground with sand using a mortar and pestle and suspended in 5 ml of Breaking Buffer (100 mM NaCl; 50 mM EDTA; 10 mM Tris, pH 8.0; 1% SDS; 50 ug/ml pancreatic RNase; 50 ug/ml Proteinase K). The mix was transferred to a 125 ml flask and an equal volume of Tris-saturated phenol/chloroform (50:50) was added. The flask was shaken for 1 hour at 37° C. and 200 rpm. The aqueous layer was removed after centrifugation at 10,000 rpm for 10 minutes. The aqueous layer was extracted twice more with phenol/chloroform and was then extracted once with chloroform. DNA was precipitated from the aqueous layer by addition of 0.1 volume 3 M NaCl and 2.5 volumes of ethanol and then freezing at −70° C. for 10 minutes. The precipitated DNA was collected by centrifugation at 10,000 rpm for 15 minutes. The pelleted DNA was dried and resuspended in a solution of 10 mM Tris-HCl, 1 mM EDTA, pH 7.5. DNA concentrations were determined by measuring absorbance at wavelength 260 nM.

EXAMPLE 5

Construction of *A. terreus* Libraries

A. Preparation of Genomic Fragments

*A. terreus* genomic DNA was isolated as described. Large random DNA fragments for insertion into the vectors were isolated by partially digesting 10 µg of DNA with the restriction enzyme Sau3A. The digested DNA was electrophoresed on a 1.0% Agarose gel. For the genomic library, an area containing 9–23 kb sized fragments was cut from the gel. For the cosmid library, another segment of the gel containing 30–60 kb sized fragments was excised. The large chromosomal DNA fragments contained in the gel slices were isolated by electroelution. The DNA was concentrated by addition of 0.1 volumes of 3 M sodium acetate and 2.5 volumes of ethanol, freezing at −70° C. for 15 minutes, and centrifugation at 10,000 rpm for 10 minutes to precipitate the DNA.

B. Construction of the *A. terreus* Cosmid Library

The pLO9 cosmid DNA was used to supply the two arms and cos sites required for lambda packaging. Two fragments were isolated from pLO9 for the packaging reaction.

Fragment one was isolated by digesting pLO9 with Xba1, phosphatasing with HK phosphatase (Epicenter Technologies), digesting with BgII, electroelutirig on a 1% Agarose gel, concentrating by the addition of 0.1 volumes of 3 M sodium acetate and 2.5 volumes of ethanol, freezing at −70° C. for 15 minutes and centrifuging at 10,000 rpm for 10 minutes to precipitate the DNA.

Fragment two was isolated by digesting pLO9 with SmaI, phosphatasing with HK phosphatase and then digesting with BgIII. Fragment two was isolated with the procedure described for fragment one. Fragment one, fragment two and isolated *A. terreus* insert DNA were ligated in a 1:1:2 ratio at a concentration of 0.5 µg of each DNA.

C. Packaging into Lambda Phage and Plating

Packaging into lambda phage was accomplished by mixing the ligation mixture with 10 µl of extract A from *E. coli* strain BHB2688 (Amersham) and 15 µl of extract B from *E. coli* strain BHB2690 (Amersham). The packaging mix was incubated at 22° C. for 120 minutes. A volume of 500 µl of SM (0.58% NaCl(w/v); 0.20% $MgSO_4$(w/v); 0.05 M Tris pH 7.5; 0.01% Gelatin(w/v)) and 10 µl of chloroform was then added to the packaging mix.

*E. coli* strain DH5 was prepared for transfection by growing cells to an optical density of 1.0 at wavelength 600 nm in LB+maltose medium. LB+maltose medium consists of 1.0% Bacto-tryptone (w/v); 0.5% Bacto-yeast extract (w/v); 1.0% NaCl (w/v); pH 7.5; 0.2% Maltose (v/v) is added after autoclaving.

The cells were centrifuged at 4,000 rpm for 10 minutes and resuspended in 10 mM $MgSO_4$. Fifty microliters of the packaging mix was added to 200 µl of the resuspended DH5 cells and incubated for 30 minutes at 37° C. A 500 µl of aliquot of LB medium was added and the mix was incubated for 30 minutes at 37° C. The cell mix was spread on LB agar plates containing 100 µg/ml ampicillin (Sigma) and incubated at 37° C. A total of 10,000 colonies were generated with this library.

D. Construction of the *A. terreus* Genomic Library

The lambda replacement vector, EMBL3 (Promega), was used for the construction of the genomic library. The vector was purchased as predigested arms ready for ligation with the genomic inserts. The two arms were ligated to the 9–23 kb genomic inserts at a ratio of 1:1:2, packaged into lambda phage, and plated for hybridization with selected probes as described above.

EXAMPLE 6

A. Isolation of Cosmid DNA from *E. coli*

The *A. terreus* cosmid library in *E. coli* was grown on 25 cm×25 cm plates containing 200 ml LB agar supplemented with 100 µg/ml ampicillin added. Nearly confluent colonies were scraped from plates in 10 ml of cold TS solution (50 mM Tris, pH 8.0 and 10% Sucrose(w/v)). A 2.0 ml aliquot of 10 mg/ml lysozyme made in 0.25 M Tris, pH 8.0 was added; then 8 ml of 0.25 M ethylenediamine tetraacetic acid (EDTA) was added. The mix was inverted several times and incubated on ice for 10 minutes. A 4 ml aliquot of a 10% SDS solution was added slowly while mixing gently with a glass rod. Next, 6.0 ml of 5 M NaCl was added slowly while mixing with a glass rod. The cell lysate was incubated on ice for 1 hour and then centrifuged. The supernatant was saved and then extracted twice with an equal volume of Tris-saturated Phenol/Chloroform (50:50). DNA was precipitated by adding 2 volumes of ethanol, freezing at −70° C. for 15 minutes and then centrifuging at 3,000 rpm for 15 minutes. The precipitated cosmid DNA was dried and resuspended in 9 ml of Tris-EDTA.

Cosmid DNA was prepared for cesium chloride density gradient purification by dissolving 10 gm of $CsCl_2$ in the DNA suspension and then adding 250 µl of 10 mg/ml ethidium bromide. Cosmid DNA was banded with a 20 hour centrifugation in a Ti865.1 Sorvall rotor at 55,000 rpm. The DNA bands representing cosmid DNA were recovered from the gradient, and ethidium bromide was removed by extraction with water-saturated butanol. Cosmid DNA was precipitated by adding 3 volumes of water and 10 volumes of ethanol, incubating on ice for 30 minutes and then centrifuging. The DNA was resuspended in Tris-EDTA and reprecipitated by the addition of 0.1 volume of 3 M sodium acetate and 2.5 volumes of ethanol. DNA was frozen at −70° C. for 10 minutes, centrifuged, and resuspended in Tris-EDTA.

The DNA preparation was electrophoresed through a 0.5% Low Melting Temperature Agarose (BioRad) gel to eliminate contamination by pLO9 DNA. The band containing cosmid DNA with inserts was cut from the gel and heated to 65° C. with 2 volumes of Tris-EDTA. The melted agarose was extracted 3 times with Tris-saturated phenol and then once with chloroform. Cosmid library DNA was precipitated by addition of 0.1 volumes of 3 M sodium acetate and 2.5 volumes of ethanol, freezing at −70° C. for 15 minutes, and centrifuging at 10,000 rpm for 15 minutes. The DNA was dried and resuspended in Tris-EDTA. The concentration of DNA was determined by measuring the optical density at 260 nm.

EXAMPLE 7

Transformation of *A. terreus*

Cultures were grown by inoculating $1 \times 10^8$ conidiospores into 50 ml of CM media in a 250 ml Erlenmeyer flask. Cultures were grown for between 24 and 30 hr at 200 rpm and 28° C. Mycelia were harvested by gravity filtration through Miracloth. Mycelia (4 g) were transferred to a 500 ml Erlenmeyer flask containing 100 ml KMP. KMP consists of 700 mM KCl, 800 mM Mannitol, and 20 mM $KH_2PO_4$ pH 6.3. Lysing Enzymes from *Trichoderma harzianum* (100 mg; Sigma) was added. Flasks were shaken at 100 rpm for 18 hours at 28° C.

Spheroplasts were harvested by gravity filtration through Miracloth. The filtrate was collected in 50 ml conical centrifuge tubes, concentrated by centrifugation and washed by resuspending the spheroplasted cells in 15 ml of KCM solution. KCM consists of 700 mM KCl; 10 mM MOPS adjusted to pH 5.8. The washing was repeated twice. Washed spheroplasts were resuspended at a concentration of $5 \times 10^7$/ml in KCMC. KCMC consists of 5% 1 M $CaCl_2$ and 95% KCM.

For each transformation, a sample of 5 µg of DNA was brought to a volume of 20 µl in Tris-EDTA; then 5 units of heparin in 6.5 µl of KCMC was added. Next, 200 µl aliquot of the spheroplast suspension was added to the DNA-containing solution. Finally, 50 µl of aliquot of a solution containing 5% 1 M $CaCl_2$ and 95% PCMC (40% PEG 8,000; 10 mM MOPS, pH 5.8; 0.05 M $CaCl_2$) was added. The mixture was incubated on ice for 30 minutes.

An aliquot (600 µl) of the KCMC solution was added to a 45° C. equilibrated solution of MA. MA consists of 5% Clutterbuck's salts(v/v); 0.5% Tryptone (w/v); 0.5% Yeast Extract (w/v); 1.0% Glucose(w/v); 23.4% Mannitol(w/v) and 3% Agar. This suspension was divided among 5 pre-weighed petri dishes and incubated at 28° C. for 4 hours. The weight of agar in each plate was determined by a second weight and an equal amount of Overlay (OL) consisting of: 1% Peptone (w/v); 1% Agar (w/v); with between 100 $\mu$g/ml and 150 $\mu$g/ml (strain ATCC 20542) of phleomycin was added to each petri dish. Petri dishes were incubated at 28° C. and 65% humidity for 7–10 days before transformed colonies were picked.

EXAMPLE 8
Rescue of Cosmid DNA from A. terreus

The transforming cosmid DNA was rescued from an A. terreus transformants by isolating chromosomal DNA and packaging into lambda phage particles. Isolation of genomic DNA and packaging into lambda phage were performed as described above.

EXAMPLE 9
Detection of Lovastatin

Fermentation extracts were prepared by adding two volumes of reagent alcohol to the fermentation flasks and shaking the flasks were shaken for 15 minutes at 220 rpm and 28° C. The contents were allowed to settle for 15 minutes and 1 ml of the liquid was removed. The sample was diluted 1/20 in methanol, filtered and then analyzed by HPLC. Lovastatin was detected by a Waters HPLC using a 8 mm×10 cm C18 4 um Waters Novapak column. Mobile phases were A: Acetonitrile with 0.02% Trifluoroacetic acid and B: Distilled water with 0.02% Trifluoroacetic acid. Gradients were run at a flow rate of 1.5 ml/min. Initial conditions were 35% A and 65% B and were held for 1 minute after sample injection. A gradient was formed to 65% A and 35% B over 3 minutes and held for 3.6 minutes. Lovastatin ammonium salt was detected at 239 nm.

EXAMPLE 10
Southern Analysis of DNA

Southern analysis was performed by electrophoresing 5 $\mu$g of digested DNA on a 1.0% agarose gel in TAE buffer (0.04 M Tris and 0.002 M EDTA). DNA in the gel was denatured by soaking the gel in Solution A (1.5 M NaCl and 0.5 M NaOH) for 30 minutes. The gel was then neutralized in Solution B (1.0 M Tris and 1.5 M NaCl) for 30 minutes. DNA was transferred to nitrocellulose or nylon membranes by blotting overnight with a 10×SCC solution. SSC consists of 8.75% NaCl (w/v) and 4.4% sodium citrate (w/v), pH 7.0. DNA was baked onto the nitrocellulose at 80° C. under vacuum for 30 minutes.

Standard hybridization conditions were as described in Sambrook, J. et al., (*Molecular Cloning*, 1989 (ed. Chris Nolan) Cold Spring Harbor Press). Membranes were prepared for hybridization by incubating at 42° C. in hybridization buffer consisting of: 6×SSC, 5×Denhardt's reagent, 0.5% SDS, 100 $\mu$g/ml denatured and fragmented salmon sperm DNA, and 40% formamide. After incubating for two hours, the denatured labeled probe was added and further incubated overnight at 42° C. Unless otherwise stated, the filters were washed twice in 6×SSC and 0.1% SDS at room temperature for 15 minutes followed by two 30 minute washes at 42° C. in 0.1×SSC and 0.5% SDS. Filters were exposed to X-ray film for visualization of the signal.

EXAMPLE 11
A. Isolation of Triol Polyketide Synthase from A. terreus

Mycelia of A. terreus were grown in GP-9 medium. After 48 hours the mycelia were collected by vacuum filtration, washed with cold water, frozen in liquid nitrogen and lyophilized. All subsequent steps of the purification were performed on ice or at 3° C. unless otherwise noted.

Lyophilized mycelia (6 g) were homogenized by grinding with 20 gm glass beads (0.2 mm) in a mortar with pestle in 135 ml homogenization buffer consisting of: 20 mM Tris, pH 8; 10% glycerol; 5 mM EDTA; 50 mM NaCl; 5 mM ascorbic acid; 3.8 $\mu$g/ml leupeptin; 17.7 $\mu$g/ml chymostatin; 2.0 $\mu$g/ml pepstatin, 42 $\mu$g/ml turkey trypsin inhibitor; 0.2 mM PMSF; and 2.2% (dry wt/v) hydrated polyvinyl polypyrrolidone. The homogenate was centrifuged at 7,650×g for 10 minutes; and the supernatant applied to an SH-affinity column (Affi-gel 501 organomercurial agarose; Bio-Rad; 1.5×8.0 cm) equilibrated in Buffer A. Buffer A consists of 20 mM Tris, pH 8; 50 mM NaCl; 5 mM EDTA; 5 mM ascorbic acid; at 30 ml/hr. The column was washed with 25 ml Buffer A followed by 75 ml Buffer A containing 0.5 M NaCl. After reequilibrating the column with 50 ml Buffer A, bound proteins were eluted with 40 ml Buffer A supplemented with 100 mM dithiothreotol (DTT). The eluted protein fraction was made 4.2 $\mu$g/ml leupeptin; 2 $\mu$g/ml pepstatin; 18 $\mu$g/ml chymostatin; 0.2 mM PMSF and then was pelleted by ultracentrifugation at 180,000×g for 16 hr. The supernatant was discarded, and the pellet was rinsed with a buffer consisting of 20 mM Tris, pH 8; 5 mM ascorbic acid; 1 mM DTT; 1 mM EDTA. The washed pellet was resuspended in 2 ml of buffer consisting of 40 mM Tris, pH 6.8; 20 mM DTT; 2% SDS, then heated to 90° C. for 10 minutes and put on ice.

A 250 $\mu$l aliquot of the resuspended pellet was combined with an equal volume of sample buffer (125 mM Tris, pH 6.8; 20% glycerol; 0.005%(w/v) bromphenol blue; 4%(w/v) SDS; 1.5 M beta mercaptoethanol) and heated to 95° C. for 10 minutes. The sample was electrophoresed on a preparative 1.5 mm, 4% acrylamide SDS precast gel (Novex) at 145V for 2 hr using Laemmeli electrode buffer system (25 mM Tris; 192 mM glycine; 0.1% SDS). When a prestained 200 kD reference standard was 1.4 cm from the bottom of the gel, the electrophoresis was terminated.

Proteins were visualized as follow. The gel was rinsed for 5 seconds in distilled $H_2O$ then rinsed for 10 minutes in 0.2 M imidazole with shaking and was then transferred to a solution of 0.3 M zinc acetate for 5 minutes with shaking. The gel was then rinsed in water. The TPKS, which ran with an apparent molecular weight of 235 kD, was localized to a relative mobility position of 0.53 (relative to the bottom of the gel). The TPKS protein was the protein of greatest abundance on the gel; no significant protein banding was seen with lower Rf. The apparent 235 kD protein band was excised from the gel and was then destained in 0.25 M Tris and 0.25 M EDTA pH 9.5 for approximately 5 minutes.

The destained gel slice was crushed between two glass plates and placed in a 50 ml tube containing 5 ml of 20 mM Tris, 5 mM EDTA, 0.1% SDS, pH 8.0. The tube was shaken on a rotary shaker for 48 hours at 37° C. Gel fragments were removed by centrifugation, and the supernatant containing the eluted protein was concentrated to 100 $\mu$l with a Centricon 30 microconcentrator (Amicon).

B. Molecular Weight Determination

The gel-purified protein was resuspended in Laemmli load buffer, heated to 95° C. for 5 min. and then electrophoresed on a 4–15% gradient SDS polyacrylamide gel (BioRad Ready-Gel) in Laemmli electrode buffer. After staining, the molecular weight of the protein was determined by comparison to molecular weight standard proteins.

C. Antibody Production

The TPKS protein was prepared via preparative SDS-PAGE as described, except the protein was not electroeluted from the acrylamide gel matrix. Following destaining, the gel slice was crushed between two glass plates, and first forced through a 18 gauge syringe needle and then through a 25 gauge syringe needle. A 0.5 ml aliquot of the 25 gauge needle eluate was mixed with an equal volume of Freund's complete adjuvant and injected intradermally at five sites of a New Zealand white male rabbit. Boosts were done at 21 and 42 days using protein prepared as described, but mixed with 0.5 ml of Freund's incomplete adjuvant. Ten days after the final boost the rabbit was exsanguinated and the antiserum collected.

D. Affinity Purification of Antibody

Affinity purified antibody was prepared by immobilizing the TPKS protein to PVDF membrane by transfer from a preparative SDS polyacrylamide gel. The TPKS was visualized and that area of the membrane cut out. After blocking in 5% (w/v) non-fat dry milk in TTBS for 1 hour, the membrane was washed 3×5 minutes in TTBS. A 2 ml aliquot of antisera was diluted 1:1 with TTBS supplemented with 1% (w/v) non-fat dry milk and incubated with the immobilized antigen for 5 hours. The membrane was then washed 4× (10 minutes per wash) with TTBS, and the bound antibody was eluted with 2 ml of 0.1 M glycine, pH 2.8. The eluted antibody was neutralized with 50 $\mu$l of 1.0 M Tris, pH 9.5 and concentrated twenty-fold.

E. Western Blot Analysis

Purified TPKS protein and partially purified protein preparations of organomercurial eluates were resolved by 4% acrylamide SDS-PAGE (NOVEX, precast 1.0 mm thick gels) and then transferred to nitrocellulose in Towbin transfer buffer (25 mM Tris; 192 mM glycine, pH 8.3; 20% methanol; 0.05% SDS) at 240 mA for 2 hr. All subsequent steps were done at room temperature with shaking.

The nitrocellulose blot was rinsed for 1 minute in TBS (50 mM Tris, pH 7.5; 0.5 M NaCl) and then blocked for 2 hours in TBS supplemented with 0.05% Tween 20 (TTBS) and 5% (w/v) non-fat dry milk. The blot was incubated with the primary antibody (a 1:1000 dilution of rabbit antisera in TFBS containing 1% (w/v) non-fat dry milk) for 16 hr. The blot was washed in TTBS 3 times for 5 min. The blot was incubated with the second antibody (goat anti-rabbit alkaline phosphatase conjugate diluted 1:1000) for 2 hr in TTBS supplemented 1% (w/v) non-fat dry milk. After washing 4 times (10 minutes per wash) in TTBS, color development was achieved with 5-bromo4-chloro-3-indolyl phosphate (115 $\mu$g/ml) and nitroblue tetrazolium (330 $\mu$g/ml) in 66 mM Tris, pH 9.5; 0.1 M NaCl; 5 mM $MgCl_2$.

EXAMPLE 12

Isolation of Aspergillus RNA

A. Isolation of Total RNA

*A. terreus* was grown for 48 hours in 25 ml of GP-9 fermentation medium at 28° C. and 220 rpm on a rotary shaker. Mycelia were collected by vacuum filtration through Miracloth and cheesecloth and washed with approximately 100 ml distilled water. The mycelia were scraped from the filter into a plastic beaker and frozen with liquid nitrogen. Frozen mycelia were stored at −80° C. until needed.

Frozen mycelia were weighed and placed in a mortar chilled with liquid nitrogen. Approximately 2 g of 0.2 mm glass beads were added, and the mix was ground to a fine powder with a pestle. Liquid nitrogen was added as needed to keep the mycelia frozen at all times. Ground mycelia were added to a flask containing approximately 2.5 ml/g Breaking Buffer (50 mM Tris pH 7.4; 150 mM NaCl; 5 mM EDTA; 5% SDS(w/v)) and an equal volume of Tris-saturated phenol:chloroform:isoamyl alcohol (50:50:1), and vanadyl ribonucleoside complex (BRL) to a final concentration of approximately 2 mM. The mixture incubated on a rotary shaker at 37° C. for 20 minutes and was then centrifuged at 12000×g for 10 min at 4° C. The aqueous layer was removed and extracted with an equal volume of Tris-saturated phenol:chloroform:isoamyl alcohol (50:50:1). Second and third extractions were done with 1 M Tris-saturated phenol:chloroform (50:50) and chloroform, respectively. The final aqueous layer was mixed with an equal volume of 6 M LiCl and left at −20° C. for at least 4 hours. The precipitate was pelleted at 12,000×g for 20 minutes at 4° C. and resuspended in 0.6 ml water treated with 0.1% diethyl pyrocarbonate (DEPC). The total RNA was reprecipitated with 0.1 volume of sodium acetate and 2.5 volumes ethanol. The final pellet was dissolved in 0.3 ml water treated with 0.1% DEPC.

B. Isolation of Polyadenylated RNA

Polyadenylated RNA was isolated by heating approximately 500 $\mu$g of total RNA in 0.2 to 1.0 ml water to 65° C. for 5 minutes, cooling on ice, and adding 10×sample buffer consisting of: 10 mM Tris pH 7.5; 1 mM EDTA; 5 M NaCl in 0.1% DEPC-treated water to a final concentration of 1×. The treated sample was applied to a column of oligod(T) cellulose prepared according to the manufacturer's instructions (Poly(A)Quik™ mRNA purification kit—Stratagene). The column was washed twice with High Salt Buffer (10 mM Tris pH 7.5; 1 mM EDTA; 0.5 M NaCl) and three times with Low Salt Buffer (10 mM Tris pH 7.5; 1 mM EDTA and 0.1 M NaCl). PolyA mRNA was then eluted from the column with four 200 $\mu$l aliquots of Elution Buffer (10 mM Tris pH 7.5 and 1 mM EDTA) which had been heated to 65° C. RNA concentration was determined spectrophotometrically using absorbance at 260 nm.

EXAMPLE 13

Construction of Lambda gt-11 cDNA Library

A cDNA library was constructed using 4 to 5 $\mu$g of polyadenylated RNA that had been purified twice over an oligo(dT) column. The reagents for construction of cDNA, addition of adapters and ligation of lambda gt-11 arms except [$^{32}$P]dCTP were provided in the Superscript™ Choice System (BRL) and were used according to the manufacturer's instructions.

First strand synthesis was primed using either 0.05 $\mu$g random hexamers plus 0.5 $\mu$g oligo(dT)$_{12-18}$ or 1 $\mu$g oligo (dT)$_{12-18}$ alone. The reaction was carried out in a final volume of 20 $\mu$l (final composition: 50 mM Tris, pH 8.3; 75 mM KCl; 3 mM $MgCl_2$; 10 mM DTT; 500 uM each dATP, dCTP, dGTP, dTTP; primers; mRNA; 10 $\mu$Ci [$^{32}$P]dCTP; 200 U Superscript™ reverse transcriptase/$\mu$g MRNA). The reaction mixture was incubated for 1 hr at 37° C. and then placed on ice.

Second strand synthesis was carried out in a final volume of 150 $\mu$l using 18 $\mu$l of the first strand reaction. The final composition of the reaction was: 25 mM Tris pH 7.5; 100 mM KCl; 5 mM $MgCl_2$; 10 mM $(NH_4)_2SO_4$; 0.15 mM B-NAD+; 250 $\mu$M each dATP, dCTP, dGTP, dTTP; 1.2 mM DTT; 65 U/ml DNA Ligase; 250 U/ml DNA polymerase I; and 13 U/ml RNase H. This reaction mixture was incubated at 16° C. for 2 hr; then 10 U of T4 DNA polymerase was added, and the incubation was continued at 16° C. for an additional 5 minutes. The reaction was put on ice and stopped by adding 10 $\mu$l of 0.5 M EDTA. The mix was extracted with 150 $\mu$l of Tris-saturated phenol:chloroform:isoamyl alcohol (25:24:1). The aqueous layer was removed, and cDNA was precipitated with 0.5 volume 7.5 M ammonium acetate and 3.5 volumes ethanol. The cDNA pellet was washed with 70% ethanol. EcoRI (Not1) adapters were ligated to the cDNA in a reaction mix comprised of 66 mM Tris, pH 7.6; 10 mM $MgCl_2$; 1 mM ATP; 14 mM DTT; 200

μg/ml EcoRI (Not1) adapters; 100 U/ml T4 DNA ligase. The reaction mixture was incubated for 16 hours at 16° C., then heated to 70° C. and placed on ice. The adapted cDNA was phosphorylated by adding 30 U of T4 polynucleotide kinase to the reaction mix and incubating for 30 minutes at 37° C. The kinase was inactivated by heating to 70° C. for 10 minutes. The completed reaction was diluted with 97 μl of TEN buffer (10 mM Tris, pH 7.5; 0.1 mM EDTA; 25 mM NaCl) and placed over a Sephacryl® DNA sizing column prepared according to the manufacturer's directions (BRL). The DNA was eluted with TEN buffer and fractions were collected. Cerenkov counts were obtained for each fraction and the amount of cDNA/fraction was calculated. The column fractions were pooled in order of elution until 50 ng cDNA was collected. The pool was then precipitated with 5 μl yeast tRNA, 0.5 volumes 7.5 M ammonium acetate and 2 volumes ethanol (−20° C.). The resultant pellet was washed with 70% ethanol, dried and ligated to lambda gt-11 arms. The final composition of the ligation reaction was 50 mM Tris pH 7.6; 10 mM $MgCl_2$; 1 mM ATP; 5% PEG 8000(w/v); 1 mM DTT; 100 μg/ml lambda vector EcoRI arms; 10 μg/ml cDNA; and 200 U/ml T4 DNA ligase. This mixture was incubated for 3 hours at room temperature. The cDNA/lambda gt-11 ligation was packaged into infectious lambda phage particles as described above.

EXAMPLE 14

A. Antibody Screening of Lambda gt-11 Library

E. coli strain Y1090 was used as the host for lambda phage infections and was maintained on LB/ampicillin plates consisting of: 1% tryptone (w/v); 0.5% yeast extract (w/v); 0.5% NaCl (w/v); 1.5% agar (w/v); the pH was adjusted to 7.5 before autoclaving, and 100 μg/ml ampicillin added after autoclaving. Cultures were grown for phage infection by incubating a single colony overnight on a rotary shaker at 37° C. in 3 ml LB/maltose broth consisting of: 1% tryptone(w/v); 0.5% yeast extract(w/v); 0.5% NaCl(w/v) and 0.2% maltose(w/v).

B. Pretreatment of Antisera

Antisera were treated with an E. coli lysate prior to screening so as to decrease cross-reaction to E. coli protein. E. coli lysate was prepared from Y1090 cells grown overnight in LB broth at 37° C. on a rotary shaker at 220 rpm. Cells were pelleted by centrifugation at 10,000×g at 4° C. and resuspended in 3 ml Lysate Buffer (50 mM Tris pH 8.0 and 10 mM EDTA). Cells were frozen in a dry ice/ethanol bath and thawed at room temperature; the freeze/thaw process was repeated. The suspension was sonicated 5×10 seconds at output control 4 on a constant duty cycle using a Branson Sonifier 450. Cells were placed on ice for 10 seconds after each pulse. Protein concentration in the lysate was estimated using the Bradford Assay (Bio-Rad) according to the manufacturer's suggestion. Sonicated lysate was stored at −20° C. until needed. The antisera was diluted 10-fold with TBST plus 1% dried milk(w/v) and mixed with 1/20 volume E. coli lysate. This solution was incubated at room temperature on a rotary shaker for two hours.

C. Screening of Lambda Gt-11 Phage Plagues

Recombinant phage diluted to $6×10^3$ pfu in 100 μl of SM was added to 600 μl of an overnight culture of E. coli Y1090 and absorbed at 37° C. for 30 minutes. The cells were then added to 7.5 ml of a 47° C. solution of LB Top Agarose/ $MgSO_4$ (0.1% tryptone(w/v); 0.5% yeast extract(w/v); 0.5% NaCl(w/v); 10 mM $MgSO_4$) and plated on a 140 mm LB agar plate. The plate was incubated at 42° C. for approximately 5 hours until tiny plaques were visible. The plate was then overlaid with a 137 mm nitrocellulose filter which had been saturated with a 10 mM solution of IPTG (isopropyl-B-D-thiogalactopyranoside) and air-dried. Incubation of the plate was continued overnight at 37° C. The filter was removed and washed 3 times for 15 minutes each. All washes were carried out at room temperature on a rotary shaker in TBST. The filters were blocked in TBST plus 5% w/v dried milk (Carnation instant non-fat dried milk) for 30 minutes at room temperature on a rotary shaker. Filters were washed 3×15 minutes and then incubated with a 1:1000 dilution of goat anti-rabbit IgG alkaline phosphatase conjugate (Bio-Rad) in TBST plus 1% dried milk(w/v) for 2 hours. The filters were washed 3×15 minutes and then developed in AP buffer (100 mM Tris pH 9.5; 100 mM NaCl; 5 mM $MgCl_2$) to which was added NBT (nitroblue tetrazolium) to a final concentration of 0.33 mg/ml and BCIP (5-bromo4-chloro-3-indoyl phosphate) to a final concentration of 0.165 mg/ml for 2–5 minutes. The color reaction was stopped by washing the filters with water. Positive plaques were picked to 1 ml SM plus 10 μl chloroform and stored at 4° C. until needed.

Positive plaques were further purified until all the plaques on a filter were positive. Purification rounds were done on 100 mm LB/agar plates with phage titer adjusted to approximately 100 pfu/plate. Positive plaques were confirmed by screening with an affinity-purified antibody at a dilution of 1:100.

EXAMPLE 15

Preparation of Lambda DNA

Phage were adsorbed to 1.5 ml of an overnight culture of E. coli Y1090 at a multiplicity of infection of 0.01 for 30 minutes at 37° C. and then added to 300 ml LB media. The cells were incubated at 37° C. on a rotary shaker about 6 hours (until the cells lysed). One ml chloroform was added to complete the lysis. Cell debris was pelleted by centrifugation at 10,000×g for 10 minutes at 4° C. Lysate was stored at 4° C. until needed.

Lysate was treated with DNase I (final concentration 1 μg/ml) and RNase H (final concentration 5 μg/ml) at 37° C. for one hour. Phage were pelleted by centrifugation for 90 minutes at 27,000 rpm in a Sorvall AH-629 rotor; and the tubes were inverted to drain. Phage pellets were resuspended in 200 μl 0.05 M Tris, pH 8 and were extracted with 200 μl Tris-saturated phenol by vigorous shaking for 20 minutes. The mixture was spun in a microcentrifuge, and the aqueous layer saved. The aqueous layer was extracted with phenol and then extracted twice with 200 μl chloroform. DNA was precipitated with 0.1 volume 3 M sodium acetate and 6 volumes ethanol at room temperature. DNA was pelleted in a microcentrifuge, washed with 70% ethanol, dried and resuspended in 100 μl TE pH 8.0 (10 mM Tris; 1 mM EDTA).

EXAMPLE 16

Screening of EMBL3 Genomic Library

The EMBL3 genomic library was plated for screening with $^{32}$P-labeled DNA probes. Approximately 10,000 plaques were plated and transferred to nitrocellulose for hybridizations. Filters were prehybridized for 2 hours and hybridized overnight in hybridization buffer in the presence of a DNA probe labeled with $^{32}$P-dCTP (Oligolabeling Kit, Pharmacia). For the selection of EMBL-1, the DNA probe consisted of the EcoRI cDNA insert of lambda gt-11 2-9 which was identified using the antibody to the 235 kD protein. Filters were washed using the protocol employed for Southern hybridizations, and positive plaques were identified after an overnight exposure to film. DNA from positive EMBL-3 phage was prepared as described.

EXAMPLE 17
Sequencing Strategy and Analysis

A series of overlapping subclones from the genomic EMBL1 clone, which contained the triol PKS gene, were constructed in M13mp18 and M13mp19. Nested deletions of some of the clones were obtained using the Cyclone I Biosystem (International Biotechnologies, Inc., New Haven, Conn.). Single stranded DNA was purified by precipitation with 20% polyethylene glycol-2.5 M NaCl followed by phenol extraction and ethanol precipitation. The nucleotide sequence of both strands of the DNA was determined using the USB Sequenase Version 2.0 DNA Sequencing Kit (United States Biochemicals, Cleveland, Ohio). The −40 sequencing primer from the kit or custom synthesized oligonucleotides were used to prime the reactions. Regions containing GC compressions were resequenced using dITP in place of dGTP. The sequencing reactions were separated on 6% polyacrylamide denaturing gels. The genomic M13 clones were resequenced using a 373A DNA Sequencer (Applied Biosystems, Inc.) for verification. Introns were identified by sequence analysis of cDNA. The RNA was prepared from a 16 hr culture grown in GP9 medium, and cDNA was synthesized using AMV reverse transcriptase. Custom synthesized oligonucleotides were used to amplify short overlapping stretches of the cDNA by PCR. The PCR conditions, reagents, and product purification were performed as described for PCR with genomic DNA in the PCR/Sequencing Kit PCR Amplification Module manual (Applied Biosystems, Inc., Foster City, Calif.). The PCR were performed using a Perkin Elmer GeneAmp PCR system 9600. The PCR products were sequenced as described in the Taq DyeDeoxy Terminator Cycle Sequencing Kit manual (Applied Biosystems, Inc.), and sequencing reactions were analyzed using the 373A DNA Sequencer. All sequence analyses and manipulations were performed using GeneWorks (IntelliGenetics, Inc., Mt. View, Calif.) on a Macintosh computer (Apple Computer, Inc., Cupertino, Calif.).

EXAMPLE 18
A. Construction of pTPKS100

The transformation vector pTPKS100 contains the polyketide synthase gene responsible for the synthesis of the nonaketide backbone of the triol structure, the phleomycin resistance gene for selection in *A. terreus* and the ampicillin resistance gene for selection in *E. coli*.

The vector was constructed from the pUT715 vector (Cayla, Toulouse Cedex, France) which contains the phleomycin resistance marker from *S. hindustanus* and the termination sequence from the Cyc1 gene in *S. cerevisiae*. The pUT715 vector was digested with BamHI and EcoRv. The β-tubulin gene promoter was inserted in front of the phleomycin marker gene as follows. The β-tubulin promoter was removed from pTL113 by digestion with EcoRI, filling with Klenow fragment, and releasing the fragment from the vector with a BgIII digest. The β-promoter was ligated into the pUT715 vector to form pCLS7. The β-tubulin promoter, phleomycin marker and Cyc1 terminator were removed from PCLS7 by digestion with Ndel and BgIII followed by filling in the sites, and ligating into the SmaI site of the Bluescript vector (Strategene). This vector was named pL0A.

The polyketide synthase gene was inserted into pL0A in a two step process. The promoter and 5'-end of the PKS gene was obtained from EMBL-1 as a Kpnl to EcoRI fragment and ligated into pL0A which had been digested with KpnI and EcoRI. This vector was named TPKS A. The 3' end of the PKS gene was then added to the construction by digesting TPKS A with EcoRI and ligating in the 3' EcoRI gene fragment isolated from EMBL-1. The resulting vector was named pTPKS 100.

Transformation of a lovastatin-nonproducing strain with pTPKS100 restored lovastatin production. Transformation of ATCC 20542 (a lovastatin-producing strain) increased lovastatin production relative to untransformed cells.

EXAMPLE 19
Transformation of *A. terreus* ATCC 20542

To determine whether increasing the copy number of the PKS gene in a lovastatin-producing strain would result in an increase in the amount of lovastatin produced, a set of experiments were designed and carried out using the *A. terreus* ATCC 20542. ATCC 20542 was transformed with pTPKS-100. Transformants were checked by PCR to confirm that they contained the phleomycin marker and were true transformants. Following single spore isolation, the confirmed transformants were fermented and lovastatin production was measured by HPLC. The highest producer of single isolates, strain 3-17-7#7, was 32% greater for the transfornant than for the parent.

EXAMPLE 20
Characterization of the TPKS Protein Sequence

Splicing of the introns from the DNA sequence and translation of the 9114 nucleotide open reading frame results in a protein of 3038 amino acids with a molecular weight of 269,090 daltons. The final amino acid sequence of the TPKS protein is shown in FIG. 2. The features discussed below are presented with their amino acid position noted in the following table.

| TPKS PROTEIN FEATURES | | |
|---|---|---|
| Description | Motif | Amino Acid |
| Keto-acyl synthase | Cysteine | 181 |
| Acetyl/Malonyl Transferase | GXSXG SEQ ID NO: 4 | 654–658 |
| Dehydratase | HXXXGXXXXP SEQ ID NO: 5 | 985–994 |
| Methyl Transferase | GXGXG SEQ ID NO: 6 | 1446–1450 |
| Enoyl Reductase | SXGXXS SEQ ID NO: 7 | 1932–1937 |
| Keto Reductase | LXGXXG SEQ ID NO: 8 | 2164–2169 |
| Acyl Carrier Protein | Serine | 2498 |

Inspection of the TPKS amino acid sequence for active site residues and motifs known to be associated with polyketide synthases and fatty acid synthase (FAS) activities resulted in the identification of candidates for expected functional sites. These sites were identified by carrying out searches for amino acid sequences and amino acid homologies using the Intelligenetics Gene Works program. A graphic view of the open reading frame of the protein and the overall placement of the TPKS peptide sequences obtained by partial sequence analysis of TPKS peptides and PKS activities established by alignments and is shown in the figures. Except for the presence of a methyl transferase, not present in FAS, the succession of activities on the TPKS protein is the same as that observed for the rat FAS protein. The alignments carried out on regions of the TPKS, the rat FAS, and the 6-methylsalicyclic acid synthase (6-MSAS) of *Penicillium patulin* in order to identify the best candidate for each of the activities are also presented in the figures.

EXAMPLE 21
Identification of the Keto Acyl Synthase Region

The most 5' site is the β-keto acyl synthase (KAS), also known as the condensing enzyme. This activity is centered around the active site cysteine to which the acyl chain is attached prior to the entry and condensation of the incoming acyl unit. The region shown in the Keto Acyl Synthase Alignment figure contains 30% homology when compared to both the rat FAS and 6-MSAS sequences. However, the TPKS KAS region is most closely related to the rat FAS sequence, exhibiting 49% homology over this region compared to 41% to 6-MSAS.

EXAMPLE 22

Identification of the Acetyl Malonyl Transferase

Proceeding towards the COOH terminus, the next functional site identified is the acetyl/malonyl transferase, which is responsible for accepting the incoming substrate for transfer to either the active thiol of the beta-keto synthase (if a priming acetyl unit) or to the active site thiol of the ACP-pantetheine-SH if a malonyl building block. The identification of the acetyl/malonyl transferase site was found by searching for the GXSXG SEQ ID NO:4 motif found in many proteins with an active site serine (Wakil, S. J., 1989, Biochemistry, 28: 4523–4530). The conservation of this motif in the TPKS protein was observed beginning at amino acid 654, as shown in the figures.

EXAMPLE 23

Identification of the Dehydratase

The next site in common with the FAS protein is the dehydrates. The dehydratase motif consistently found not only in the rat FAS, but the 6-MSAS and the erythromycin SU4 as well consist of a "HXXXGXXXXP" SEQ ID NO:5 sequence (Donadio, S. and Katz, L., 1992, Gene, 111, 51–60.). The homology outside of this signature sequence is very weak.

EXAMPLE 24

Identification of the Envoy and Keto Reductase

The next two activities identified on the rat FAS protein are the enoyl reductase (ER) and keto reductase (KR). In general, the ER and KR are identified by searching for the GXGXXG/A SEQ ID NO:9 motif which is proposed to represent the pyridine nucleotide binding site in many proteins (Wierenga, R. K. and Hol, W. G. J., 1983, Nature, 302, 842–844). An identical match to this motif has been identified in the rat FAS for both the KR and ER (Witkowski, V., et al., 1991, Eur. J. Biochem., 198, 571–579). Inspection of the TPKS protein identified three matches to the motif. The first begins at position 321 between the β-keto synthase and acetyl/malonyl transferase functions. However, this is not considered to be a good candidate for either of the reductase activities due to its 5' position in the protein and because it lies in a region which is highly homologous to rat FAS. The GXGXXG SEQ ID NO:9 motif is seen again at position 1446–1451, however, this is considered to be part of the methyl transferase domain. The third time the motif occurs is at position 2438 which lies 60 amino acids 5' of the ACP active site serine. A similar GXGXXG SEQ ID NO:9 motif is seen in the rat FAS at 125 amino acids prior to the ACP and in 6-MSAS 129 amino acids 5' of the ACP. Since candidates for the NAD(P) binding sites of the KR and ER were not observed in the TPKS protein, homology searches were performed between the regions of the rat FAS which contain these sites and similar regions of the TPKS protein.

As shown in the Enoyl Reductase Alignment, the region of the TPKS protein which lies between the dehydratase and the keto reductase and shows the best alignment to the rat FAS enoyl reductase does not bear a strong homology to the GXGXXG SEQ ID NO:9 motif or to the region in general. A much stronger homology is evident between the ER domain of SU4 of Erythromycin AH and the rat FAS sequence. The Keto Reductase Alignment of the rat FAS and 6-MSAS keto reductase regions with the TPKS shows slightly higher homology, with 6 out of 30 amino acids surrounding the glycine-rich region conserved between all genes and 13 of 30 conserved between TPKS and either FAS or 6-MSAS.

The glycine-rich segment is part of an overall structural motif for pyridine-nucleotide binding domains in many proteins (Wierenga, ibid.; Scrutton, N. S., et al., 1990, Nature, 343, 38–43; Ma, Q., et al., 1992, 267, 22298–22304; Hanukoglu, I., and Gutfinger, T., 1989, Eur. J. Biochem., 180, 479–484). This structural motif consists of a beta sheet-turn-alpha helix where the glycine rich region codes for the strong turn signal in the middle. In addition, downstream acidic or basic amino acids are positioned to bind to the phosphate (NADP) or hydroxyl group (NAD) on the 2' ribose position. This is depicted in a Chou Fasman analysis of the secondary structure of horse alcohol dehydrogenase as a model NADP binding protein. The analysis of the structural characteristics using the Chou Fasman algorithm indicate that this structural motif is conserved in the rat FAS ER and KR domains, (Witkowski, A., 1991, Eur. J. Biochem., 198, 571–579). The structural predictions of the amino acid sequence of the TPKS ER and KR, as well as the 6MSAS KR, show variations of the model. All predicted structures show a β sheet leading into a turn region, even when amino acid homologies are not strong. It has been suggested that deviations from the structural model may reflect differences in substrate specificity (Ma, Q., supra). It is possible that these structural variations are important in the programming of the PKS, resulting in different levels of reduction of the beta-keto group during successive cycles of the biosynthesis of the triol precursor. Consistent throughout the alignments are the presence of basic amino acids at position 20 to 23 amino acids from the "glycine rich" regions identified by the homology searches. The structural similarities and the presence of these basic amino acids suggest that these regions do indeed represent the keto and enoyl reductases of the TPKS protein.

EXAMPLE 25

Identification of the Acyl Carrier Protein

The last active site identified by alignment of the rat FAS with the TPKS is the acyl carrier protein (ACP) active site serine which binds the 4'-phosphopantetheine prosthetic group. While only 6 out of 30 amino acids surrounding the active site serine are conserved over TPKS, rat FAS and 6-MSAS, a higher degree of homology (13 of 30 amino acids) is observed between TPKS and either rat FAS or 6-MSAS.

EXAMPLE 26

Identification of the Methyl Transferase

One activity identified within the reading frame of the TPKS protein which is not present in rat FAS is the methyl transferase responsible for transfer of the methyl group from S-adenosylmethionine (SAM) to the polyketide chain at position 6. A comparison of both eucaryotic and procaryotic methyl transferases responsible for the methylation of RNA, DNA, and protein substrates has identified a sequence motif thought to be part of the SAM-binding domain (Ingrosso, D. et al., 1989, J. Biol. Chem., 264, 20131–20139; Wu, G. et al., 1992, J. Gen. Micro, 138, 2101–2112). The binding motif and its alignment with the proposed methyl transferase of the TPKS are shown in the figures.

The absence of a methyl group in compactin suggests that the methyl transferase domain may be absent or altered in the compactin PKS.

EXAMPLE 27

A. Transformation of *Monascus ruber*

Cultures of *M. ruber* strains M4681 AND M82121 are grown, spheroplasted and transformed essentially according to the procedures described above. Petri dishes are incubated at 28° C. and 65% humidity for 7–10 days before transformed colonies are picked.

B. Fermentation of Monascus

The transformed cultures are grown aerobically in a medium containing 7% glycerol, 3% glucose, 3% meat extract, 0.8% peptone, 0.2% NaNO3, and 0.1% $MgSO_4.7H_2O$ at 25 degrees C. for 10 days (Kimura et al., 1990. "Biosyn. of Monacolins, Conversion of Monacolin J. To Monacolin K (Mevinolin)", *J. of Antibiotics*, Vol. XLIII No. 12, 1621–1622). *M. ruber* M82121 is grown aerobically at 25° C. for 11 days in a medium containing 11% glycerol, 1% glucose, 5% soy bean powder, 0.8% peptone, 0.1% $NaNO_3$, 0.05% $Zn(NO_3)_2$, and 0.5% olive oil (pH 6.5) (Endo, et al., "Dihydromonacolin L and Monacolin X, New Metabolites Those Inhibit Cholesterol Biosynthesis", *J. Antibiot.*, Vol. XXXVIII No. 3, 321–327). The culture broth is extracted with a solvent such as methanol or dichloromethane, concentrated and analyzed by methods such as HPLC. By comparison with an untransformed host or a *M. ruber* culture containing pL09 without the TPKS genes, the TPKS100 containing host or a derivative thereof produces increased levels of lovastatin, triol, monacolin, dihydromonacolin L or monacolin X.

EXAMPLE 28

A. Transformation of *Paecilomyces viridis*

*P. viridis* strain L-63 is grown, spheroplasted and transformed essentially according to the procedures described above. Cells are transformed with pTPKS100 or a derivative thereof. An example of such a derivative is one in which the DNA encoding the methyl transferase activity of the TPKS protein is altered such that an active methyl transferase is not produced. Petri dishes are incubated at 28° C. and 65% humidity for 7–10 days before transformed colonies are picked.

B. Fermentation of Paecilomyces

*P. viridis* L-63 is grown aerobically in a medium containing 7% glycerol, 3% glucose, 3% meat extract, 0.8% peptone, 0.2% $NaNO_3$, and 0.1% $MgSO_4.7H_2O$ at 25° C. for 4 to 10 days (Kimura et al., supra). The culture broth is extracted with a solvent such as methanol or dichloromethane and concentrated by evaporation if necessary. By comparison with an untransformed host or a *P. viridis* culture containing pL0A without the TPKS genes, the transformed host can be shown to ferment increased levels of ML-236A and compactin.

EXAMPLE 29

A. Transformation of *Penicillium citrinum*

A suitable culture of *P. citrinum* (e.g., Nara, et al., 1993. "Development of a transformation system for the filamentous, ML-236B (compactin)—producing fungus *Penicillium citrinum*". *Curr. Genet.*, 23, 28–32) is transformed with pTPKS100 or an appropriate derivative thereof using conventional methods.

B. Fermentation of *P. citrinum*

The transformed culture is maintained on yeast-malt extract agar slant (4 g/l dextrose, 10 g/l malt extract, 4 g/l yeast extract, agar 20 g/l, pH 7 prior to sterilization). The slant is washed and used to inoculate to flasks containing KF seed medium (10 g/l $CaCl_2$, 5 g/l corn steep liquor, 40 g/l tomato paste, 10 g/l oatmeal, 10 g/l cerelose, 10 ml trace element per liter, pH 6.8; trace elements consist of 1 g $FeSO_4.7H_2O$ 1 g $MnSO_4.4H_2O$, 25 mg $CuCl_2.2H_2O$, 100 mg $CaCl_2$, 56 mg $H_3BO_3$, 19 mg $(NH_4) 6Mo7O24.H_2O$, 200 mg $ZnSO_4.7H_2O$ in liter of $dH_2O$). The KF seed flasks are incubated for about 3 days at about 28° C. and 220 rpm. Approximately 1.5 ml is used to inoculate 40 ml of LM production medium per 250 ml flask. LM medium contains 20 g/l dextrose, 20 ml/l glycerol, 10 g/l ardamine pH, 20 g/l malt extract, 8 mg/l $CoCls.6H_2O$ and 0.25% polyglycol P2000, pH 7.0. After 5 to 10 days at 25° C. on a shaker, the broth is collected, extracted and concentrated. The transformed culture produces more compactin and dihydrocompac;tin than does the untransformed parent culture.

EXAMPLE 30

Cloning of TPKS cDNA into a Mammalian Expression Vector

TPKS cDNA expression cassettes are ligated at appropriate restriction endonuclease sites to the following vectors containing strong, universal mammalian promoters:

Cassettes containing the TPKS cDNA in the positive orientation with respect to the promoter are ligated into appropriate restriction sites 3' of the promoter and identified by restriction site mapping and/or sequencing. These cDNA expression vectors are introduced into various host cells by standard methods including but not limited to electroporation, or chemical procedures (cationic liposomes, DEAE dextran, calcium phosphate). Transfected cells and cell culture supernatants can be harvested and analyzed for TPKS expression as described below.

Vectors used for mammalian transient expression may be used to establish stable cell lines expressing TPKS.

EXAMPLE 31

Cloning of TPKS cDNA into a Baculovirus Expression Vector for Expression in Insect Cells Baculovirus vectors, which are derived from the genome of the AcNPV virus, are designed to provide high level expression of cDNA in the Sf9 line of insect cells. Recombinant baculoviruses expressing TPKS cDNA are produced essentially by standard methods (*InVitrogen Maxbac Manual*). The TPKS cDNA constructs are ligated into the polyhedrin gene in a variety of baculovirus transfer vectors including but not limited to pAC360 and the BlueBac vector (InVitrogen). Recombinant baculoviruses are generated by homologous recombination following co-transfection of the baculovirus transfer vector and linearized AcNPV genomic DNA[Kitts, P. A., *Nuc. Acid. Res.*, 18, 5667 (1990)] into Sf9 cells. Following plaque purification, TPKS expression is measured by the assays described above.

Authentic, enzymatically-active TPKS is found in the cytoplasm of infected cells. Active TPKS is extracted from infected cells under native conditions by hypotonic or detergent lysis.

EXAMPLE 32

Cloning of TPKS cDNA into a yeast expression vector

Recombinant TPKS is produced in the yeast *S. cerevisiae* following the insertion of the optimal TPKS cDNA cistron into expression vectors designed to direct the intracellular or extracellular expression of heterologous proteins. In the case of intracellular expression, vectors such as EmBLyex4 or the like are ligated to the TPKS cistron [Rinas, U. et al., *Biotechnology* 8, 543–545 (1990); Horowitz B. et al., *J. Biol. Chem.*, 265, 4189–4192 (1989)]. For extracellular expression, the TPKS cistron is ligated into yeast expression vectors which fuse a secretion signal (a yeast or mammalian peptide) to the $NH_2$ terminus of the TPKS protein [Jacobson, M. A., *Gene*, 85, 511–516 (1989); Riett L. and Bellon N., Biochem., 28, 2941–2949 (1989)].

EXAMPLE 33
Use of TPKS for in vitro Production of HMG-CoA Inhibitors

Recombinant proteins, including complex proteins, can be overexpressed in a heterologous cells (e.g., Roberts et al., 1993, "Heterologous expression in *E. coli* of an intact multienzyme component of the erythromycin-producing polyketide synthase". *Eur J. Biochem,* 214, 305–311). If the recombinant protein is produced in an inclusion body, renaturation of the desired protein is carried out prior to enzymatic assay (Roberts, 1993).

A suitable host cell is transformed with a vector encoding the TPKS gene. The transformed host cell is grown under conditions that permit the expression of TPKS. The expressed TPKS is isolated and partially purified. The recovered active TPKS enzyme can be added to a reaction mixture containing acetyl-CoA or other charged acyl compounds, appropriate cofactors, and buffer. Incubation of the system can result in the formation of HMG-CoA reductase inhibitors.

EXAMPLE 34
Cloning of other PKS genes using TPKS gene

The cross hybridization of the DNA representing portions of the TPKS gene to genomic DNA isolated from other organisms such as *M. ruber* or *P. citrinum,* makes it possible to clone the homologous genes from the parent organisms. To do this, a genomic library of *M. ruber* or *P. citrinum* was constructed from genomic DNA according to conventional methods. Using, for example, an EMBL vector, an EMBL genomic library was prepared, plated and screened by hybridization with a $^{32}$P-labeled DNA probe consisting of the PstI fragment from the TPKS gene. The PstI fragment contains the keto synthase sequence of the gene. Positive plaques were selected and subjected to additional screening until a purified cross-reacting plaque was selected. The DNA contained in the positive clone is further characterized by physical methods such as restriction mapping, Southern hybridization and DNA sequencing. The function of the defined gene is characterized by cloning the gene in an appropriate transformation vector and transforming a lovastatin non-producing strain with the vector. In the case of *M. ruber,* the cross-reacting PKS would be expected to restore production of Monacolin K (lovastatin) while introduction of a functional *P. citrinum* PKS would result in production of compactin.

EXAMPLE 35
Homology of *A. terreus* TPKS to other strains

A large segment of the 5' end of the *A. terreus* TPKS gene containing the keto synthase region was used to look for cross-hybridization of this region to other strains, including *M. ruber, P. citrinum* and *P. brevicompactum.* The homology was examined by Southern analyses with two probes. The Southern showed cross-reaction to all three strains.

The first probe was the PstI fragment, an 800 bps probe which spans the KAS active site. This probe contains intron I 5' of the active site cysteine in addition to the entire KAS region. This probe was used to detect homology in all three strains. *A. terreus* displayed the profile of cross-reacting bands expected from the restriction map. *M. ruber,* another lovastatin-producing organism, and *P. citrinum,* a compactin-producing organism, showed different but strong hybridizations to the probe.

The second probe was a synthetic oligonucleotide probe having the following sequence:
5' G ATA C G G C ATG C AG C T C G T C G T T G G T-TGCCGTTCATCTGGCT GCA3' (SEQ ID NO:3). Although the hybridization signal to this probe was weaker than the hybridization to the first probe, the results confirm the observations made with the PstI fragment.

When a 3' end cDNA probe was used, cross reaction to all three strains was observed. Single cross-reacting bands in many of the digests indicate that only one gene is being detected in the genomic DNA of each strain. These data suggest that *M. ruber* and *P. citrinum* contain a gene with substantial homology to the TPKS gene of *A. terreus.*

EXAMPLE 36
Use of mutagenized TPKS

The DNA encoding TPKS is mutagenized using standard methods to produce an altered TPKS gene. Host cells are transformed with the altered TPKS to produce altered triol polyketides or altered polyketides with therapeutic use. The altered TPKS protein may be isolated and purified.

What is claimed is:

1. A purified and isolated nucleic acid molecule having a nucleotide sequence encoding the triol polyketide synthase of *Aspergillus terreus* having the amino acid sequence of SEQ ID NO:2.

2. An expression vector comprising the DNA molecule of claim 1.

3. A host cell transformed with the expression vector of claim 2.

4. A process for producing HMG-CoA reductase inhibitors, comprising:
   (a) transforming a cell with the DNA molecule of claim 1 wherein said cell is selected from the group consisting of cells of *Aspergillus terreus, Monascus ruber, Penicillum citrinum, Penicillum brevicompactum, Hypomyces chrysospermus, Paecilomyces viridis, Paecilomyces sp.* M2016, *Eupenicillium sp.* MM603, *Trichoderma longibrachiatum* M6735 and *Trichoderma pseudokoningii* M6828;
   (b) cultivating the transformed cell under conditions that permit the expression of the DNA molecule; and
   (c) recovering the HMG-CoA reductase inhibitor.

5. The process of claim 4 wherein the HMG-CoA reductase inhibitors are selected from the group consisting of lovastatin, triol and compactin.

6. A method of isolating DNA encoding polyketide synthase, comprising:
   (a) hybridizing the DNA of claim 1 to a sample containing DNA encoding polyketide synthase to form a complex; and
   (b) purifying the complex.

7. The method of claim 6 wherein the sample is derived from a microorganism, the microorganism being selected from the group consisting of *Aspergillus terreus, Monascus ruber, Penicillum citrinum, Penicillum brevicompactum, Hypomyces chrysospermus, Paecilomyces viridis, Paecilomyces sp.* M2016, *Eupenicillium sp.* MM603, *Trichoderma longibrachiatum* M6735 and *Trichoderma pseudokoningii* M6828.

* * * * *

SEQUENCE LISTING

<160> NUMBER OF SEQ ID NOS: 41

<210> SEQ ID NO 1
<211> LENGTH: 11561
<212> TYPE: DNA
<213> ORGANISM: TPKS DNA

<400> SEQUENCE: 1

```
ctgcagtcaa cggatcactt accattgctg tcgccaaaaa tatccgtgat aatcccgctg      60
gcttcattgg caagaggctt gacgtacttg ggagcttggg tctggaactg gttcataacc     120
accttggtga tgagatgtgc atccctcgtg acttccttga atccatcgaa tccgggaaga     180
tgagagtgaa agtcctgatg agagcacgaa gatcagtaag tcaggtcctc acagcggaag     240
cagttgcaaa gaacggtgga ctccttaccg tgcccaagaa cttgtacata cagagctctt     300
tcatcttgcg aaactcatcg gccatagagg agggaagaat ggtgcagtac ccagagtcga     360
```

-continued

```
ctatgaaccg aatgggctta tcattttgcg agaaccagct ctcaatccat gacggtgcat    420
tcgcatcaaa atcccgtttg ccctcatgg tcgtcagttc ccaccatgtt ttcggattga     480
acaccggcag atcagatctc cggccactcg agcacaggta agaagaagg catagtagcc     540 ccgcactggt agtgaccaag ggcgcaaacc acgagccatg ttgctgcgtg tcattccaag    600
ccagcgacag aaggtggtgc ggctgtgtga gcgcgtcgac agtcatggct aggagaccag    660
gtgtggttga gggataagat atcgagagtg atgtgagcaa aagatccggg aaggtcgcg     720 aaggaaaggc cgtctctctt accaagaaag tctgttccct atcatgcaat cacccgcttgc   780 tgtacggtgg tgatgatgct gggatggtgg tgggtcccca ccgaataacg ccggacagct    840
gttgaagccg aatgacgccg gcaggccaaa agaaccctac cttcacttac tcaatcggcg    900
cttcccctcc tatcaccaaa tcggatgtaa atggacgggc cttaatagcg accggccggg    960
ccgggaatcc ccaaacgtag atagataggc atagacccga atctttggc ccggcataca    1020 tgagcacagg aagtttcacg cgacggcgcc tttcctgcct cagcttcaat ccaagctcac   1080
gagttctgtc gcctctatca gtcgtgcaat tgtcctactg caaacagcat ggctcaatct   1140
atgtatccta atgagcctat tgtcgtggtc ggcagtggtt gtcgcttccc tggtgacgcc   1200
aacacaccct ccaagctctg ggagctactc cagcatcctc gcgatgtgca gagtcgaatc   1260
cccaaagaac gatttgacgt cgacacattt tatcacccgg acgggaagca ccacgggcga   1320
acaaatgcac cctacgccta tgttctccaa gacgatctgg gcgccttcga tgcggccttc   1380
ttcaatatcc aggctggaga ggccgagagt atggaccccc agcaccggct gttgctggag   1440
acggtgtacg aggccgtaac gaatgctgga atgcgtatcc aggatctgca gggaacttcg   1500
actgctgttt acgtcgggt gatgacgcac gactatgaga ctgtctcaac ccgcgacctg   1560
gagagcatcc ccacctactc ggcgacgggt gtcgcggtca gtgttgcgtc caaccgcatc   1620
tcgtattttt ttgactggca tggaccaagt gtaagtcacc caatatcgtg tagcagtcta   1680
atcatgctct aacggaccgg gatggttgaa agatgacgat cgatacggca tgcagctcgt   1740
cgttggttgc cgttcatctg gcggtgcaac agctacggac gggtcaaagc tccatggcaa   1800
ttgctgcggg tgcgaatctg attctgggc ccatgacatt cgtccttgaa agcaaattga    1860
gcatgctatc cccctcgggt cgatcccgca tgtgggacgc cggagctgac ggctatgcca   1920
gaggcgtgag tgtttcttga gctcgtagat gacagttccc atcgctgacc gtgatcagga   1980
agctgtttgc tctgtagtgt tgaagacatt gagtcaagcc ttgcgcgatg gggacacgat   2040
tgaatgtgtc atccgagaaa ctggggtgaa tcaagatggc cgaacgaccg gaattacgat   2100
gccgaaccat agtgctcagg aggcactcat caaggctacc tacgcccagg ctggccttga   2160
catcaccaag gccgaggaca ggtgccaatt cttcgaggct catggtcagc aaagagaacc   2220
tgttctgttg gcgccctgca gctgacattc gtatgatagg gactggtact ccggccggag   2280
atccccagga ggcggaggcc attgcaacag ccttcttcgg ccacgagcag gtagcacgca   2340
gcgacggaaa cgagagggcc cctctgttcg tgggcagtgc gaaaactgtt gtcgggcaca   2400
ccgagggcac ggccggtctg gctggtctca tgaaggcgtc gttcgctgtc cgccatgggg   2460
taatcccccc caacctgctg ttcgacaaaa tcagcccgcg agtcgcccca ttctataaaa   2520
acctgaggat tccgacagaa gctacccaat ggccagctct cccacccgga caaccgcgcc   2580
gcgccagtgt caactccttt ggtaagcgag gattgcccgg aggaaccctc acaagtactc   2640
gaattaatgc taactgaacc gcgccgatgg acaggattcg gcggcacgaa tgcgcatgcc   2700
attattgagg aatacatgga gccagagcaa aaccagctgc gagtctcgaa taatgaggac   2760
```

| | |
|---|---|
| tgcccaccca tgaccggtgt cctgagttta cccttagtcc tctcggcgaa gtcccagcgc | 2820 |
| tccttaaaga taatgatgga ggagatgctg caattccttc agtctcaccc cgagatacac | 2880 |
| ttgcacgacc tcacctggtc cttactgcgc aagcggtcag ttctacccct ccgccgggct | 2940 |
| attgtcggcc atagtcatga aaccatccgc cgggcttlgg aggatgccat cgaggatggt | 3000 |
| attgtgtcga gcgacttcac tacggagtc agaggccagc atcggtgtt gggaatcttc | 3060 |
| accgggcagg gggcgcagtg gccggggatg ttaaagaatc tgatagaggc atcgccatat | 3120 |
| gtgcggaaca tagtgaggga gctggacgac tccctgcaga gcttgccgga aaaataccgg | 3180 |
| ccctcgtgga cgctactgga ccagttcatg ctagaaggag aggcctccaa cgtccaatat | 3240 |
| gctactttct cccagccatt atgctgcgcg gtgcaaattg tcctggtccg tctccttgaa | 3300 |
| gccgcgagaa tacgattcac ggctgttgtt ggacatagct ccggcgaaat tgcttgcgcc | 3360 |
| tttgctgccg ggctcatcag tgcctcgttg gcgattcgga ttgcttactt acgtggagtc | 3420 |
| gtctcggcag ggggcgccag aggcacaccg ggagccatgt tggccgccgg gatgtccttt | 3480 |
| gaggaagcac aagagatctg cgagttggat gcctttgagg gccgcatctg cgtggctgcc | 3540 |
| agcaattccc cagacagtgt aactttctct ggcgacgcga acgcaattga tcacctgaag | 3600 |
| ggcatgttgg aggatgagtc cacttttgcg agactgctca aggtcgatac agcgtaccac | 3660 |
| tcgcatcata tgcttccatg tgcagaccca tatatgcaag ccctagaaga gtgtggttgt | 3720 |
| gctgttgccg atgcaggttc cccagccgga agtgtaccct ggtattcgtc cgtggacgcc | 3780 |
| gagaacaggc aaatggcagc aagagacgtg accgccaagt actggaaaga taacttagta | 3840 |
| tctccggtgc tattctccca cgcagtgcag cgggcagtcg tcacgcacaa ggcgctggat | 3900 |
| atcgggattg aagtgggctg tcacccagct ctcaagagcc catgcgtcgc caccatcaag | 3960 |
| gatgtcctat ctggggttga cctggcgtat acaggttgct tggagcgagg aaagaatgat | 4020 |
| ctcgattcat tctctcgagc actggcatat ctctgggaaa ggtttggtgc ctccagtttc | 4080 |
| gatgcggacg agttcatgcg tgcagtcgcg cctgatcggc cctgtatgag tgtgtcgaag | 4140 |
| ctcctaccgg cctatccatg ggaccgctct cgtcgctact gggtggaatc ccgagcaact | 4200 |
| cgccaccatc ttcgagggcc caagccccat cttctattag gaaagctctc cgaatacagc | 4260 |
| actccgctaa gcttccagtg gctgaatttt gtgcgcccac gagacattga atggcttgat | 4320 |
| ggacatgcat tgcaaggcca gactgtcttc cctgcggccg gctatatcgt catggcaatg | 4380 |
| gaagcagcct taatgattgc tggcacccac gcaaagcagg tcaagttact ggagatcttg | 4440 |
| gatatgagca ttgacaaggc ggtgatattt gacgacgaag acagcttggt tgagctcaac | 4500 |
| ctgacagctg acgtgtctcg caacgccggc gaagcaggtt caatgaccat aagcttcaag | 4560 |
| atcgattcct gtctatcgaa ggagggtaac ctatccctat cagccaaggg ccaactggcc | 4620 |
| ctaacgatag aagatgtcaa tcccaggacg acttccgcta gcgaccagca ccatcttccc | 4680 |
| ccgccagaag aggaacatcc tcatatgaac cgtgtcaaca tcaatgcttt ctaccacgag | 4740 |
| ctgggggttga tggggtacaa ctacagtaag gacttccggc gtctccataa catgcaacga | 4800 |
| gcagatcttc gagccagcgg caccttagac ttcattcctc tgatggacga gggtaatggc | 4860 |
| tgtcctctcc tgctgcatcc tgcatcattg gacgtcgcct tccagactgt catcggcgca | 4920 |
| tactcctccc caggtgatcg gcgtctacgc tgtctgtatg tacccactca cgttgatcgc | 4980 |
| atcacacttg tccatcccct ttgcctggca acggctgagt ccggatgcga gaaggttgcc | 5040 |
| ttcaatacta tcaatacgta cgacaaggga gactacttga gcggtgacat tgtggtgttt | 5100 |

-continued

```
gacgcggagc agaccaccct gttccaggtt gaaaatatta cttttaagcc cttttcaccc    5160
ccggatgctt caactgacca tgcgatgttt gcccgatgga gctggggtcc gttgactccg    5220
gactcgctgc tggataaccc ggagtattgg gccaccgcgc aggacaagga ggcgattcct    5280
attatcgaac gcatcgtcta cttctatatc cgatcgttcc tcagtcagct tacgctggag    5340
gagcgccagc aggcagcctt ccatttgcag aagcagatcg agtggctcga caagtcctg     5400
gccagcgcca aggagggtcg tcacctatgg tacgaccccg ggtgggagaa tgatactgag    5460
gcccagattg agcacctttg tactgctaac tcctaccacc ctcatgttcg cctggttcag    5520
cgagtcggcc aacacctgct ccccaccgta cgatcgaacg gcaacccatt cgaccttctg    5580
gaccacgatg ggctcctgac ggagttctat accaacacac tcagcttcgg acccgcacta    5640
cactacgccc gggaattggt ggcgcagatc gcccatcgct atcagtcaat ggatattctg    5700
gagattggag cagggaccgg cggcgctacc aagtacgtgt tggccacgcc ccagctgggg    5760
ttcaacagct acacatacac cgatatctcc accggattct tcgagcaagc gcgggagcaa    5820
tttgcccct tcgaggaccg gatggtgttt gaacccctcg atatccgccg cagtcccgcc     5880
gagcagggct tcgagccgca tgcctatgat ctgatcattg cctccaatgt gctacatgcg    5940
acacccgacc tagagaaaac catggctcac gcccgctctc tgctcaagcc tggaggccag    6000
atggttattc tggagattac ccacaaagaa cacacacggc tcgggtttat ctttggtctg    6060
ttcgccgact ggtgggctgg ggtggatgat ggtcgctgca ctgagccgtt tgtctcgttc    6120
gaccgctggg atgcgatcct aaagcgtgtc gggttttccg gtgtggacag tcgcaccacg    6180
gatcgggacg caaatctatt cccgacctct gtgtttagta cccatgcaat tgacgccacc    6240
gtggagtact tagacgcgcc gcttccagcc agcggcaccg tcaaggactc ttaccctccc    6300
ttggtggtgg taggagggca gaccccccaa tctcagcgtc tcctgaacga tataaaagcg    6360
atcatgcctc ctcgtccgct ccagacatac aagcgcctcg tggatttgct agacgcggag    6420
gagctgccga tgaagtccac gtttgtcatg ctcacggagc tggacgagga attattcgcc    6480
gggctcactg aagagacctt cgaggcaacc aagctgctgc tcacgtacgc cagcaatacg    6540
gtctggctga cagaaaatgc ctgggtccaa catcctcacc aggcgagcac gatcggcatg    6600
ctacgctcca tccgccggga gcatcctgac ttggagttc atgttctgga cgtcgacgcg      6660
gttgaaacct tcgatgcaac cttcctggtt gaacaggtgc ttcggcttga ggagcatacg    6720
gatgagctgg ccagttcaac tacatggact caagaacccg aggtctcctg gtgtaaaggc    6780
cgcccgtgga ttcctcgtct gaagcgcgat ctggctcgca ataaccgaat gaactcctcg    6840
cgccgtccca tatacgagat gatcgattcg tcgcgggctc ccgtggcatt acagacggct    6900
cgggattcat catcctactt cttggagtcc gctgaaacct ggtttgtgcc tgagagtgtt    6960
cagcagatgc aaacaaagac gatctatgtc cactttagct gtccccatgc gcttagggtc    7020
ggacagctcg ggttttttcta tcttgtgcag ggtcacgtcc aggagggcaa tcgcgaagtg    7080
cccgtcgtgg cctagcaga gcgtaacgca tccattgtgc acgttcgtcc cgattatata    7140
tatactgagg cagataacaa tctgtctgag ggtggtggca gccttatggt aaccgtcctc    7200
gccgcggcgc tgttggcgga gacggtgatc agtaccgcca agtgcctggg ggtaactgac    7260
tcaatcctcg ttctgaatcc ccccagcata tgtgggcaga tgttgctcca tgctggtgaa    7320
gagatcggtc ttcaagttca tctggccacc acttctggca acaggagttc ggtttctgct    7380
ggagacgcca agtcctggct aacattgcat gctcgcgaca cggactggca cctgcgacgg    7440
gtactgcccc ggggtgtcca ggctttagtc gacttatcag ccgaccagag ctgtgaaggt    7500
```

```
ttgactcaga ggatgatgaa agttctgatg cctggctgtg cccattaccg tgcggcagac    7560
ctgttcacag acaccgtttc cactgaattg catagcggat cgcggcatca agcttcactg    7620
cccgccgcat attgggagca tgtggtatcc ttagcccgcc agggacttcc tagtgtcagc    7680 gagggtggg aggtgatgcc gtgcactcaa tttgcagcgc atgccgacaa gacgcgcccg    7740
gatctctcga cagttatttc ctggccccgg gagtcggacg aggctacgct tcctaccagg    7800
gttcgctcca ttgacgctga gaccctcttt gcggccgaca aaacatatct cctggtcgga    7860
ctgactggag atcttggacg atcactaggt cgttggatgg tccagcatgg ggcctgccac    7920
attgtactta cgagcagaaa tccgcaggtg aaccccaagt ggctggcgca tgttgaagaa    7980
ctgggtggtc gagtcactgt tctttccatg taagaggagt ccttccttct gcaattcctc    8040
cttatgatcc cgactaacgc agctggcttc agggacgtga caagccaaaa ctcagtggaa    8100
gctggcctgg ctaaactcaa ggatctgcat ctgccaccag tgggggtat tgcctttggc     8160 cctctggttc tgcaggatgt gatgctaaat aatatggaac tgccaatgat ggagatggtg    8220
ctcaacccca aggtcgaagg cgtccgcatc ctgcacgaga agttctccga tccgaccagt    8280
agcaaccctc tcgacttctt cgtgatgttc tcctcgattg tggccgtcat gggcaacccg    8340
ggtcaggcta actacagtgc ggctaactgc taccttcaag cgctggcgca gcagcgagtt    8400
gcatccggat tagcagtacg ttttcactcc atccttttgct aaacactcct atgggccttt    8460
actaaaccgg gcaggcgtcc accatcgaca tcggtgccgt gtacgcgtt gggttcgtca     8520 ctcgggcgga gctggaggag gactttaatg caattcggtt catgttcgat tcggttgagg    8580
aacatgaact gcatacactg tttgctgagg cagtggtggc cggtcgacga gccgtgcacc    8640
agcaagagca gcagcggaag ttcgcgacag tgctcgacat ggctgatctg gaactgacaa    8700
ccggaattcc gcccctggat ccagccctca aagatcggat caccttcttc gacgaccccc    8760
gcataggcaa cttaaaaatt ccggagtacc gaggggccaa agcaggcgaa ggggcagccg    8820
gctccaaggg ctcggtcaaa gaacagctct tgcaggcgac gaacctggac caggtccgtc    8880
agatcgtcat cggtaagttg agcgaatccg gggaatattc tcccccttcct cactcagcgg   8940 actggagatt aaccgcttct tttcctttgg cagatggact ctccgcgaag ctgcaggtga    9000
ccctgcagat ccccgatggg gaaagcgtgc atcccaccat cccactaatc gatcaggggg    9060
tggactctct gggcgcggtc accgtgggaa cctggttctc caagcagctg taccttgatt    9120
tgccactcct gaaagtgctt gggggtgctt cgatcaccga tctcgctaat gaggctgctg    9180
cgcgattgcc acctagctcc attccctcg tcgcagccac cgacgggggt gcagagagca    9240
ctgacaatac ttccgagaat gaagtttcgg gacgcgagga tactgacctt agtgccgccg    9300
ccaccatcac tgagccctcg tctgccgacg aagacgatac ggagccgggc gacgaggacg    9360
tcccgcgttc ccaccatcca ctgtctctcg gcaagaata ctcctggaga atccagcagg     9420
gagccgaaga ccccaccgtc tttaacaaca ccattggtat gttcatgaag ggctctattg    9480
accttaaacg gctgtacaag gcgttgagag cggtcttgcg ccgccacgag atcttccgca    9540
cggggtttgc caacgtggat gagaacggga tggcccagct ggtgtttggt caaaccaaaa    9600
acaaagtcca gaccatccaa gtgtctgacc gagccggcgc cgaagagggc taccgacaac    9660
tggtgcagac acggtataac cctgccgcag gagacacctt gcggctggtg gacttcttct    9720
ggggccagga cgaccatctg ctggttgtgg cttaccaccg actcgtcggg gatggatcta    9780
ctacagagaa catcttcgtc gaagcgggcc agctctacga cggcacgtcg ctaagtccac    9840
```

-continued

```
atgtccctca gtttgcggac ctggcggcac ggcaacgcgc aatgctcgag gatgggagaa    9900
tggaggagga tctcgcgtac tggaagaaaa tgcattaccg accgtcctca attccagtgc    9960
tcccactgat gcggcccctg gtaggtaaca gtagcaggtc cgatactcca aatttccagc   10020
actgtggacc ctggcagcag cacgaagccg tggcgcgact tgatccgatg gtggccttcc   10080
gcatcaagga gcgcagtcgc aagcacaagg cgacgccgat gcagttctat ctggcggcgt   10140
atcaggtgct gttggcgcgc ctcaccgaca gcaccgatct caccgtgggc ctcgccgaca   10200
ccaaccgtgc gactgtcgac gagatggcgg ccatggggtt cttcgccaac ctccttcccc   10260
tgcgcttccg ggatttccgc ccccatataa cgtttggcga gcaccttatc gccacccgtg   10320
acctggtgcg tgaggccttg cagcacgccc gcgtgcccta cggcgtcctc ctcgatcaac   10380
tggggctgga ggtcccggtc ccgaccagca atcaacctgc gcctttgttc caggccgtct   10440
tcgattacaa gcagggccag gcggaaagtg gaacgattgg gggtgccaag ataaccgagg   10500
tgattgccac gcgcgagcgc accccttacg atgtcgtgct ggagatgtcg gatgatccca   10560
ccaaggatcc gctgctcacg gccaagttac agagttcccg ctacgaggct caccaccctc   10620
aagccttctt ggagagctac atgtcccttc tctctatgtt ctcgatgaat cccgccctga   10680
agctggcatg atgcgcaaa catagaacat gatagcgcag cagggacgat gtagatagag   10740
ctttgcttct gcgggtggat ctataatata gtatatataa atatggtgag ccgaacgaag   10800
agggggaat gccacaatta tttactgttt tgcgccgtac acgaggagaa gacgtccaga   10860
acaacataaa tatatcactc tagtgagaca ccatatattc ggagagacta taaaaatata   10920
catctactcc aatgtctggg ccgtcacaca cagcttacga aaacgattaa tgacctccaa   10980
cacgtcgcgc ggtcgattgg gaaactgatg ctgcccagca aactccaata cctgcgcctc   11040
tcgggggggag aaatggcgcg ccaccagcat cttcgatcct gcgagcgcaa aatcatcgcg   11100
accctgcaga tgtaatgtcg gtatccgaat gaccagttcc tcctgccact cggtatcttt   11160
gctgtcgttg tcgtcgtcat ggttcttcat cattcgttcc tcatatactg gcttgcctcg   11220
tcttgatacc aggacagat caacagcgca acactcatcc ggggcaacca gggcaggtga   11280
cccatctgct gctgccagag gagcaaggtc gtcaccaggg caccttcgga gaaaccgata   11340
gcacccacga tagggatgtg ggggtgttga gtctgccagt cgacaatggt gcggcggatg   11400
gggtcgtgga cggcggcgag gcgttcgctc acggagggtc cattatgatt gttgtcgctg   11460
ctgctttcaa accaggagta atatggccct aggtcggcga agacggggag aatcccaggc   11520
cctgcagagg aagggaacgg agctgtcacg tagacgaatt c                       11561
```

<210> SEQ ID NO 2
<211> LENGTH: 3038
<212> TYPE: PRT
<213> ORGANISM: TPKS Protein

<400> SEQUENCE: 2

```
Met Ala Gln Ser Met Tyr Pro Asn Glu Pro Ile Val Val Gly Ser
 1               5                   10                  15

Gly Cys Arg Phe Pro Gly Asp Ala Asn Thr Pro Ser Lys Leu Trp Glu
            20                  25                  30

Leu Leu Gln His Pro Arg Asp Val Gln Ser Arg Ile Pro Lys Glu Arg
        35                  40                  45

Phe Asp Val Asp Thr Phe Tyr His Pro Asp Gly Lys His His Gly Arg
    50                  55                  60

Thr Asn Ala Pro Tyr Ala Tyr Val Leu Gln Asp Asp Leu Gly Ala Phe
```

```
65                   70                  75                  80
Asp Ala Ala Phe Phe Asn Ile Gln Ala Gly Glu Ala Glu Ser Met Asp
                85                  90                  95

Pro Gln His Arg Leu Leu Leu Glu Thr Val Tyr Glu Ala Val Thr Asn
            100                 105                 110

Ala Gly Met Arg Ile Gln Asp Leu Gln Gly Thr Ser Thr Ala Val Tyr
            115                 120                 125

Val Gly Val Met Thr His Asp Tyr Glu Thr Val Ser Thr Arg Asp Leu
        130                 135                 140

Glu Ser Ile Pro Thr Tyr Ser Ala Thr Gly Val Ala Val Ser Val Ala
145                 150                 155                 160

Ser Asn Arg Ile Ser Tyr Phe Phe Asp Trp His Gly Pro Ser Met Thr
                165                 170                 175

Ile Asp Thr Ala Cys Ser Ser Leu Val Ala Val His Leu Ala Val
            180                 185                 190

Gln Gln Leu Arg Thr Gly Gln Ser Ser Met Ala Ile Ala Ala Gly Ala
            195                 200                 205

Asn Leu Ile Leu Gly Pro Met Thr Phe Val Leu Glu Ser Lys Leu Ser
    210                 215                 220

Met Leu Ser Pro Ser Gly Arg Ser Arg Met Trp Asp Ala Gly Ala Asp
225                 230                 235                 240

Gly Tyr Ala Arg Gly Glu Ala Val Cys Ser Val Val Leu Lys Thr Leu
                245                 250                 255

Ser Gln Ala Leu Arg Asp Gly Asp Thr Ile Glu Cys Val Ile Arg Glu
            260                 265                 270

Thr Gly Val Asn Gln Asp Gly Arg Thr Thr Gly Ile Thr Met Pro Asn
            275                 280                 285

His Ser Ala Gln Glu Ala Leu Ile Lys Ala Thr Tyr Ala Gln Ala Gly
    290                 295                 300

Leu Asp Ile Thr Lys Ala Glu Asp Arg Cys Gln Phe Phe Glu Ala His
305                 310                 315                 320

Gly Thr Gly Thr Pro Ala Gly Asp Pro Gln Glu Ala Glu Ala Ile Ala
                325                 330                 335

Thr Ala Phe Phe Gly His Glu Gln Val Ala Arg Ser Asp Gly Asn Glu
            340                 345                 350

Arg Ala Pro Leu Phe Val Gly Ser Ala Lys Thr Val Val Gly His Thr
            355                 360                 365

Glu Gly Thr Ala Gly Leu Ala Gly Leu Met Lys Ala Ser Phe Ala Val
370                 375                 380

Arg His Gly Val Ile Pro Pro Asn Leu Leu Phe Asp Lys Ile Ser Pro
385                 390                 395                 400

Arg Val Ala Pro Phe Tyr Lys Asn Leu Arg Ile Pro Thr Glu Ala Thr
                405                 410                 415

Gln Trp Pro Ala Leu Pro Pro Gly Gln Pro Arg Arg Ala Ser Val Asn
            420                 425                 430

Ser Phe Gly Phe Gly Gly Thr Asn Ala His Ala Ile Ile Glu Glu Tyr
    435                 440                 445

Met Glu Pro Glu Gln Asn Gln Leu Arg Val Ser Asn Asn Glu Asp Cys
    450                 455                 460

Pro Pro Met Thr Gly Val Leu Ser Leu Pro Leu Val Leu Ser Ala Lys
465                 470                 475                 480

Ser Gln Arg Ser Leu Lys Ile Met Met Glu Met Leu Gln Phe Leu
            485                 490                 495
```

-continued

```
Gln Ser His Pro Glu Ile His Leu His Asp Leu Thr Trp Ser Leu Leu
            500                 505                 510

Arg Lys Arg Ser Val Leu Pro Phe Arg Ala Ile Val Gly His Ser
        515                 520                 525

His Glu Thr Ile Arg Arg Ala Leu Glu Asp Ala Ile Glu Asp Gly Ile
    530                 535                 540

Val Ser Ser Asp Phe Thr Thr Glu Val Arg Gly Gln Pro Ser Val Leu
545                 550                 555                 560

Gly Ile Phe Thr Gly Gln Gly Ala Gln Trp Pro Gly Met Leu Lys Asn
                565                 570                 575

Leu Ile Glu Ala Ser Pro Tyr Val Arg Asn Ile Val Arg Glu Leu Asp
            580                 585                 590

Asp Ser Leu Gln Ser Leu Pro Glu Lys Tyr Arg Pro Ser Trp Thr Leu
        595                 600                 605

Leu Asp Gln Phe Met Leu Glu Gly Glu Ala Ser Asn Val Gln Tyr Ala
    610                 615                 620

Thr Phe Ser Gln Pro Leu Cys Cys Ala Val Gln Ile Val Leu Val Arg
625                 630                 635                 640

Leu Leu Glu Ala Ala Arg Ile Arg Phe Thr Ala Val Val Gly His Ser
                645                 650                 655

Ser Gly Glu Ile Ala Cys Ala Phe Ala Ala Gly Leu Ile Ser Ala Ser
            660                 665                 670

Leu Ala Ile Arg Ile Ala Tyr Leu Arg Gly Val Val Ser Ala Gly Gly
        675                 680                 685

Ala Arg Gly Thr Pro Gly Ala Met Leu Ala Ala Gly Met Ser Phe Glu
    690                 695                 700

Glu Ala Gln Glu Ile Cys Glu Leu Asp Ala Phe Glu Gly Arg Ile Cys
705                 710                 715                 720

Val Ala Ala Ser Asn Ser Pro Asp Ser Val Thr Phe Ser Gly Asp Ala
                725                 730                 735

Asn Ala Ile Asp His Leu Lys Gly Met Leu Glu Asp Glu Ser Thr Phe
            740                 745                 750

Ala Arg Leu Leu Lys Val Asp Thr Ala Tyr His Ser His His Met Leu
        755                 760                 765

Pro Cys Ala Asp Pro Tyr Met Gln Ala Leu Glu Glu Cys Gly Cys Ala
    770                 775                 780

Val Ala Asp Ala Gly Ser Pro Ala Gly Ser Val Pro Trp Tyr Ser Ser
785                 790                 795                 800

Val Asp Ala Glu Asn Arg Gln Met Ala Ala Arg Asp Val Thr Ala Lys
                805                 810                 815

Tyr Trp Lys Asp Asn Leu Val Ser Pro Val Leu Phe Ser His Ala Val
            820                 825                 830

Gln Arg Ala Val Val Thr His Lys Ala Leu Asp Ile Gly Ile Glu Val
        835                 840                 845

Gly Cys His Pro Ala Leu Lys Ser Pro Cys Val Ala Thr Ile Lys Asp
    850                 855                 860

Val Leu Ser Gly Val Asp Leu Ala Tyr Thr Gly Cys Leu Glu Arg Gly
865                 870                 875                 880

Lys Asn Asp Leu Asp Ser Phe Ser Arg Ala Leu Ala Tyr Leu Trp Glu
                885                 890                 895

Arg Phe Gly Ala Ser Ser Phe Ala Asp Glu Phe Met Arg Ala Val
            900                 905                 910
```

```
Ala Pro Asp Arg Pro Cys Met Ser Val Ser Lys Leu Leu Pro Ala Tyr
        915                 920                 925

Pro Trp Asp Arg Ser Arg Arg Tyr Trp Val Glu Ser Arg Ala Thr Arg
        930                 935                 940

His His Leu Arg Gly Pro Lys Pro His Leu Leu Gly Lys Leu Ser
945                 950                 955                 960

Glu Tyr Ser Thr Pro Leu Ser Phe Gln Trp Leu Asn Phe Val Arg Pro
                965                 970                 975

Arg Asp Ile Glu Trp Leu Asp Gly His Ala Leu Gln Gly Gln Thr Val
            980                 985                 990

Phe Pro Ala Ala Gly Tyr Ile Val Met Ala Met Glu Ala Ala Leu Met
            995                 1000                1005

Ile Ala Gly Thr His Ala Lys Gln Val Lys Leu Leu Glu Ile Leu Asp
        1010                1015                1020

Met Ser Ile Asp Lys Ala Val Ile Phe Asp Asp Glu Asp Ser Leu Val
1025                1030                1035                104

Glu Leu Asn Leu Thr Ala Asp Val Ser Arg Asn Ala Gly Glu Ala Gly
            1045                1050                1055

Ser Met Thr Ile Ser Phe Lys Ile Asp Ser Cys Leu Ser Lys Glu Gly
            1060                1065                1070

Asn Leu Ser Leu Ser Ala Lys Gly Gln Leu Ala Leu Thr Ile Glu Asp
        1075                1080                1085

Val Asn Pro Arg Thr Thr Ser Ala Ser Asp Gln His His Leu Pro Pro
        1090                1095                1100

Pro Glu Glu Glu His Pro His Met Asn Arg Val Asn Ile Asn Ala Phe
1105                1110                1115                112

Tyr His Glu Leu Gly Leu Met Gly Tyr Asn Tyr Ser Lys Asp Phe Arg
            1125                1130                1135

Arg Leu His Asn Met Gln Arg Ala Asp Leu Arg Ala Ser Gly Thr Leu
        1140                1145                1150

Asp Phe Ile Pro Leu Met Asp Glu Gly Asn Gly Cys Pro Leu Leu Leu
            1155                1160                1165

His Pro Ala Ser Leu Asp Val Ala Phe Gln Thr Val Ile Gly Ala Tyr
        1170                1175                1180

Ser Ser Pro Gly Asp Arg Arg Leu Arg Cys Leu Tyr Val Pro Thr His
1185                1190                1195                120

Val Asp Arg Ile Thr Leu Val Pro Ser Leu Cys Leu Ala Thr Ala Glu
            1205                1210                1215

Ser Gly Cys Glu Lys Val Ala Phe Asn Thr Ile Asn Thr Tyr Asp Lys
        1220                1225                1230

Gly Asp Tyr Leu Ser Gly Asp Ile Val Val Phe Asp Ala Glu Gln Thr
        1235                1240                1245

Thr Leu Phe Gln Val Glu Asn Ile Thr Phe Lys Pro Phe Ser Pro Pro
        1250                1255                1260

Asp Ala Ser Thr Asp His Ala Met Phe Ala Arg Trp Ser Trp Gly Pro
1265                1270                1275                128

Leu Thr Pro Asp Ser Leu Leu Asp Asn Pro Glu Tyr Trp Ala Thr Ala
            1285                1290                1295

Gln Asp Lys Glu Ala Ile Pro Ile Ile Glu Arg Ile Val Tyr Phe Tyr
        1300                1305                1310

Ile Arg Ser Phe Leu Ser Gln Leu Thr Leu Glu Glu Arg Gln Gln Ala
        1315                1320                1325

Ala Phe His Leu Gln Lys Gln Ile Glu Trp Leu Glu Gln Val Leu Ala
```

-continued

```
        1330              1335              1340

Ser Ala Lys Glu Gly Arg His Leu Trp Tyr Asp Pro Gly Trp Glu Asn
1345                1350                1355                 136

Asp Thr Glu Ala Gln Ile Glu His Leu Cys Thr Ala Asn Ser Tyr His
                1365                1370                1375

Pro His Val Arg Leu Val Gln Arg Val Gly Gln His Leu Leu Pro Thr
            1380                1385                1390

Val Arg Ser Asn Gly Asn Pro Phe Asp Leu Leu Asp His Asp Gly Leu
        1395                1400                1405

Leu Thr Glu Phe Tyr Thr Asn Thr Leu Ser Phe Gly Pro Ala Leu His
    1410                1415                1420

Tyr Ala Arg Glu Leu Val Ala Gln Ile Ala His Arg Tyr Gln Ser Met
1425                1430                1435                 144

Asp Ile Leu Glu Ile Gly Ala Gly Thr Gly Gly Ala Thr Lys Tyr Val
                1445                1450                1455

Leu Ala Thr Pro Gln Leu Gly Phe Asn Ser Tyr Thr Tyr Thr Asp Ile
            1460                1465                1470

Ser Thr Gly Phe Phe Glu Gln Ala Arg Glu Gln Phe Ala Pro Phe Glu
        1475                1480                1485

Asp Arg Met Val Phe Glu Pro Leu Asp Ile Arg Arg Ser Pro Ala Glu
    1490                1495                1500

Gln Gly Phe Glu Pro His Ala Tyr Asp Leu Ile Ile Ala Ser Asn Val
1505                1510                1515                 152

Leu His Ala Thr Pro Asp Leu Glu Lys Thr Met Ala His Ala Arg Ser
                1525                1530                1535

Leu Leu Lys Pro Gly Gly Gln Met Val Ile Leu Glu Ile Thr His Lys
            1540                1545                1550

Glu His Thr Arg Leu Gly Phe Ile Phe Gly Leu Phe Ala Asp Trp Trp
        1555                1560                1565

Ala Gly Val Asp Asp Gly Arg Cys Thr Glu Pro Phe Val Ser Phe Asp
    1570                1575                1580

Arg Trp Asp Ala Ile Leu Lys Arg Val Gly Phe Ser Gly Val Asp Ser
1585                1590                1595                 160

Arg Thr Thr Asp Arg Asp Ala Asn Leu Phe Pro Thr Ser Val Phe Ser
                1605                1610                1615

Thr His Ala Ile Asp Ala Thr Val Glu Tyr Leu Asp Ala Pro Leu Ala
            1620                1625                1630

Ser Ser Gly Thr Val Lys Asp Ser Tyr Pro Pro Leu Val Val Gly
        1635                1640                1645

Gly Gln Thr Pro Gln Ser Gln Arg Leu Leu Asn Asp Ile Lys Ala Ile
    1650                1655                1660

Met Pro Pro Arg Pro Leu Gln Thr Tyr Lys Arg Leu Val Asp Leu Leu
1665                1670                1675                 168

Asp Ala Glu Glu Leu Pro Met Lys Ser Thr Phe Val Met Leu Thr Glu
                1685                1690                1695

Leu Asp Glu Glu Leu Phe Ala Gly Leu Thr Glu Thr Phe Glu Ala
            1700                1705                1710

Thr Lys Leu Leu Leu Thr Tyr Ala Ser Asn Thr Val Trp Leu Thr Glu
        1715                1720                1725

Asn Ala Trp Val Gln His Pro His Gln Ala Ser Thr Ile Gly Met Leu
    1730                1735                1740

Arg Ser Ile Arg Arg Glu His Pro Asp Leu Gly Val His Val Leu Asp
1745                1750                1755                 176
```

-continued

```
Val Asp Ala Val Glu Thr Phe Asp Ala Thr Phe Leu Val Glu Gln Val
            1765                1770                1775
Leu Arg Leu Glu Glu His Thr Asp Glu Leu Ala Ser Ser Thr Thr Trp
            1780                1785                1790
Thr Gln Glu Pro Glu Val Ser Trp Cys Lys Gly Arg Pro Trp Ile Pro
            1795                1800                1805
Arg Leu Lys Arg Asp Leu Ala Arg Asn Asn Arg Met Asn Ser Ser Arg
            1810                1815                1820
Arg Pro Ile Tyr Glu Met Ile Asp Ser Ser Arg Ala Pro Val Ala Leu
1825                1830                1835                184
Gln Thr Ala Arg Asp Ser Ser Ser Tyr Phe Leu Glu Ser Ala Glu Thr
            1845                1850                1855
Trp Phe Val Pro Glu Ser Val Gln Gln Met Glu Thr Lys Thr Ile Tyr
            1860                1865                1870
Val His Phe Ser Cys Pro His Ala Leu Arg Val Gly Gln Leu Gly Phe
            1875                1880                1885
Phe Tyr Leu Val Gln Gly His Val Gln Glu Gly Asn Arg Glu Val Pro
            1890                1895                1900
Val Val Ala Leu Ala Glu Arg Asn Ala Ser Ile Val His Val Arg Pro
1905                1910                1915                192
Asp Tyr Ile Tyr Thr Glu Ala Asp Asn Asn Leu Ser Glu Gly Gly Gly
            1925                1930                1935
Ser Leu Met Val Thr Val Leu Ala Ala Val Leu Ala Glu Thr Val
            1940                1945                1950
Ile Ser Thr Ala Lys Cys Leu Gly Val Thr Asp Ser Ile Leu Val Leu
            1955                1960                1965
Asn Pro Pro Ser Ile Cys Gly Gln Met Leu Leu His Ala Gly Glu Glu
            1970                1975                1980
Ile Gly Leu Gln Val His Leu Ala Thr Thr Gly Asn Arg Ser Ser
1985                1990                1995                200
Val Ser Ala Gly Asp Ala Lys Ser Trp Leu Thr Leu His Ala Arg Asp
            2005                2010                2015
Thr Asp Trp His Leu Arg Arg Val Leu Pro Arg Gly Val Gln Ala Leu
            2020                2025                2030
Val Asp Leu Ser Ala Asp Gln Ser Cys Glu Gly Leu Thr Gln Arg Met
            2035                2040                2045
Met Lys Val Leu Met Pro Gly Cys Ala His Tyr Arg Ala Ala Asp Leu
            2050                2055                2060
Phe Thr Asp Thr Val Ser Thr Glu Leu His Ser Gly Ser Arg His Gln
2065                2070                2075                208
Ala Ser Leu Pro Ala Ala Tyr Trp Glu His Val Val Ser Leu Ala Arg
            2085                2090                2095
Gln Gly Leu Pro Ser Val Ser Glu Gly Trp Glu Val Met Pro Cys Thr
            2100                2105                2110
Gln Phe Ala Ala His Ala Asp Lys Thr Arg Pro Asp Leu Ser Thr Val
            2115                2120                2125
Ile Ser Trp Pro Arg Glu Ser Asp Glu Ala Thr Leu Pro Thr Arg Val
            2130                2135                2140
Arg Ser Ile Asp Ala Glu Thr Leu Phe Ala Ala Asp Lys Thr Tyr Leu
2145                2150                2155                216
Leu Val Gly Leu Thr Gly Asp Leu Gly Arg Ser Leu Gly Arg Trp Met
            2165                2170                2175
```

```
Val Gln His Gly Ala Cys His Ile Val Leu Thr Ser Arg Asn Pro Gln
            2180                2185                2190

Val Asn Pro Lys Trp Leu Ala His Val Glu Glu Leu Gly Gly Arg Val
        2195                2200                2205

Thr Val Leu Ser Met Asp Val Thr Ser Gln Asn Ser Val Glu Ala Gly
        2210                2215                2220

Leu Ala Lys Leu Lys Asp Leu His Leu Pro Pro Val Gly Gly Ile Ala
2225                2230                2235                224

Phe Gly Pro Leu Val Leu Gln Asp Val Met Leu Asn Asn Met Glu Leu
            2245                2250                2255

Pro Met Met Glu Met Val Leu Asn Pro Lys Val Glu Gly Val Arg Ile
            2260                2265                2270

Leu His Glu Lys Phe Ser Asp Pro Thr Ser Ser Asn Pro Leu Asp Phe
            2275                2280                2285

Phe Val Met Phe Ser Ser Ile Val Ala Val Met Gly Asn Pro Gly Gln
            2290                2295                2300

Ala Asn Tyr Ser Ala Ala Asn Cys Tyr Leu Gln Ala Leu Ala Gln Gln
2305                2310                2315                232

Arg Val Ala Ser Gly Leu Ala Ala Ser Thr Ile Asp Ile Gly Ala Val
            2325                2330                2335

Tyr Gly Val Gly Phe Val Thr Arg Ala Glu Leu Glu Glu Asp Phe Asn
            2340                2345                2350

Ala Ile Arg Phe Met Phe Asp Ser Val Glu Glu His Glu Leu His Thr
            2355                2360                2365

Leu Phe Ala Glu Ala Val Val Ala Gly Arg Arg Ala Val His Gln Gln
            2370                2375                2380

Glu Gln Gln Arg Lys Phe Ala Thr Val Leu Asp Met Ala Asp Leu Glu
2385                2390                2395                240

Leu Thr Thr Gly Ile Pro Pro Leu Asp Pro Ala Leu Lys Asp Arg Ile
            2405                2410                2415

Thr Phe Phe Asp Asp Pro Arg Ile Gly Asn Leu Lys Ile Pro Glu Tyr
            2420                2425                2430

Arg Gly Ala Lys Ala Gly Glu Gly Ala Ala Gly Ser Lys Gly Ser Val
            2435                2440                2445

Lys Glu Gln Leu Leu Gln Ala Thr Asn Leu Asp Gln Val Arg Gln Ile
            2450                2455                2460

Val Ile Asp Gly Leu Ser Ala Lys Leu Gln Val Thr Leu Gln Ile Pro
2465                2470                2475                248

Asp Gly Glu Ser Val His Pro Thr Ile Pro Leu Ile Asp Gln Gly Val
            2485                2490                2495

Asp Ser Leu Gly Ala Val Thr Val Gly Thr Trp Phe Ser Lys Gln Leu
            2500                2505                2510

Tyr Leu Asp Leu Pro Leu Leu Lys Val Leu Gly Gly Ala Ser Ile Thr
            2515                2520                2525

Asp Leu Ala Asn Glu Ala Ala Ala Arg Leu Pro Pro Ser Ser Ile Pro
            2530                2535                2540

Leu Val Ala Ala Thr Asp Gly Gly Ala Glu Ser Thr Asp Asn Thr Ser
2545                2550                2555                256

Glu Asn Glu Val Ser Gly Arg Glu Asp Thr Asp Leu Ser Ala Ala Ala
            2565                2570                2575

Thr Ile Thr Glu Pro Ser Ser Ala Asp Glu Asp Thr Glu Pro Gly
            2580                2585                2590

Asp Glu Asp Val Pro Arg Ser His Pro Leu Ser Leu Gly Gln Glu
```

-continued

```
            2595                2600                2605
Tyr Ser Trp Arg Ile Gln Gln Gly Ala Glu Asp Pro Thr Val Phe Asn
    2610                2615                2620
Asn Thr Ile Gly Met Phe Met Lys Gly Ser Ile Asp Leu Lys Arg Leu
2625                2630                2635                 264
Tyr Lys Ala Leu Arg Ala Val Leu Arg Arg His Glu Ile Phe Arg Thr
            2645                2650                2655
Gly Phe Ala Asn Val Asp Glu Asn Gly Met Ala Gln Leu Val Phe Gly
            2660                2665                2670
Gln Thr Lys Asn Lys Val Gln Thr Ile Gln Val Ser Asp Arg Ala Gly
            2675                2680                2685
Ala Glu Glu Gly Tyr Arg Gln Leu Val Gln Thr Arg Tyr Asn Pro Ala
            2690                2695                2700
Ala Gly Asp Thr Leu Arg Leu Val Asp Phe Phe Trp Gly Gln Asp Asp
2705                2710                2715                 272
His Leu Leu Val Val Ala Tyr His Arg Leu Val Gly Asp Gly Ser Thr
            2725                2730                2735
Thr Glu Asn Ile Phe Val Glu Ala Gly Gln Leu Tyr Asp Gly Thr Ser
            2740                2745                2750
Leu Ser Pro His Val Pro Gln Phe Ala Asp Leu Ala Ala Arg Gln Arg
            2755                2760                2765
Ala Met Leu Glu Asp Gly Arg Met Glu Glu Asp Leu Ala Tyr Trp Lys
            2770                2775                2780
Lys Met His Tyr Arg Pro Ser Ser Ile Pro Val Leu Pro Leu Met Arg
2785                2790                2795                 280
Pro Leu Val Gly Asn Ser Ser Arg Ser Asp Thr Pro Asn Phe Gln His
            2805                2810                2815
Cys Gly Pro Trp Gln Gln His Glu Ala Val Ala Arg Leu Asp Pro Met
            2820                2825                2830
Val Ala Phe Arg Ile Lys Glu Arg Ser Arg Lys His Lys Ala Thr Pro
            2835                2840                2845
Met Gln Phe Tyr Leu Ala Ala Tyr Gln Val Leu Leu Ala Arg Leu Thr
            2850                2855                2860
Asp Ser Thr Asp Leu Thr Val Gly Leu Ala Asp Thr Asn Arg Ala Thr
2865                2870                2875                 288
Val Asp Glu Met Ala Ala Met Gly Phe Phe Ala Asn Leu Leu Pro Leu
            2885                2890                2895
Arg Phe Arg Asp Phe Arg Pro His Ile Thr Phe Gly Glu His Leu Ile
            2900                2905                2910
Ala Thr Arg Asp Leu Val Arg Glu Ala Leu Gln His Ala Arg Val Pro
            2915                2920                2925
Tyr Gly Val Leu Leu Asp Gln Leu Gly Leu Glu Val Pro Val Pro Thr
            2930                2935                2940
Ser Asn Gln Pro Ala Pro Leu Phe Gln Ala Val Phe Asp Tyr Lys Gln
2945                2950                2955                 296
Gly Gln Ala Glu Ser Gly Thr Ile Gly Gly Ala Lys Ile Thr Glu Val
            2965                2970                2975
Ile Ala Thr Arg Glu Arg Thr Pro Tyr Asp Val Val Leu Glu Met Ser
            2980                2985                2990
Asp Asp Pro Thr Lys Asp Pro Leu Leu Thr Ala Lys Leu Gln Ser Ser
            2995                3000                3005
Arg Tyr Glu Ala His His Pro Gln Ala Phe Leu Glu Ser Tyr Met Ser
            3010                3015                3020
```

Leu Leu Ser Met Phe Ser Met Asn Pro Ala Leu Lys Leu Ala
3025              3030              3035

<210> SEQ ID NO 3
<211> LENGTH: 45
<212> TYPE: DNA
<213> ORGANISM: Probe

<400> SEQUENCE: 3
gatacggcat gcagctcgtc gttggttgcc gttcatctgg ctgca                45

<210> SEQ ID NO 4
<211> LENGTH: 5
<212> TYPE: PRT
<213> ORGANISM: Artificial Sequence
<220> FEATURE:
<223> OTHER INFORMATION: Variant
<221> NAME/KEY: VARIANT
<222> LOCATION: (1)...(5)
<223> OTHER INFORMATION: Xaa = Any Amino Acid
<221> NAME/KEY: VARIANT
<222> LOCATION: (1)...(5)
<223> OTHER INFORMATION: Xaa = Any Amino Acid
<221> NAME/KEY: VARIANT
<222> LOCATION: (1)...(5)
<223> OTHER INFORMATION: Xaa = Any Amino Acid

<400> SEQUENCE: 4

Gly Xaa Ser Xaa Gly
 1               5

<210> SEQ ID NO 5
<211> LENGTH: 10
<212> TYPE: PRT
<213> ORGANISM: Artificial Sequence
<220> FEATURE:
<223> OTHER INFORMATION: Variant
<221> NAME/KEY: VARIANT
<222> LOCATION: (1)...(10)
<223> OTHER INFORMATION: Xaa = Any Amino Acid
<221> NAME/KEY: VARIANT
<222> LOCATION: (1)...(10)
<223> OTHER INFORMATION: Xaa = Any Amino Acid
<221> NAME/KEY: VARIANT
<222> LOCATION: (1)...(10)
<223> OTHER INFORMATION: Xaa = Any Amino Acid

<400> SEQUENCE: 5

His Xaa Xaa Xaa Gly Xaa Xaa Xaa Xaa Pro
 1               5                  10

<210> SEQ ID NO 6
<211> LENGTH: 5
<212> TYPE: PRT
<213> ORGANISM: Artificial Sequence
<220> FEATURE:
<223> OTHER INFORMATION: Variant
<221> NAME/KEY: VARIANT
<222> LOCATION: (1)...(5)
<223> OTHER INFORMATION: Xaa = Any Amino Acid
<221> NAME/KEY: VARIANT
<222> LOCATION: (1)...(5)
<223> OTHER INFORMATION: Xaa = Any Amino Acid
<221> NAME/KEY: VARIANT
<222> LOCATION: (1)...(5)
<223> OTHER INFORMATION: Xaa = Any Amino Acid

<400> SEQUENCE: 6

Gly Xaa Gly Xaa Gly
 1               5

<210> SEQ ID NO 7
<211> LENGTH: 6
<212> TYPE: PRT
<213> ORGANISM: Artificial Sequence
<220> FEATURE:
<223> OTHER INFORMATION: Variant
<221> NAME/KEY: VARIANT
<222> LOCATION: (1)...(6)
<223> OTHER INFORMATION: Xaa = Any Amino Acid
<221> NAME/KEY: VARIANT
<222> LOCATION: (1)...(6)
<223> OTHER INFORMATION: Xaa = Any Amino Acid
<221> NAME/KEY: VARIANT
<222> LOCATION: (1)...(6)
<223> OTHER INFORMATION: Xaa = Any Amino Acid

<400> SEQUENCE: 7

Ser Xaa Gly Xaa Xaa Ser
 1               5

<210> SEQ ID NO 8
<211> LENGTH: 6
<212> TYPE: PRT
<213> ORGANISM: Artificial Sequence
<220> FEATURE:
<223> OTHER INFORMATION: Variant
<221> NAME/KEY: VARIANT
<222> LOCATION: (1)...(6)
<223> OTHER INFORMATION: Xaa = Any Amino Acid
<221> NAME/KEY: VARIANT
<222> LOCATION: (1)...(6)
<223> OTHER INFORMATION: Xaa = Any Amino Acid
<221> NAME/KEY: VARIANT
<222> LOCATION: (1)...(6)
<223> OTHER INFORMATION: Xaa = Any Amino Acid

<400> SEQUENCE: 8

Leu Xaa Gly Xaa Xaa Gly
 1               5

<210> SEQ ID NO 9
<211> LENGTH: 6
<212> TYPE: PRT
<213> ORGANISM: Artificial Sequence
<220> FEATURE:
<223> OTHER INFORMATION: Variant
<221> NAME/KEY: VARIANT
<222> LOCATION: (1)...(6)
<223> OTHER INFORMATION: Xaa = Any Amino Acid
<221> NAME/KEY: VARIANT
<222> LOCATION: (1)...(6)
<223> OTHER INFORMATION: Xaa = Any Amino Acid
<221> NAME/KEY: VARIANT
<222> LOCATION: (1)...(6)
<223> OTHER INFORMATION: Xaa = Any Amino Acid

<400> SEQUENCE: 9

Gly Xaa Gly Xaa Xaa Gly
 1               5

<210> SEQ ID NO 10
<211> LENGTH: 50
<212> TYPE: PRT
<213> ORGANISM: Rattus norvegicus

<400> SEQUENCE: 10

Tyr Ser Met Val Gly Cys Gln Arg Ala Met Met Ala Asn Arg Leu Ser
 1               5                  10                  15

Phe Phe Phe Asp Phe Lys Gly Pro Ser Ile Ala Leu Asp Thr Ala Cys

-continued

```
                20                  25                  30
Ser Ser Ser Leu Leu Ala Leu Gln Asn Ala Tyr Gln Ala Ile Arg Ser
            35                  40                  45

Gly Glu
    50

<210> SEQ ID NO 11
<211> LENGTH: 50
<212> TYPE: PRT
<213> ORGANISM: Fungal:  Aspergillis terreus

<400> SEQUENCE: 11

Tyr Ser Ala Thr Gly Val Ala Val Ser Val Ala Ser Asn Arg Ile Ser
1               5                   10                  15

Tyr Phe Phe Asp Trp His Gly Pro Ser Met Thr Ile Asp Thr Ala Cys
                20                  25                  30

Ser Ser Ser Leu Val Ala Val His Leu Ala Val Gln Gln Leu Arg Thr
            35                  40                  45

Gly Gln
    50

<210> SEQ ID NO 12
<211> LENGTH: 50
<212> TYPE: PRT
<213> ORGANISM: Fungal:  Penicillium palatum

<400> SEQUENCE: 12

Trp Met Gly Ile Gly Thr Ala Tyr Cys Gly Val Pro Asn Arg Ile Ser
1               5                   10                  15

Tyr His Leu Asn Leu Met Gly Pro Ser Thr Ala Val Asp Ala Ala Cys
                20                  25                  30

Ala Ser Ser Leu Val Ala Ile His His Gly Val Gln Ala Ile Arg Leu
            35                  40                  45

Gly Glu
    50

<210> SEQ ID NO 13
<211> LENGTH: 50
<212> TYPE: PRT
<213> ORGANISM: Fungal:  Penicillium palatum

<400> SEQUENCE: 13

Ser Asp Arg Val Gln Ile Leu Thr Tyr Val Met Gln Ile Gly Leu Ser
1               5                   10                  15

Ala Leu Leu Gln Ser Asn Gly Ile Thr Pro Gln Ala Val Ile Gly His
                20                  25                  30

Ser Val Gly Glu Ile Ala Ala Ser Val Val Ala Gly Ala Leu Ser Pro
            35                  40                  45

Ala Glu
    50

<210> SEQ ID NO 14
<211> LENGTH: 46
<212> TYPE: PRT
<213> ORGANISM: Rattus norvegicus

<400> SEQUENCE: 14

Phe Val Ser Leu Thr Ala Ile Gln Ile Ala Leu Ile Asp Leu Leu Thr
1               5                   10                  15
```

-continued

Ser Met Gly Leu Lys Pro Asp Gly Ile Ile Gly His Ser Leu Gly Glu
              20                  25                  30

Val Ala Cys Gly Tyr Ala Asp Gly Cys Leu Ser Gln Arg Glu
         35                  40                  45

<210> SEQ ID NO 15
<211> LENGTH: 48
<212> TYPE: PRT
<213> ORGANISM: Fungal: Aspergillis terreus

<400> SEQUENCE: 15

Phe Ser Gln Pro Leu Cys Cys Ala Val Gln Ile Val Leu Val Arg Leu
 1               5                  10                  15

Leu Glu Ala Ala Arg Ile Arg Phe Thr Ala Val Val Gly His Ser Ser
              20                  25                  30

Gly Glu Ile Ala Cys Ala Phe Ala Ala Gly Leu Ile Ser Ala Ser Leu
         35                  40                  45

<210> SEQ ID NO 16
<211> LENGTH: 40
<212> TYPE: PRT
<213> ORGANISM: Fungal: Penicillium palatum

<400> SEQUENCE: 16

Tyr Thr Thr Arg Leu Asp Asn Asp Thr Lys Pro Phe Pro Gly Ser His
 1               5                  10                  15

Pro Leu His Gly Thr Glu Ile Val Pro Ala Ala Gly Leu Ile Asn Thr
              20                  25                  30

Phe Leu Lys Gly Thr Gly Gly Gln
         35                  40

<210> SEQ ID NO 17
<211> LENGTH: 40
<212> TYPE: PRT
<213> ORGANISM: Rattus norvegicus

<400> SEQUENCE: 17

Asn Ile Asp Ala Ser Ser Glu Ser Ser Asp His Tyr Leu Val Asp His
 1               5                  10                  15

Cys Ile Asp Gly Arg Val Leu Phe Pro Gly Thr Gly Tyr Leu Tyr Leu
              20                  25                  30

Val Trp Lys Thr Leu Ala Arg Ser
         35                  40

<210> SEQ ID NO 18
<211> LENGTH: 41
<212> TYPE: PRT
<213> ORGANISM: Fungal: Aspergillis terreus

<400> SEQUENCE: 18

Trp Leu Asn Phe Val Arg Pro Arg Asp Ile Glu Trp Leu Asp Gly His
 1               5                  10                  15

Ala Leu Gln Gly Gln Thr Val Phe Pro Ala Ala Gly Tyr Ile Val Met
              20                  25                  30

Ala Met Glu Ala Ala Leu Met Ile Ala
         35                  40

<210> SEQ ID NO 19
<211> LENGTH: 48
<212> TYPE: PRT
<213> ORGANISM: Fungal: Aspergillis terreus

```
<400> SEQUENCE: 19

Val Pro Val Val Ala Leu Ala Glu Arg Asn Ala Ser Ile Val His Val
 1               5                  10                  15

Arg Pro Asp Tyr Ile Tyr Thr Glu Ala Asp Asn Asn Leu Ser Glu Gly
                20                  25                  30

Gly Gly Ser Leu Met Val Thr Val Leu Ala Ala Val Leu Ala Glu
            35                  40                  45

<210> SEQ ID NO 20
<211> LENGTH: 50
<212> TYPE: PRT
<213> ORGANISM: Rattus norvegicus

<400> SEQUENCE: 20

Val Pro Val Val Tyr Thr Thr Ala Tyr Tyr Ser Leu Val Val Arg Gly
 1               5                  10                  15

Arg Ile Gln His Gly Glu Thr Val Leu Ile His Ser Gly Ser Gly Gly
                20                  25                  30

Val Gly Gln Ala Ala Ile Ser Ile Ala Leu Ser Leu Gly Cys Arg Val
            35                  40                  45

Phe Thr
    50

<210> SEQ ID NO 21
<211> LENGTH: 49
<212> TYPE: PRT
<213> ORGANISM: Actinomycete: Streptomyces

<400> SEQUENCE: 21

Val Pro Ile Ala Tyr Thr Thr Ala His Tyr Ala Leu His Asp Leu Ala
 1               5                  10                  15

Gly Leu Arg Ala Gly Gln Ser Val Leu Ile His Ala Ala Gly Gly
                20                  25                  30

Val Gly Met Ala Ala Val Ala Leu Ala Arg Arg Ala Gly Leu Ala Glu
            35                  40                  45

Val

<210> SEQ ID NO 22
<211> LENGTH: 50
<212> TYPE: PRT
<213> ORGANISM: Fungal: Aspergillis terreus

<400> SEQUENCE: 22

Pro Thr Arg Val Arg Ser Ile Asp Ala Glu Thr Leu Phe Ala Ala Asp
 1               5                  10                  15

Lys Thr Tyr Leu Leu Val Gly Leu Thr Gly Asp Leu Gly Arg Ser Leu
                20                  25                  30

Gly Arg Trp Met Val Gln His Gly Ala Cys His Ile Val Leu Thr Ser
            35                  40                  45

Arg Asn
    50

<210> SEQ ID NO 23
<211> LENGTH: 48
<212> TYPE: PRT
<213> ORGANISM: Fungal: Penicillium palatum

<400> SEQUENCE: 23
```

```
Leu Pro Ala Ser Glu Gly Pro Arg Leu Pro Arg Pro Gly Thr
1               5                   10                  15

Tyr Leu Ile Thr Gly Gly Leu Gly Val Leu Gly Leu Glu Val Ala Asp
            20                  25                  30

Phe Leu Val Glu Lys Gly Ala Arg Arg Leu Leu Leu Ile Ser Arg Arg
        35                  40                  45
```

<210> SEQ ID NO 24
<211> LENGTH: 49
<212> TYPE: PRT
<213> ORGANISM: Rattus norvegicus

<400> SEQUENCE: 24

```
Pro Thr Leu Ile Ser Ala Ile Ser Lys Thr Phe Cys Pro Glu His Lys
1               5                   10                  15

Ser Tyr Ile Ile Thr Gly Gly Leu Gly Gly Phe Gly Leu Glu Leu Ala
            20                  25                  30

Arg Trp Leu Val Leu Arg Gly Ala Gln Arg Leu Val Leu Thr Ser Arg
        35                  40                  45

Ser
```

<210> SEQ ID NO 25
<211> LENGTH: 50
<212> TYPE: PRT
<213> ORGANISM: Fungal: Aspergillis terreus

<400> SEQUENCE: 25

```
Val Arg Gln Ile Val Ile Asp Gly Leu Ser Ala Lys Leu Gln Val Thr
1               5                   10                  15

Leu Gln Ile Pro Asp Gly Glu Ser Val His Pro Thr Ile Pro Leu Ile
            20                  25                  30

Asp Gln Gly Val Asp Ser Leu Gly Ala Val Thr Val Gly Thr Trp Phe
        35                  40                  45

Ser Lys
    50
```

<210> SEQ ID NO 26
<211> LENGTH: 50
<212> TYPE: PRT
<213> ORGANISM: Rattus norvegicus

<400> SEQUENCE: 26

```
Gly Asp Gly Glu Ala Gln Arg Asp Leu Val Lys Ala Val Ala His Ile
1               5                   10                  15

Leu Gly Ile Arg Asp Leu Ala Gly Ile Asn Leu Asp Ser Ser Leu Ala
            20                  25                  30

Asp Leu Gly Leu Asp Ser Leu Met Gly Val Glu Val Arg Gln Ile Leu
        35                  40                  45

Glu Arg
    50
```

<210> SEQ ID NO 27
<211> LENGTH: 47
<212> TYPE: PRT
<213> ORGANISM: Fungal: Penicillium palatum

<400> SEQUENCE: 27

```
Lys Ala Tyr Leu Asp Glu Lys Ile Arg Gly Cys Val Ala Lys Val Leu
1               5                   10                  15
```

-continued

Gln Met Thr Ala Glu Asp Val Asp Ser Lys Ala Ala Leu Ala Asp Leu
            20                  25                  30

Gly Val Asp Ser Val Met Thr Val Thr Leu Arg Arg Gln Leu Gln
        35                  40                  45

<210> SEQ ID NO 28
<211> LENGTH: 22
<212> TYPE: PRT
<213> ORGANISM: Fungal:  Aspergillis terreus

<400> SEQUENCE: 28

Ser Thr Cys Ala Val Phe Gly Leu Gly Gly Val Gly Leu Ser Val Ile
 1               5                  10                  15

Met Gly Cys Lys Ala Ala
            20

<210> SEQ ID NO 29
<211> LENGTH: 22
<212> TYPE: PRT
<213> ORGANISM: Rattus norvegicus

<400> SEQUENCE: 29

Thr Val Leu Ile His Ser Gly Ser Gly Gly Val Gly Gln Ala Ala Ile
 1               5                  10                  15

Ser Ile Ala Leu Ser Leu
            20

<210> SEQ ID NO 30
<211> LENGTH: 22
<212> TYPE: PRT
<213> ORGANISM: Fungal:  Aspergillis terreus

<400> SEQUENCE: 30

Tyr Ile Tyr Thr Glu Ala Asp Asn Asn Leu Ser Glu Gly Gly Gly Ser
 1               5                  10                  15

Leu Met Val Thr Val Leu
            20

<210> SEQ ID NO 31
<211> LENGTH: 22
<212> TYPE: PRT
<213> ORGANISM: Fungal:  Aspergillis terreus

<400> SEQUENCE: 31

Thr Tyr Leu Leu Val Gly Leu Thr Gly Asp Leu Gly Arg Ser Leu Gly
 1               5                  10                  15

Arg Trp Met Val Gln His
            20

<210> SEQ ID NO 32
<211> LENGTH: 22
<212> TYPE: PRT
<213> ORGANISM: Fungal:  Penicillium palatum

<400> SEQUENCE: 32

Thr Tyr Leu Ile Thr Gly Gly Leu Gly Val Leu Gly Leu Glu Val Ala
 1               5                  10                  15

Asp Phe Leu Val Glu Lys
            20

<210> SEQ ID NO 33
<211> LENGTH: 22

```
<212> TYPE: PRT
<213> ORGANISM: Rattus norvegicus

<400> SEQUENCE: 33

Ser Tyr Ile Ile Thr Gly Gly Leu Gly Gly Phe Gly Leu Glu Leu Ala
 1               5                  10                  15

Arg Trp Leu Val Leu Arg
            20

<210> SEQ ID NO 34
<211> LENGTH: 17
<212> TYPE: PRT
<213> ORGANISM: Fungal:  Aspergillis terreus

<400> SEQUENCE: 34

Ile Leu Glu Ile Gly Ala Gly Thr Gly Ala Thr Lys Tyr Val Leu
 1               5                  10                  15

Pro

<210> SEQ ID NO 35
<211> LENGTH: 50
<212> TYPE: PRT
<213> ORGANISM: Consensus Sequence
<220> FEATURE:
<221> NAME/KEY: VARIANT
<222> LOCATION: (1)...(50)
<223> OTHER INFORMATION: Xaa = Any Amino Acid

<400> SEQUENCE: 35

Xaa Xaa Xaa Xaa Gly Xaa Xaa Xaa Xaa Xaa Xaa Asn Arg Xaa Ser
 1               5                  10                  15

Xaa Xaa Xaa Xaa Xaa Xaa Gly Pro Ser Xaa Xaa Xaa Asp Xaa Ala Cys
            20                  25                  30

Xaa Ser Ser Leu Xaa Ala Xaa Xaa Xaa Xaa Xaa Gln Xaa Xaa Arg Xaa
        35                  40                  45

Gly Xaa
    50

<210> SEQ ID NO 36
<211> LENGTH: 50
<212> TYPE: PRT
<213> ORGANISM: Consensus Sequence
<220> FEATURE:
<221> NAME/KEY: VARIANT
<222> LOCATION: (1)...(50)
<223> OTHER INFORMATION: Xaa = Any Amino Acid

<400> SEQUENCE: 36

Xaa Xaa Xaa Xaa Xaa Xaa Leu Xaa Xaa Xaa Xaa Gln Ile Xaa Leu Xaa
 1               5                  10                  15

Xaa Leu Leu Xaa Xaa Xaa Xaa Xaa Xaa Xaa Xaa Xaa Xaa Gly His
            20                  25                  30

Ser Xaa Gly Glu Xaa Ala Xaa Xaa Xaa Xaa Gly Xaa Xaa Ser Xaa
        35                  40                  45

Xaa Xaa
    50

<210> SEQ ID NO 37
<211> LENGTH: 40
<212> TYPE: PRT
<213> ORGANISM: Consensus Sequence
<220> FEATURE:
<221> NAME/KEY: VARIANT
```

```
<222> LOCATION: (1)...(50)
<223> OTHER INFORMATION: Xaa = Any Amino Acid

<400> SEQUENCE: 37

Xaa Xaa Xaa Xaa Xaa Xaa Xaa Xaa Xaa Xaa Xaa Xaa Xaa Xaa Xaa His
 1               5                  10                  15

Xaa Xaa Xaa Gly Xaa Xaa Xaa Xaa Pro Xaa Xaa Gly Xaa Xaa Xaa Xaa
                20                  25                  30

Xaa Xaa Xaa Xaa Xaa Xaa Xaa Xaa
        35                  40

<210> SEQ ID NO 38
<211> LENGTH: 48
<212> TYPE: PRT
<213> ORGANISM: Consensus Sequence
<220> FEATURE:
<221> NAME/KEY: VARIANT
<222> LOCATION: (1)...(50)
<223> OTHER INFORMATION: Xaa = Any Amino Acid

<400> SEQUENCE: 38

Val Pro Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Gly
                20                  25                  30

Xaa Gly Xaa Xaa Xaa Xaa Xaa Xaa Xaa Xaa Xaa Xaa Xaa Xaa Xaa Xaa
        35                  40                  45

<210> SEQ ID NO 39
<211> LENGTH: 50
<212> TYPE: PRT
<213> ORGANISM: Consensus Sequence
<220> FEATURE:
<221> NAME/KEY: VARIANT
<222> LOCATION: (1)...(50)
<223> OTHER INFORMATION: Xaa = Any Amino Acid

<400> SEQUENCE: 39

Xaa Xaa Xaa Xaa Xaa Xaa Xaa Xaa Xaa Xaa Xaa Xaa Xaa Xaa Xaa Xaa
 1               5                  10                  15

Xaa Xaa Tyr Xaa Xaa Xaa Gly Xaa Gly Xaa Xaa Gly Xaa Xaa Xaa Xaa
                20                  25                  30

Xaa Xaa Xaa Xaa Val Xaa Xaa Gly Ala Xaa Xaa Xaa Xaa Leu Xaa Ser
        35                  40                  45

Arg Xaa
     50

<210> SEQ ID NO 40
<211> LENGTH: 50
<212> TYPE: PRT
<213> ORGANISM: Consensus Sequence
<220> FEATURE:
<221> NAME/KEY: VARIANT
<222> LOCATION: (1)...(50)
<223> OTHER INFORMATION: Xaa = Any Amino Acid

<400> SEQUENCE: 40

Xaa Xaa Xaa Xaa Xaa Xaa Xaa Xaa Xaa Xaa Xaa Xaa Xaa Xaa Xaa Xaa
 1               5                  10                  15

Leu Xaa Xaa Xaa Xaa Xaa Xaa Xaa Xaa Xaa Xaa Xaa Xaa Xaa Leu Xaa
                20                  25                  30

Asp Xaa Gly Xaa Asp Ser Xaa Xaa Xaa Val Xaa Xaa Xaa Xaa Xaa Xaa
        35                  40                  45
```

-continued

```
Xaa Xaa
    50

<210> SEQ ID NO 41
<211> LENGTH: 17
<212> TYPE: PRT
<213> ORGANISM: Consensus Sequence
<220> FEATURE:
<221> NAME/KEY: VARIANT
<222> LOCATION: 1, 2
<223> OTHER INFORMATION: Xaa = Hydrophobic Amino Acid
<221> NAME/KEY: VARIANT
<222> LOCATION: 3
<223> OTHER INFORMATION: Xaa = Asp or Glu
<221> NAME/KEY: VARIANT
<222> LOCATION: 4, 11, 15, 16
<223> OTHER INFORMATION: Xaa = Hydrophobic Amino Acid
<221> NAME/KEY: VARIANT
<222> LOCATION: 17
<223> OTHER INFORMATION: Xaa = Pro or Charged Amino Acid
<221> NAME/KEY: VARIANT
<222> LOCATION: 6, 8, 10, 12, 13, 14
<223> OTHER INFORMATION: Xaa = Any Amino Acid

<400> SEQUENCE: 41

Xaa Xaa Xaa Xaa Gly Xaa Gly Xaa Gly Xaa Xaa Xaa Xaa Xaa Xaa Xaa
 1               5                  10                  15

Xaa
```